US007553932B1

(12) United States Patent
Von Herrath et al.

(10) Patent No.: US 7,553,932 B1
(45) Date of Patent: Jun. 30, 2009

(54) METHODS OF TREATING VIRAL INFECTION WITH IL-10 RECEPTOR ANTAGONISTS

(75) Inventors: Matthias G. Von Herrath, Del Mar, CA (US); Anne Mette Ejrnaes, San Diego, CA (US)

(73) Assignee: La Jolla Institute for Allergy and Immunology, La Jolla, CA (US)

( * ) Notice: Subject to any disclaimer, the term of this patent is extended or adjusted under 35 U.S.C. 154(b) by 0 days.

(21) Appl. No.: 11/411,222

(22) Filed: Apr. 25, 2006

Related U.S. Application Data

(60) Provisional application No. 60/674,795, filed on Apr. 25, 2005.

(51) Int. Cl.
*C07K 14/52* (2006.01)
*A61K 38/19* (2006.01)

(52) U.S. Cl. .................................... 530/351; 424/85.1

(58) Field of Classification Search ........................ None
See application file for complete search history.

(56) References Cited

U.S. PATENT DOCUMENTS

| 6,818,748 B2 * | 11/2004 | Fulton et al. ............. 530/387.3 |
| 2004/0142893 A1 | 7/2004 | Ikeda et al. .................... 514/44 |

FOREIGN PATENT DOCUMENTS

| WO | 98/10787 | 3/1998 |
| WO | WO 98/10792 | 3/1998 |
| WO | 98/47516 | 10/1998 |
| WO | 00/09150 | 2/2000 |
| WO | 00/35472 | 6/2000 |
| WO | 00/43030 | 7/2000 |

OTHER PUBLICATIONS

Rigopoulou et al., Blocking of IL-10 Receptor-A novel approach to stimulate virus-specific T cell reactivity in chronic hepatitis C virus (HCV) infection, Hepatology, 2000, 32(4,2), p. 304A.*
Silva et al., Blocking the receptor for interleukin 10 protects mice from lethal listeriosis, Antimicrobial Agents and Chemotherapy, 2001, 45(4):1312-1314.*
van Deuren et al., The Pattern of Interleukin-1b (IL-1b) and Its Modulating Agents IL-1 Receptor Antagonist and IL-1 Soluble Receptor Type II in Acute Meningococcal Infections, Blood, 1997, 90(3):1101-1108.*
Brady et al., Hepatitis C virus non-structural protein 4 suppresses Th1 responses by stimulating IL-10 production from monocytes, European Journal of Immunology, 2003, 33:3448-3457.*
Tsai et al., Detection of Type 2—Like T-Helper Cells in Hepatitis C Virus Infection: Implications for Hepatitis C Virus Chronicity, Hepatology, 1997, 25:449-458.*
Stockl et al., Human major group rhinoviruses downmodulate the accessory function of monocytes by inducing IL-10, Journal of Clinical Investigation, 1999, 104:957-965.*

Li et al., Interferon-gamma (IFN-γ) regulates production of IL-10 and IL-12 in human herpesvirus-6 (HHV-6)-infected monocyte/macrophage lineage, Clin. Exp. Immunol., 1997, 109:421-425.*
Asadullah, K., et al., Interleukin-10 therapy—review of a new approach, Pharmacological Reviews, 55:241-269 (2003).
Belkaid, Y., et al., The role of interleukin (IL)-10 in the persistence of *Leishmania major* in the skin after healing and the therapeutic potential of anti-IL-10 receptor antibody for sterile cure, J. Exp. Med., 194:1497-1506 (2001).
Bogdan, C., et al., Machophage deactivation by interleukin 10, J. Exp. Med., 174:1549-1555 (1991).
Chang, W.L.W., et al., Human cytomegalovirus-encoded interleukin-10 homolog inhibits maturation of dendritic cells and alters their functionality, Journal of Virology, 78:8720-8731 (2004).
Ding, Y., et al., Suppressor of cytokine signaling 1 inhibits IL-10-mediated immune responses, The Journal of Immunology, 170:1383-1391 (2003).
Fernandez, S., et al., Inhibition of IL-10 receptor function in Alveolar macrophages by toll-like receptor agonists, The Journal of Immunology, 172:2613-2620 (2004).
Groux, H., et al., A transgenic model to analyze the immunoregulatory role of IL-10 secreted by antigen-presenting cells, Journal of Immunology, 162:1723-1729 (1999).
Havlir, D.V., et al., Serum interleukin-6 (IL-6), IL-10, tumor necrosis factor (TNF) alpha, soluble type II TNF receptor, and transforming growth factor beta levels in human immunodeficiency virus type 1-infected individuals with *Mycobacterium avium* complex disease, Journal of Clinical Microbiology, 39:298-303 (2001).
Higgins, S.C., et al., Toll-like receptor 4-mediated innate IL-10 activates antigen-specific regulatory T cells and confers resistance to *Bordetella pertussis* by inhibiting inflammatory pathology, The Journal of Immunology, 171:3119-3127 (2003).
Ho, A. S.-Y., et al., A receptor for interleukin 10 is related to interferon receptors, Proc. Natl. Acad. Sci. USA, 90:11267-11271 (1993).
Ho, A. S.-Y., et al., Interleukin-10 and its receptor, Therapeutic Immunology, 1:173-185 (1994).
Jones, K.D., et al., Involvement of interleukin-10(IL-10) and viral IL-6 in the spontaneous growth of kaposi's sarcoma herpesvirus-associated infected primary effusion lymphoma cells, Blood, 94:2871-2879 (1999).
Josephson, K., et al., Noncompetitive antibody neutralization of IL-10 revealed by protein engineering and X-ray crystallography, Structure, 10:981-987 (2002).
Kane, M.M., et al., The role of IL-10 in promoting disease progression in Leishmaniasis, The Journal of Immunology, 166:1141-1147 (2001).
Kotenko, S.V., et al., Human cytomegalovirus harbors its own unique IL-10 homolog (cmvIL-10), PNAS, 97:1695-1700 (2000).
Laichalk, L., et al., Interleukin-10 inhibits neutrophil phagocytic and bactericidal activity, FEMS Immunology and Medical Microbiology 15:181-187 (1996).
Liu, Y., et al., The EBV IL-10 homologue is a selective agonist with impaired binding to the IL-10 receptor, The Journal of Immunology, 158:604-613 (1997).

(Continued)

*Primary Examiner*—Bruce Campell
*Assistant Examiner*—Nicole Kinsey White
(74) *Attorney, Agent, or Firm*—Pillsbury Winthrop Shaw Pittman LLP

(57) ABSTRACT

Compositions, methods and uses employing interleukin-10 receptor (IL-10R) or interleukin 10R ligand (e.g., IL-10) antagonists for viral treatment, identification, screening and diagionstics.

34 Claims, 11 Drawing Sheets

OTHER PUBLICATIONS

Figure 1:
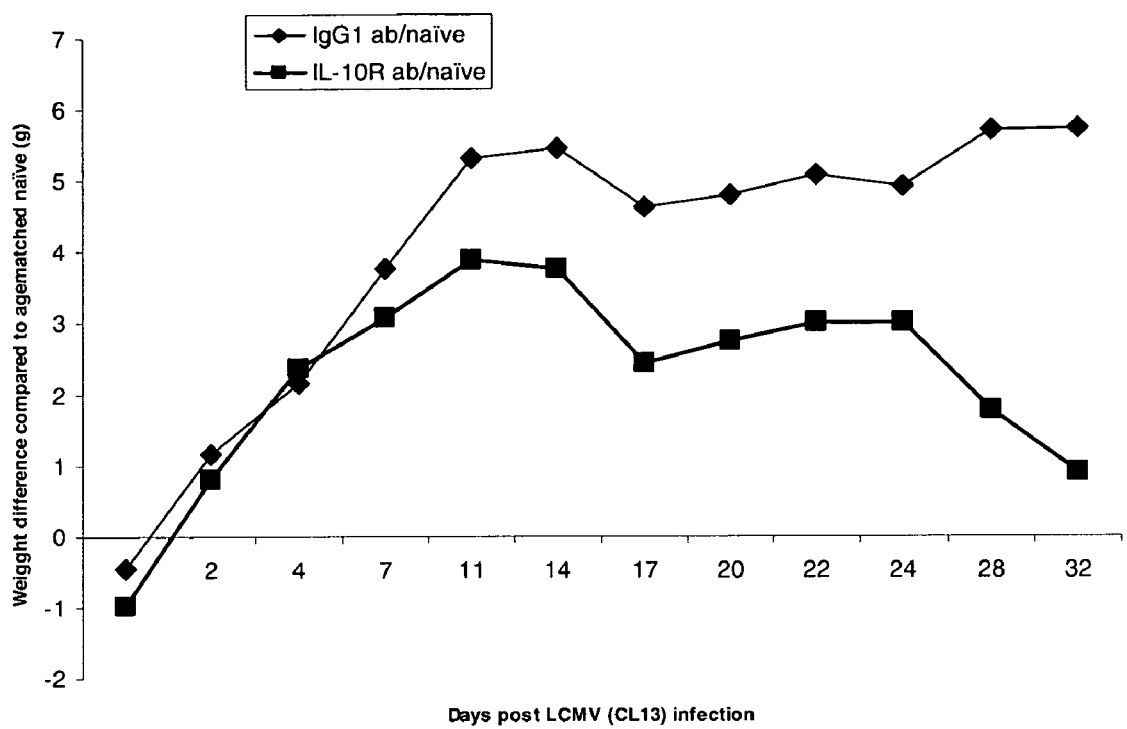

Lyons, A, et al., Major injury induces increased production of interleukin-10 by cells of the immune system with a negative impact on resistance to infection, Annals of Surgery, 226:450-460 (1997).

Moore, K.W., et al., Interleukin-10 and the interleukin-10 receptor, Annu. Rev. Immunol., 19:683-765 (2001).

Muehlstedt, S.G., et al., Increased IL-10 production and HLA-DR suppression in the lungs of injured patients precede the development of nosocomial pneumonia, Shock, 17:443-450 (2002).

Murray, H., et al., Determinants of response to interleukin-10 receptor blockage immunotherapy in experimental visceral leishmaniasis, Journal of Infectious Diseases, 188:458-464 (2003).

Murray, H., Interleukin 10 receptor blockage—pentavalent antimony treatment in experimental visceral leishmaniasis, Acta Tropica, 93:295-301 (2005).

Murray, H.W., et al., Interleukin-10 (IL-10) in experimental visceral leishmaniasis and IL-10 receptor blockage as immunotherapy, Infection and Immunity, 70:6284-6293 (2002).

O'Farrell, A.-M., et al., IL-10 inhibits macrophage activation and proliferation by distinct signaling mechanisms: evidence for Stat3-dependent and -independent pathways, The EMBO Journal, 17:1006-1018 (1998).

Opal, S.M., et al., The role of interleukin-10 in critical illness, Current Opinion in Infectious Diseases, 12:221-226 (2000).

Payvandi, F., et al., Exogenous and Endogenous IL-10 regulate IFN-α production by peripheral blood mononuclear cells in response to viral stimulation, Journal of Immunology, 160:5861-5868 (1998).

Redpath, S., et al., Hijacking and exploitation of IL-10 by intracellular pathogens, Trends in Microbiology, 9:86-92 (2001).

Silva, R.A., et al., Blocking the receptor for IL-10 improves antimycobacterial chemotherapy and vaccination, The Journal of Immunology, 167:1535-1541 (2001).

Spencer, J.V., et al., Potent immunosuppressive activities of cytomegalovirus-encoded interleukin-10, Journal of Virology, 76:1285-1292 (2002).

Spencer, S.D., et al., The orphan receptor CRF2-4 is an essential subunit of the interleukin 10 receptor, J. Exp. Med., 187:571-578 (1998).

Stylianou, E., et al., IL-10 in HIV infection: increasing serum IL-10 levels with disease Progression—Down-Regulatory Effect of potent anti-retroviral therapy. Clin. Exp. Immunol., 116:115-120 (1999).

Suzuki, T., et al., Viral interleukin 10 (IL-10), the human herpes virus 4 cellular IL-10 homologue, induces local anergy to allogeneic and syngeneic tumors, J. Exp. Med., 182:477-486 (1995).

Vicari, A.P., et al., Interleukin-10 in viral diseases and cancer: exiting the labyrinth?. Immunological Review 202:223-236 (2004).

Humphreys, et al., Cytomegalovirus Exploits IL-10-Mediated Immune Regulation in the Salivary Glands, *JEM* 204(5): 1217-1225 (2007).

Rigopoulou, et al., Blocking of Interleukin-10 Receptor-A Novel Approach to Stimulate T-Helper Cell Type 1 Responses to Hepatitis C. Virus, *Clinical Immunology* 117:57-64 (2005).

* cited by examiner

METHODS OF TREATING VIRAL INFECTION WITH IL-10 RECEPTOR ANTAGONISTS

RELATED APPLICATIONS

This application is claims the benefit of priority of U.S. Application Ser. No. 60/674,795, filed Apr. 25, 2005, which is expressly incorporated herein by reference.

TECHNICAL FIELD

The invention relates to compositions, methods and uses employing interleukin-10 receptor (IL-10R) or interleukin 10R ligand (e.g., IL-10) antagonists for viral treatment, identification, screening and diagnostics.

INTRODUCTION

Interleukin-10 (IL-10) is an immunosuppressive cytokine with implications for various immune and inflammatory diseases. It inhibits a broad spectrum of cellular immune responses, acting on antigen-presenting cells (APCs) and T cells by inhibiting pro-inflammatory cytokine production, co-stimulation, MHC class II expression and chemokine secretion (Moore et al., *Annu Rev Immunol* 11:165 (1993); Pestka et al., *Annu Rev Immunol* 22:929 (2004)). Elevated levels of IL-10 mRNA have been observed in immune-responsive versus non-responsive metastatic melanoma lesions (Mocellin et al., *Int J Cancer* 93:236 (2001)). Moreover, treatment with a combination of anti-IL-10 receptor (IL-10R) monoclonal antibody (mAb) and toll-like receptor 9 (TLR9) ligands has been shown to have potent therapeutic anti-tumor effects (Vicari et al., *J Exp Med* 196:541 (2002); Vicari, A. P. and Trinchieri, G., *Immunol Rev* 202:223 (2004)) pointing to the role of IL-10 in the development of cancer.

SUMMARY

Methods of treating a subject for a viral infection are provided. In one embodiment, a method includes administering to a subject an amount of an IL-10 receptor (IL-10R) antagonist or an IL-10 antagonist sufficient to treat the subject (e.g., a mammal, such as a human). Treatable viral infections include chronic or acute infections.

Antagonists can bind to IL-10R alpha chain extracellular domain, or IL-10R beta chain extracellular domain. Antagonists can inhibit IL-10 or IL-10R signaling or expression. Antagonists can inhibit binding of a ligand, such as IL-10, to IL-10R. Antagonists can inhibit signaling of ligand-bound IL-10R complex (e.g., activation of STAT 3 or STAT1 in a responder cell line).

Exemplary antagonists include small molecules. Exemplary antagonists include polypeptides and nucleic acids. Specific examples of polypeptides include monoclonal and polyclonal antibodies (e.g., mammalian, primatized, humanized and fully human), and dominant negative IL-10R ligand and soluble IL-10R. Antibodies include full length and fragments and subsequences of a full length antibody having two heavy chains and two light chains (e.g., Fab, Fab', F(ab')$_2$, Fv, Fd, single-chain Fv (scFv), disulfide linked Fv, light chain variable (VL) and heavy chain variable (VH)).

Particular antibodies include, for example, antibodies having substantially the same binding affinity as an antibody selected from or produced by produced by 1B1.3a (BD Biosciences, Pharmingen Division, Cat. No. 550012) and 1B1.2 hybridoma (DNAX), and an anti-mouse IL-10R(R & D Systems, Cat. No. AF-474-NA). Additional particular examples include antibodies that competitively inhibit binding of an antibody selected from or produced by 1B1.3a (BD Biosciences, Pharmingen Division, Cat. No. 550012), 1B1.2 hybridoma (DNAX) and anti-mouse IL-10R(R & D Systems, Cat. No. AF-474-NA) to IL-1R. Specific examples of antibodies include 1B1.3a (BD Biosciences, Pharmingen Division, Cat. No. 550012), 1B1.2 hybridoma (DNAX) and anti-mouse IL-10R(R & D Systems, Cat. No. AF-474-NA).

Exemplary viruses include herpesvirus, hepatitis virus, immunodeficiency virus, flavivirus, papilloma virus (PV), polyoma virus, rhabdovirus, a myxovirus, an arenavirus, a coronavirus, poxvirus, adenovirus, reovirus, picornavirus, togavirus, bunyavirus, parvovirus and retrovirus. Specific non-limiting examples of herpesvirus include β-herpesvirus, γ-herpesvirus, Epstein Bar Virus (EBV), Cytomegalovirus (CMV), varicella zoster virus (VZV/HHV-3) and human herpes virus 1, 2, 4, 5, 6, 7, or 8 (HHV-8, Kaposi's sarcoma-associated virus). Specific non-limiting examples of hepatitis virus include hepatitis A, B, C, D, E or G. Specific non-limiting examples of immunodeficiency virus include human immunodeficiency virus (HIV, e.g., HIV-1, HIV-2 and HIV-3). Specific non-limiting examples of flavivirus include Yellow Fever virus, Dengue virus, Japanese Encephalitis and West Nile viruses. Specific non-limiting examples of papilloma virus include human papilloma virus (HPV, e.g., HPV strain 1, 6, 11, 16, 18, 30, 31, 42, 43, 44, 45, 51, 52 and 54). Specific non-limiting examples of polyoma virus include BK virus (BKV) and JC virus (JCV). Specific non-limiting examples of rhabdovirus include rabies virus and vesiculovirus. Specific non-limiting examples of myxovirus include paramyxovirus (e.g., measles, mumps, pneumovirus or respiratory syncytial virus (RSV)) and orthomyxovirus (e.g., influenza virus, such as influenza A, influenza B and influenza C). Specific non-limiting examples of arenavirus include lymphocytic choriomeningitis virus (LCMV), Junin virus, Lassa virus, Guanarito virus, Sabia virus and Machupo virus. Specific non-limiting examples of coronavirus include virus that cause a common cold and severe acute respiratory syndrome (SARS). Specific non-limiting examples of poxvirus include vaccinia virus, Molluscum contagiosum, variola major or variola minor smallpox virus, cow pox, camel pox, sheep pox and monkey pox. Specific non-limiting examples of adenovirus include viral infection of the bronchii, lung, stomach, intestine (gastroenteritis), eye (conjunctivitis), bladder (cystitis) and skin. Specific non-limiting examples of reovirus include rotavirus, cypovirus and orbivirus. Specific non-limiting examples of picornavirus include rhinovirus (those that cause common cold), apthovirus, hepatovirus, enterovirus and cardiovirus. Specific non-limiting examples of togavirus include alphavirus, sindbus virus and rubellavirus. Specific non-limiting examples of bunyavirus include hantavirus, phlebovirus and nairovirus. Specific non-limiting examples of retrovirus include alpha, beta, delta, gamma, epsilon, lentivirus (e.g., a bovine, porcine, equine, canine, feline or primate immunodeficiency virus such as human T-cell leukemia virus 1 or 2), spumavirus and human T-cell leukemia virus.

Methods of treatment include methods that reduce virus titer, reduce virus proliferation, reduce an amount of a virus protein or reduce an amount of a virus nucleic acid. Methods of treatment also include methods that increase or stimulate virus clearance, reduce or inhibit virus infection, reduce or inhibit increases in virus titer, reduce or inhibit virus proliferation, reduce or inhibit synthesis of a virus protein or a virus nucleic acid, or reduce or inhibit virus reactivation from latency. Methods of treatment further include methods that sufficient to reduce one or more physiological conditions, disorders, illness, diseases or symptoms caused by or associated with virus infection or pathology.

Methods of treatment include methods that improve one or more physiological conditions, disorders, illness, diseases or symptoms caused by or associated with virus infection or pathology; and methods that reduce or ameliorate an adverse complication associated with virus infection or pathology. Adverse complications treatable in accordance with the invention include, for example, a cancer, an opportunistic disorder, immunodeficiency, autoimmunity, and a chronic illness.

Methods can be practiced by administering an antagonist prior to, substantially contemporaneously with or following exposure to or infection of the subject with virus. Methods can also be practiced by administering an antagonist prior to, substantially contemporaneously with or following virus reactivation from latency. Methods can be practiced by administering a plurality of antagonists, or in combination with other agents or treatment protocols.

Methods of increasing production of a Th1 cytokine in a subject with or at risk of a viral infection are provided. In one embodiment, a method includes administering to a subject an amount of an IL-10 Receptor (IL-10R) antagonist sufficient to increase Th1 cytokine production in the subject. Exemplary cytokines include, for example, interferon (IFN) gamma (e.g., by CD8+ T cells specific for a virus comprising the viral infection), TNF-alpha, IL-1alpha, IL-6 or IL-8.

Methods of decreasing IL-10 production in a subject with or at risk of a viral infection are provided. In one embodiment, a method includes administering to a subject an amount of an IL-10 Receptor (IL-10R) antagonist sufficient to decrease IL-10 production in the subject.

Methods of increasing numbers or activation of an immune cell in a subject with or at risk of a viral infection are provided. In one embodiment, a method includes administering to a subject an amount of an IL-10 Receptor (IL-10R) or an IL-10 antagonist sufficient to increase numbers or activation of the immune cell in the subject. Exemplary immune cells include T cells and dendritic cells (DC) (e.g., one or more of: CD4+, CD8+, B220+ and CD11c+ cells).

Methods of increasing or inducing an antiviral CD8+ T cell response in a subject with or at risk of a viral infection are provided. In one embodiment, a method includes administering to a subject an amount of an IL-10 Receptor (L-10R) or an IL-10 antagonist sufficient to increase or induce an antiviral CD8+ T cell response in the subject.

Methods of identifying and screening for candidate agents for treating a viral infection, reactivation and pathogenesis are provided. In one embodiment, a method includes contacting a test agent or sample containing a candidate agent with an IL-10R or an IL-10R ligand, and ascertaining the presence of binding between the test agent and IL-10R or L-10R ligand, or ascertaining the inhibition of IL-10R binding to ligand or IL-10 signaling, wherein binding, inhibition of IL-10R binding to ligand or IL-10 signaling identifies the test agent as a candidate agent for treating a viral infection, reactivation or pathogenesis. Test agents include, for example, polypeptides, such as polyclonal and monoclonal antibodies (e.g., mammalian, primatized, humanized and fully human); antibody fragments and subsequences of full length antibody having two heavy chains and two light chains (e.g., Fab, Fab', F(ab')$_2$, Fv, Fd, single-chain Fv (scFv), disulfide linked Fv, light chain variable (VL) and heavy chain variable (VH)); and small molecules. IL-10R or IL-10R ligand (e.g., IL-10) suitable for contact in vitro, ex vivo or in vivo include mammalian (e.g., human) IL-10R or IL-10R ligand (e.g., IL-10).

Kits including an IL-10 Receptor (IL-10R) antagonist or an IL-10 antagonist, and instructions for treating a subject (e.g., a mammal such as a human) having or at risk of having a viral infection, reactivation or pathogeneis are provided. Exemplary antagonists inhibit binding to an IL-10R ligand; inhibit IL-10 signaling or expression; and inhibit binding of a ligand (e.g., IL-10) to IL-10R.

Exemplary antagonists include small molecules, polypeptides and nucleic acids. Specific examples of polypeptides include monoclonal and polyclonal antibodies (e.g., mammalian, primatized, humanized and fully human), and dominant negative IL-10R ligand and soluble IL-10R. Antibodies include full length and fragments and subsequences of a full length antibody having two heavy chains and two light chains (e.g., Fab, Fab', F(ab')$_2$, Fv, Fd, single-chain Fv (scFv), disulfide linked Fv, light chain variable (VL) and heavy chain variable (VH)). Particular antibodies include, for example, antibodies having substantially the same binding affinity as an antibody selected from or produced by produced by 1B1.3a (BD Biosciences, Pharmingen Division, Cat. No. 550012) and 1B1.2 hybridoma (DNAX), and an anti-mouse IL-10R(R & D Systems, Cat. No. AF-474-NA). Additional particular examples include antibodies that competitively inhibit binding of an antibody selected from or produced by 1B1.3a (BD Biosciences, Pharmingen Division, Cat. No. 550012), 1B1.2 hybridoma (DNAX) and anti-mouse IL-10R(R & D Systems, Cat. No. AF-474-NA) to IL-10R. Specific examples of antibodies include 1B1.3a (BD Biosciences, Pharmingen Division, Cat. No. 550012), 1B1.2 hybridoma (DNAX) and anti-mouse IL-10R(R & D Systems, Cat. No. AF-474-NA).

DRAWING DESCRIPTIONS

FIG. 1. Shows data indicating that weight loss in mice treated with IL-10R antibody is reduced compared to mice treated with control antibody. Data is presented as difference in weight (g/mouse) compared to age-matched non-infected mice.

Figure 2:
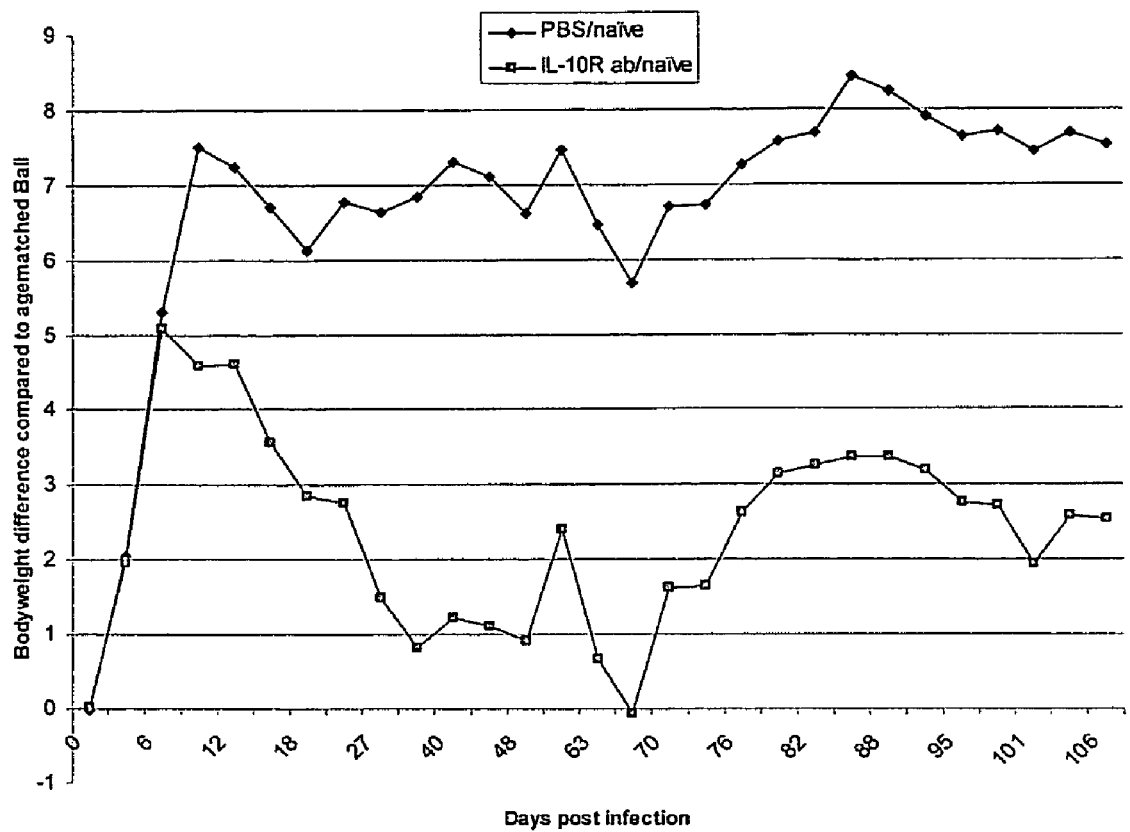

FIG. 2. Shows body weight of mice infected and following treatment with either 1) PBS or 2) IL-10R antibody per mouse.

Figure 3:
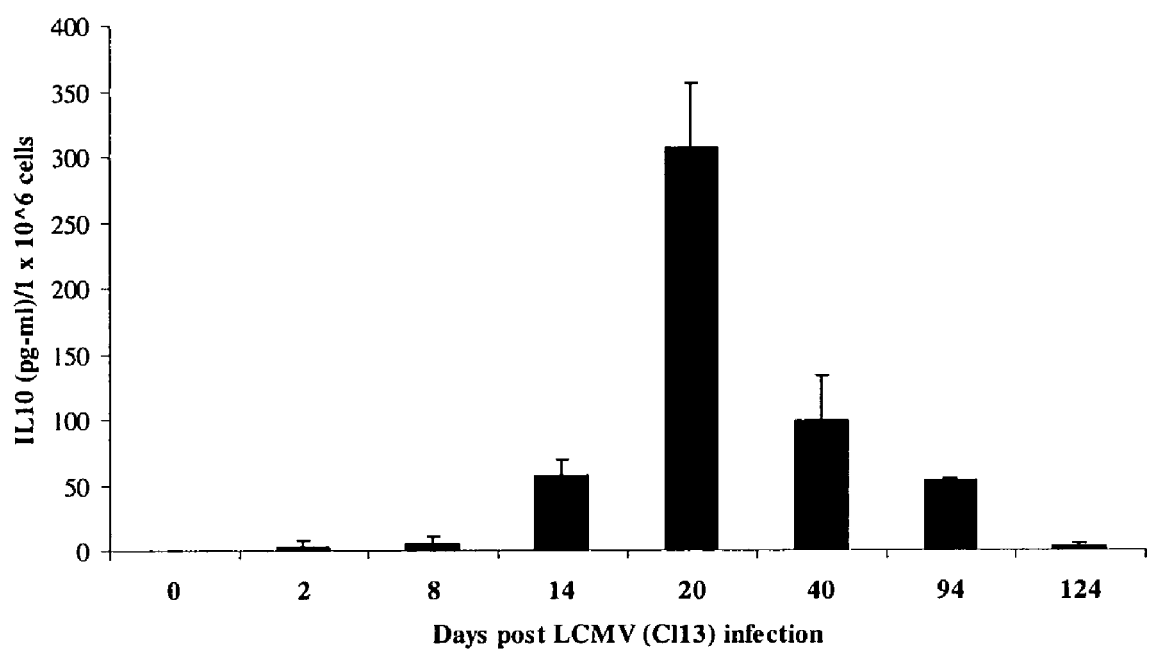

FIG. 3. Shows kinetics of IL-10 production during chronic LCMV infection. Data are represented as IL-10 (pg/ml) per $1 \times 10^6$ cells and are means of 3 mice per timepoint.

Figure 4:
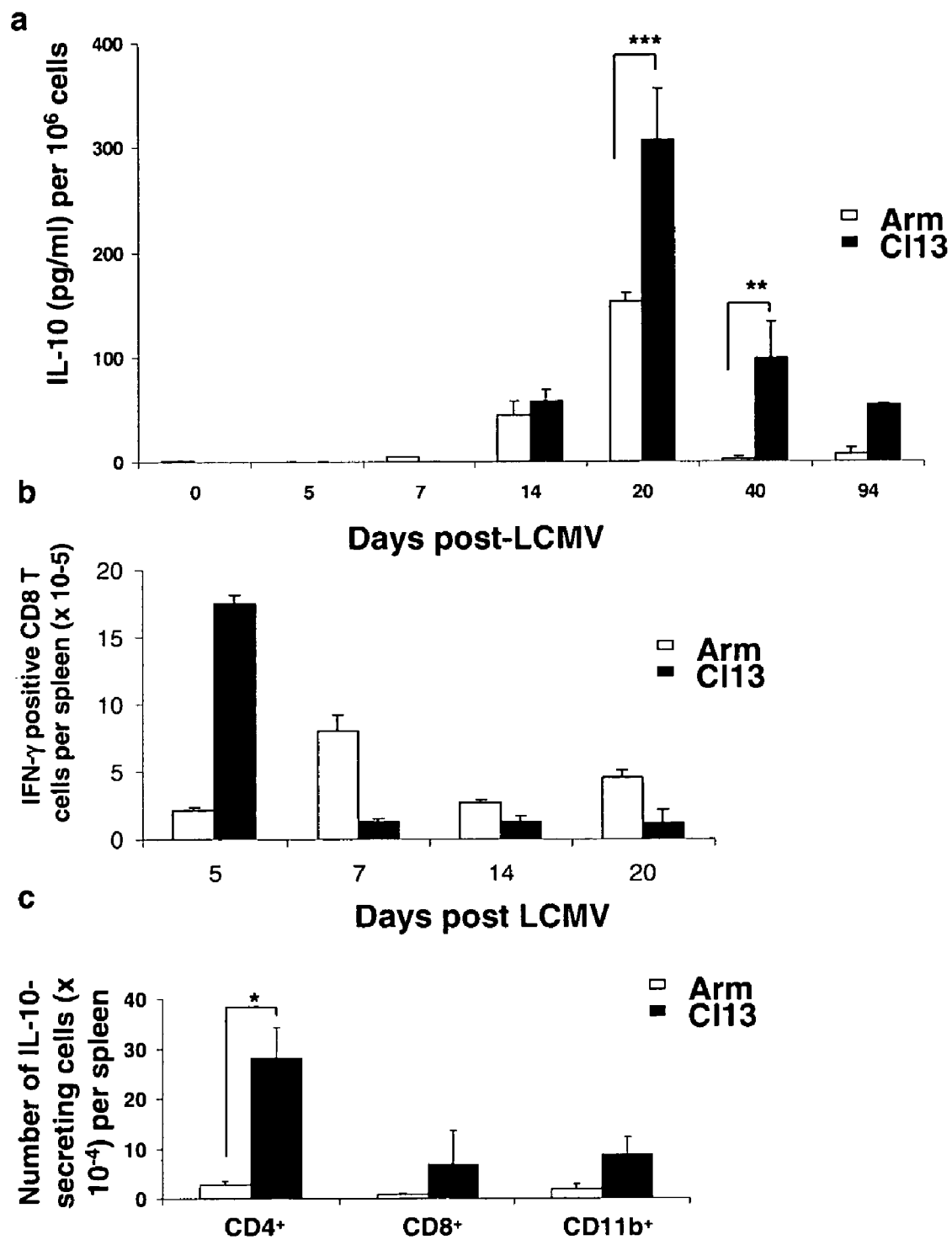

FIGS. 4 a-c. Shows kinetics and source of IL-10 and IFN-γ production in chronically-(LCMV Cl13) versus acutely-(LCMV Arm) infected mice. Mice infected with LCMV Cl13 (black bars), Arm (open bars). a. A peak of IL-10 was observed between day 14 and 20 post-Cl13 infection, which was not observed following LCMV Arm infection. b. IFN-γ production was detected as described in Example 1 after incubation of splenocytes with NP118 peptide and Brefeldin A and CD8+ T cell intracellular cytokine antibody staining followed by FACS analysis. The total number of cytokine positive cells was calculated by relating the percentage of cytokine positive cells total number of spleen cells. c. Splenocytes secreting IL-10 were isolated upon stimulation with LCMV infected macrophages. Increased numbers of CD4$^+$, CD8$^+$ and CD11 b$^+$ cells produced IL-10 in Cl13-infected mice compared to Arm-infected mice.

Figure 5:
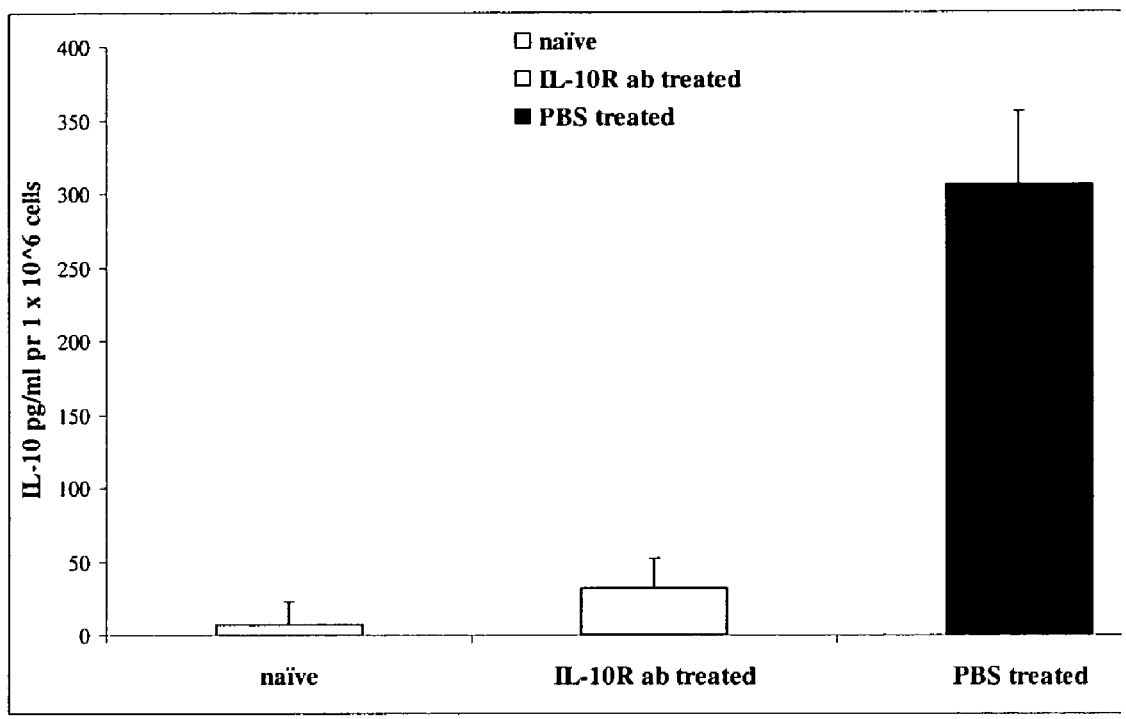

FIG. 5. Shows mice treated with IL-10R antibody have decreased levels of IL-10. Data are represented as IL-10 pg/ml per $1 \times 10^6$ cells and are an average of 3 mice per group.

Figure 6:
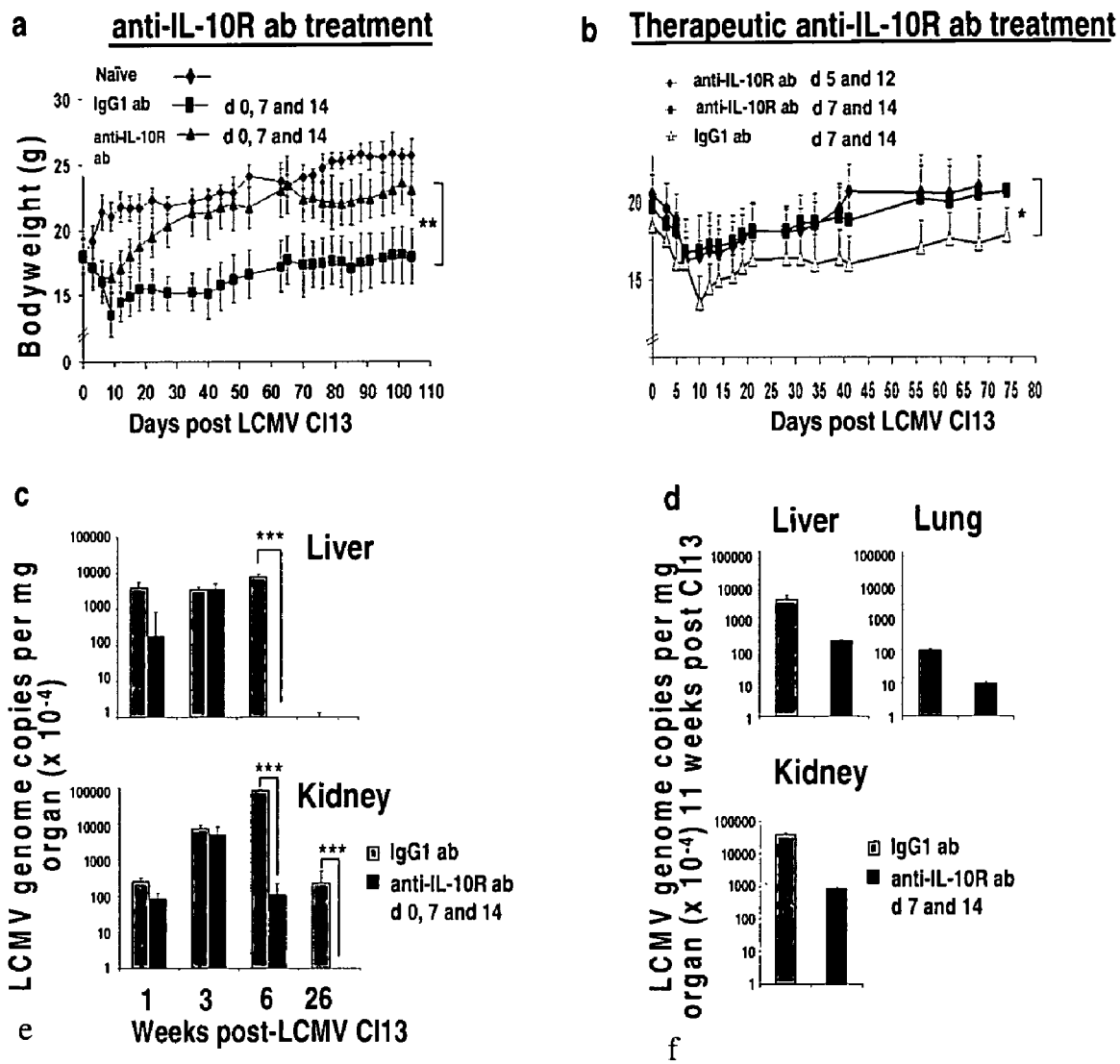

FIGS. 6 a-f. Shows increase in bodyweight after IL-10R antibody therapy of mice infected with LCMV Cl13 and reduction in viral titer after IL-10R antibody treatment of Cl13-infected mice. Cl13-infected mice treated with anti-IL 10R antibody or control antibody (a, c, and e) or therapeutically treated after establishment of LCMV Cl13 infection (b, d, and f).

Figure 7:
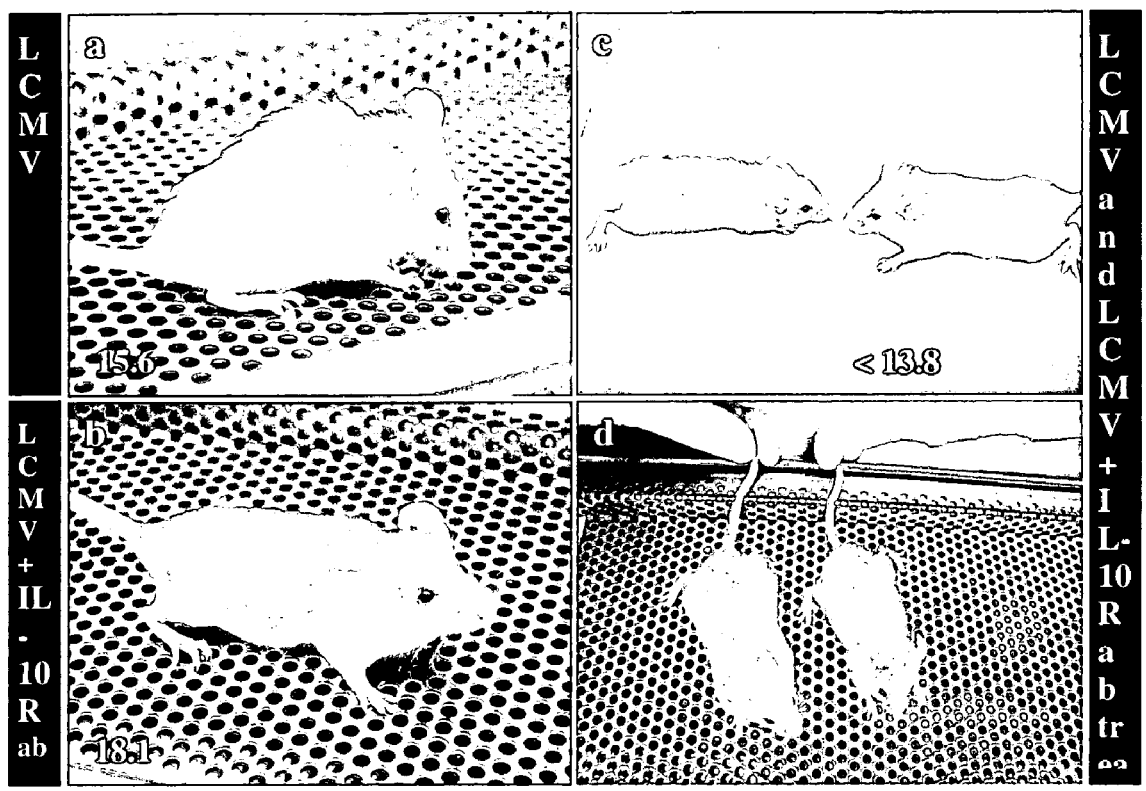

FIG. 7 *a-d*. Shows that mice treated with IL-10R antibody exhibit healthy phenotype. Mice infected with LCMV (Cl13) and treated with either PBS (a) or IL-10R antibody (b). Overall clinical appearance in mice treated with IL-10R antibody (b) was improved as reflected in increased bodyweight, healthy shiny coat, and increased physical activity compared to mice that did not receive IL-10R antibody (p=0.0037). Non-treated mice (a) had non-shiny, scruffy coat, and were less physically active.

Figure 8:
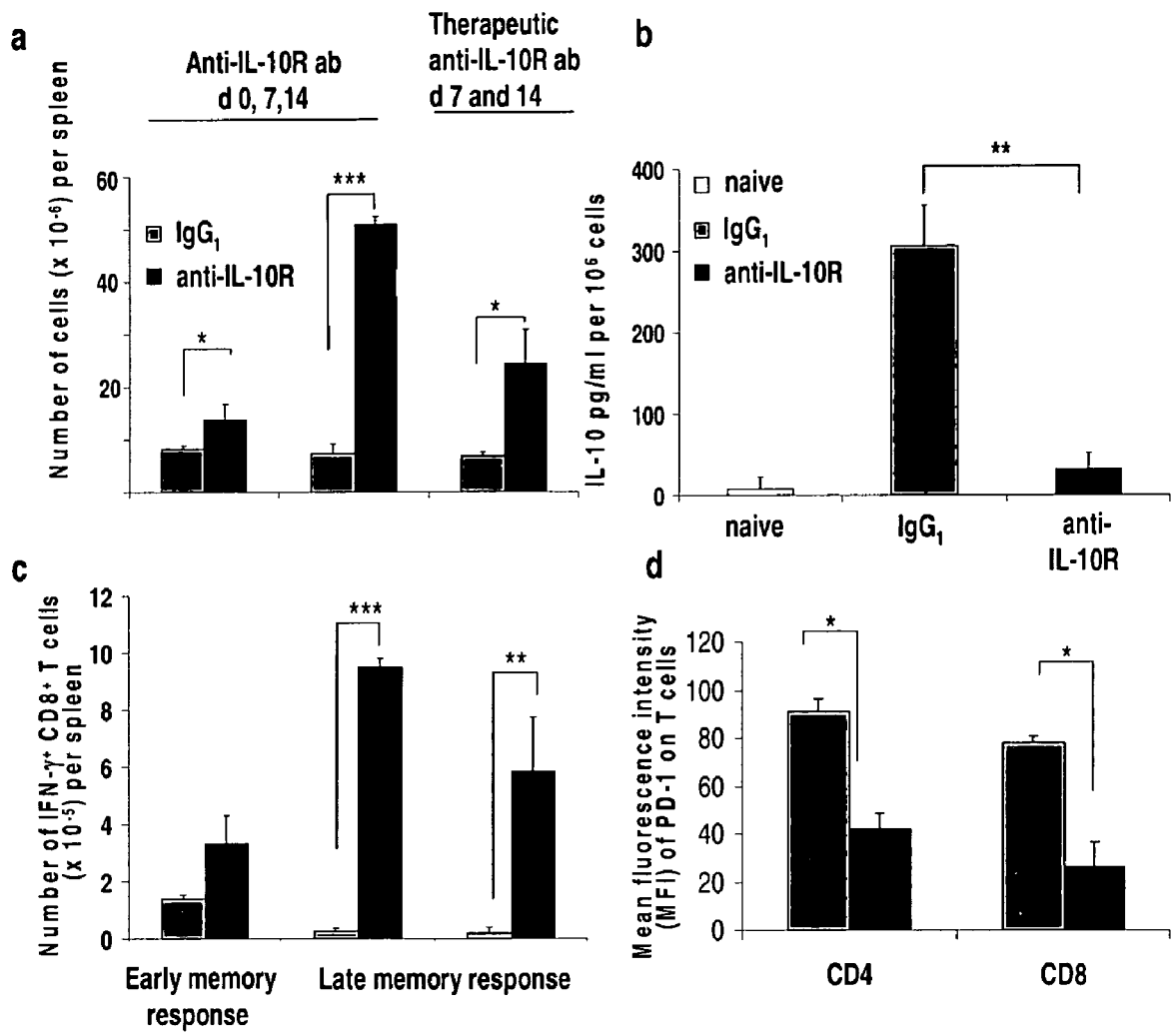

FIG. 8 *a-d*. Shows reduced IL-1 levels and re-establishment of anti-viral T cell responses after IL10R antibody treatment of mice infected with LCMV Cl13. a. Total numbers of cells per spleen was significantly increased post LCMV Cl13 infection. b. L-10 secretion was reduced in anti-IL-10R-treated but not saline or IgG1-injected mice. c. Intracellular cytokine staining after in vitro re-stimulation with LCMV-specific peptides showed an increase in the number of anti-viral IFN-γ producing CD8$^+$ T cells in the early and more pronounced in the late memory responses post IL-10R antibody treatment compared to control. d. Reduced PD-1 expression on CD4+ and CD8+ T cells after IL-10R antibody treatment. Results are shown as mean fluorescence intensity of PD-1 expressing T cells (n=4 per group).

Figure 9:
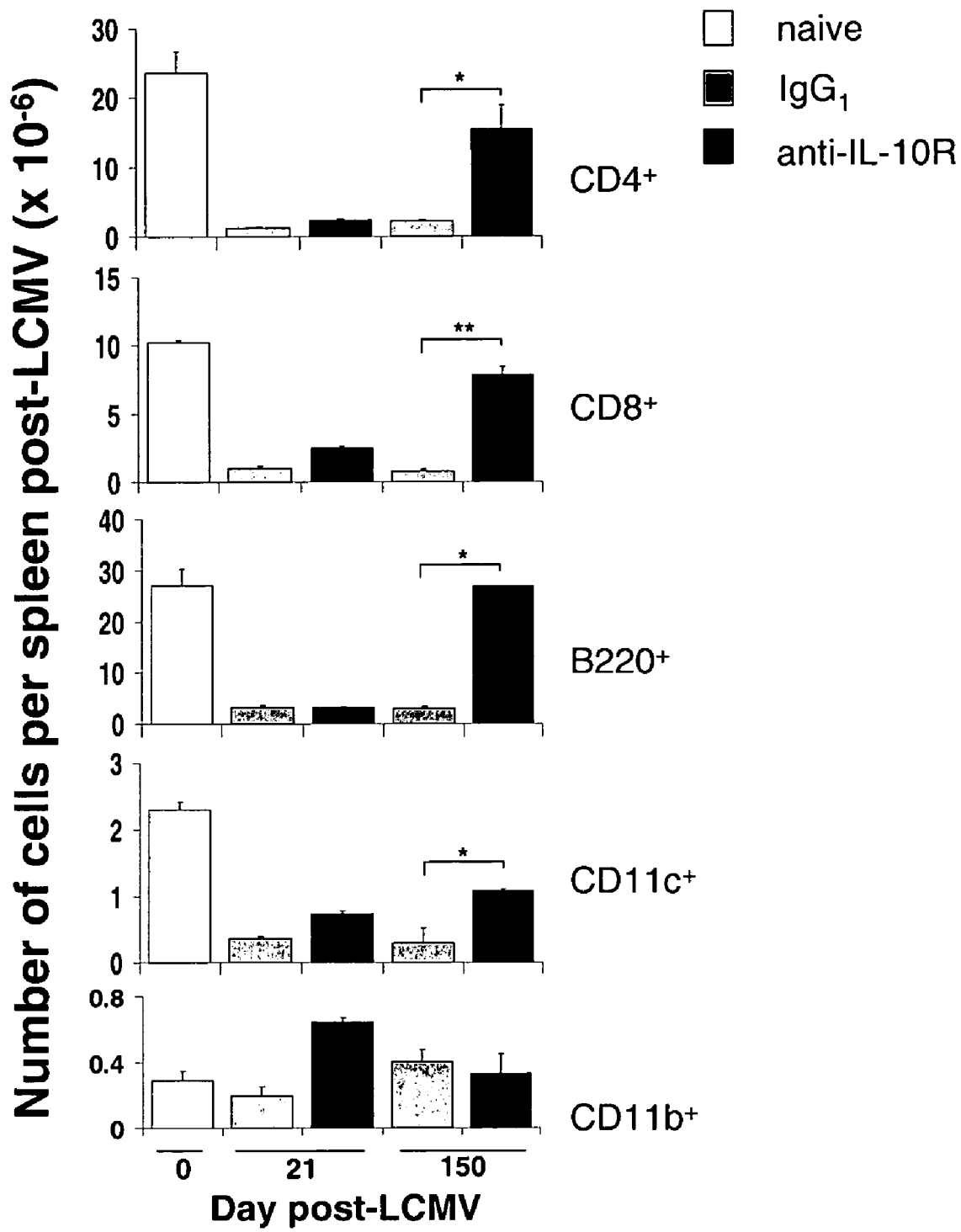

FIG. 9. Shows that anti-IL-10R treatment restores cell numbers in LCMV Cl13-infected mice. Treatment with IgG1 isotype control mAb (grey bars) or anti-IL-10R antibody (black bars) after infection monitored on different splenic cell subsets quantitatively. Age-matched uninfected mice were controls (open bars). Mean values for 3 to 5 individual mice are shown. The study is representative of three similar studies.

Figure 10:
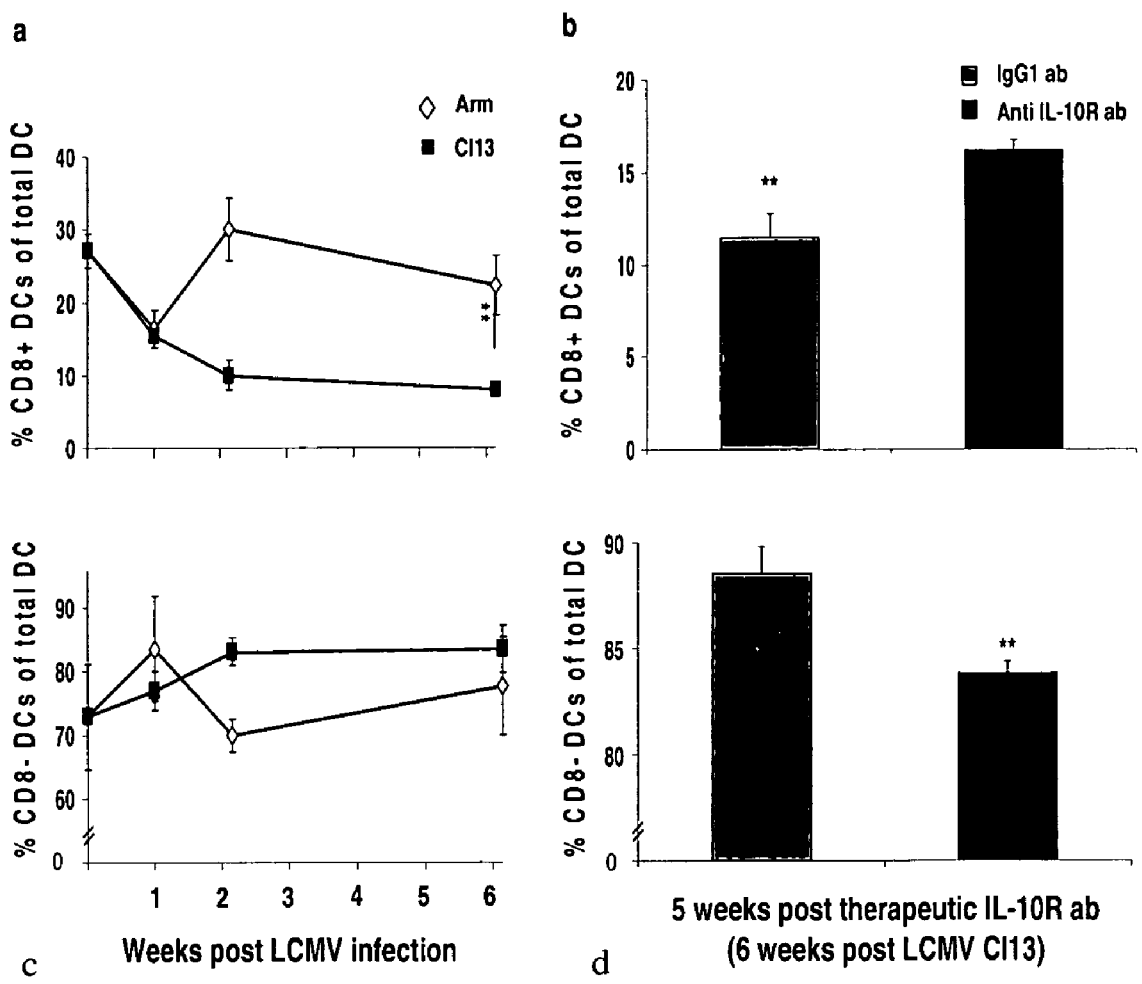

FIG. 10 *a-d*. Shows that loss of CD8α$^+$DCs after LCMV Cl13 infection can be restored by IL-10R antibody treatment. The ratio of CD8α$^-$ and CD8α$^+$ DC within the CD11c$^+$CD3$^-$ subset was determined following LCMV infection. a and c. Splenocytes isolated from LCMV Arm or LCMV Cl13 infected mice. b and d. CD8a$^-$ and CD8a$^+$subsets were quantified from LCMV Cl13 infected mice treated with IL-10R antibody or control IgG1 post infection as in Example 5 and the percentage of CD8a– and CD8a+ of the total CD11c+ CD3—population is shown. n=3-6 mice per group.

Figure 11:
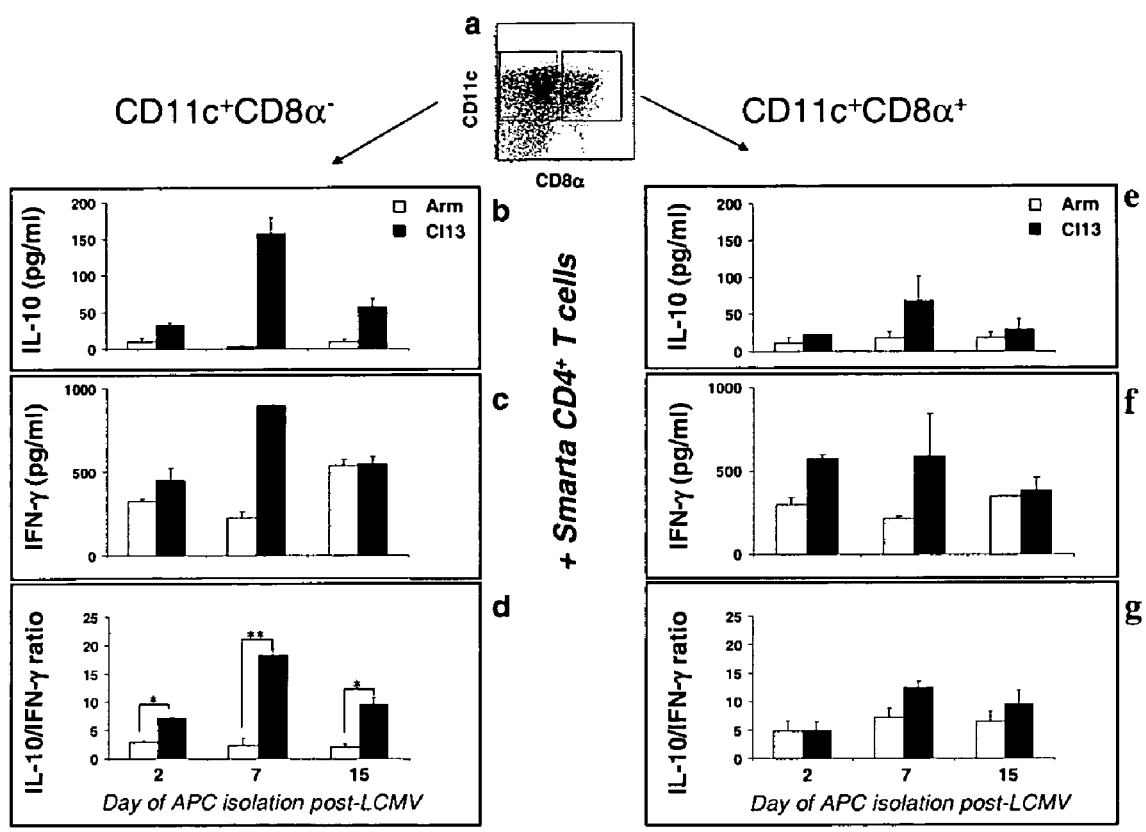

FIG. 11 *a-g*. Shows that CD8α$^+$ DCs induce IL-10 production in the early phase of Cl13 infection. a. CD11c+ DCs sorted into CD8α$^-$ and CD8α$^+$ subsets after infection with LCMV Cl13 or LCMV Arm. IL-10 (b and e), and IFN-γ (c and f) present in culture supernatant (pg/ml). No detectable IL-10 and IFN-γ were secreted by irradiated DCs alone. d and g. IL-10/IFN-γ ratio reflecting the trend toward IL-10 production by the stimulated CD4$^+$ T cells.

DETAILED DESCRIPTION

The invention provides, among other things, compositions and methods embodiments for treating a subject for a viral infection, prophylactically or therapeutically. In one embodiment, a method includes contacting or administering to a subject an amount of an IL-10 Receptor (IL-10R) antagonist sufficient to treat the subject. In another embodiment, a method includes contacting or administering to a subject an amount of an IL-10R ligand (e.g., IL-10) antagonist sufficient to treat the subject.

The term "antagonist," when used in reference to IL-10R or IL-10R ligand (e.g., IL-10), means a compound or agent that directly or indirectly reduces, inhibits, decreases, delays, halts, eliminates or prevents an activity (function) or expression of IL-10R or IL-10R ligand (e.g., IL-10), at least transiently (e.g., for minutes, hours, days, months, or longer). Antagonists therefore include compounds and agents that modulate IL-10R or IL-10R ligand (e.g., IL-10) protein or nucleic acid expression or activity. For example, compounds and agents that directly or indirectly bind to IL-10R or IL-10R ligand (e.g., IL-10) protein or nucleic acid, thereby reducing, inhibiting, decreasing, delaying, halting, eliminating or preventing IL-10R or IL-10R ligand (e.g., IL-10) activity or expression are considered antagonists.

To bind or binding means direct physical contact, or indirect, by binding to an intermediary. A non-limiting example of an intermediary is a molecule that binds to IL-10R or IL-10R ligand (e.g., IL-10) to which an antagonist binds. Thus, an antagonist may not directly physically contact IL-10R or IL-10R ligand (e.g., IL-10), but may bind to an intermediary molecule which, in turn, contacts IL-10R or IL-10R ligand (e.g., IL-10). Antagonists therefore include compounds and agents that function to decrease, reduce, inhibit, delay, halt, eliminate or prevent an activity or expression of IL-10R or IL-10R ligand (e.g., IL-10) by direct binding or through binding to an intermediary.

IL-10R is a cell surface receptor composed of two polypeptide chains, denoted alpha and beta chains. Both alpha and beta chains of IL-10R are members of the class II cytokine receptor family. The extracellular domain of IL-10R alpha chain can mediate binding to ligand (e.g., IL-10) but it has been reported that the beta chain is required for IL-10 signaling (Kotenko et al., *EMBO J* 16:5894 (1997)). It is believed that signaling and subsequent biological activities are induced upon formation of IL-10/IL-10R complex. For example, IL-10 has been reported to stimulate tyrosine phosphorylation of the signal transducers and activators of transcription, STAT1 alpha and STAT3, and Jak1 and Tyk-2 (Finbloom, D. S. and Winestock, K. D., *J Immunol* 155:1079 (1995)). Antagonists therefore include compounds and agents that modulate (e.g., by binding) IL-10R alpha chain or beta chain expression or activity.

Exemplary non-limiting classes of compounds and agents that modulate or bind to IL-10R or IL-10R ligand (e.g., IL-10) protein or nucleic acid thereby antagonizing expression or activity, include polypeptides, nucleic acid and small molecules. Additional non-limiting examples include antibodies (e.g., with two heavy chains and two light chains). Antibodies can bind to either extracellular domain of IL-10R alpha or beta chains.

Antibodies may be mammalian, such as a primate or fully or partially human, e.g., humanized or primatized antibody. Antibodies include monoclonal, polyclonal and mixtures thereof. Antibodies further include functional (e.g., antigen binding) subsequences (fragments) that bind to IL-10R or IL-10R ligand (e.g., IL-10), such as Fab, Fab', F(ab')$_2$, Fv, Fd, single-chain Fv (scFv), disulfide linked Fv, light chain variable (VL) and heavy chain variable (VH) forms. Specific non-limiting examples of IL-10R antibodies include 1B1.3a (BD Biosciences, Pharmingen Division, Cat. No. 550012), and 1B1.2 hybridoma (DNAX) producing antibody, and anti-mouse IL-10R(R & D Systems, Cat. No. AF-474-NA).

Additional non-limiting examples of compounds and agents that bind to IL-10R or IL-10R ligand (e.g., IL-10) and modulate expression or activity (function) include, for example, nucleic acid (e.g., antisense nucleic acid or interfering RNA, or RNAi) that binds to IL-10R or IL-10R ligand (e.g., IL-10) nucleic acid, at least transiently, thereby reducing expression or activity of IL-10R or IL-10R ligand (e.g., IL-10). Further non-limiting examples include a dominant negative IL-10R or IL-10R ligand (e.g., IL-10) polypeptide, or a soluble IL-10R polypeptide. Such types of IL-10R ligand (e.g., dominant negative) or soluble IL-10R polypeptide bind to or occupy the endogenous IL-10R or ligand (e.g., IL-10) thereby inhibiting or preventing the ability of endogenous IL-10R or ligand (e.g., IL-10) to bind to IL-10 ligand (e.g., IL-10) or IL-10R and confer signaling in a cell, in vitro, ex vivo or in vivo.

The expression or an activity of IL-10R or IL-10R ligand (e.g., IL-10) can be monitored, for example, using protein detection methods (e.g. immunoassays), measuring transcript (e.g., RNA) levels or stability, and measuring an activity, such as a biological activity, e.g., signaling of ligand-bound IL-10R complex. A particular example of a biological activity resulting from signaling of ligand-bound IL-10R complex is activation of signal transducer and activator of transcription 3 (STAT3) or signal transducer and activator of transcription 1 (STAT1) in vitro, such as in a responder cell line that expresses STAT3 or STAT1.

Methods embodiments include, for example, methods of contact or administration in vitro (in solution, in solid phase or in culture), ex vivo and in vivo, with an antagonist of IL-10R or IL-10R ligand (e.g., IL-10) expression or activity. The term "contact" means direct or indirect binding or interaction between two or more entities (e.g., between a cell and a compound or agent (e.g., an antibody) that binds to IL-10R or IL-10R ligand (e.g., IL-10), or between IL-10R or IL-10R ligand (e.g., IL-10), and a compound or agent (e.g., an antibody) that binds to IL-10R or IL-10R ligand (e.g., IL-10). Contacting as used herein includes in solution, in solid phase, in culture, in vitro, ex vivo, in a cell and in vivo. Contacting in vivo can be referred to as "administering," or "administration."

The term "culture" or "cell culture" refers to cells grown or maintained in an in vitro or artificial environment. A "cell culture" is a generic term that can also be used to encompass individual clonal cells, but also groups or collections of cells, such as immune cells, feeder layer cells, etc. A "cell culture medium" or "culture medium" is used interchangeably to refer to a nutritive composition intended to maintain viability or promote growth of cells.

The term "treatment" refers to contact ex vivo, or in vivo, or administration to a subject. Treatment typically involves administration to a subject with or at risk of a viral infection, or a subject that exhibits one or more physiological conditions, disorders, illness, diseases or symptoms caused by or associated with an acute or chronic viral infection or reactivation from latency. Thus, methods of the invention include administering an IL-10R or IL-10R ligand (e.g., IL-10) antagonist prior to, substantially contemporaneously with or following exposure to or infection of the subject with virus; and administering an IL-10R or IL-10R ligand (e.g., IL-10) antagonist prior to, substantially contemporaneously with or following virus reactivation from latency.

A "therapeutic" treatment method means that the method is practiced on a subject with an acute or chronic viral infection, which causes one or more physiological conditions, disorders, illness, diseases or symptoms. A therapeutic treatment also refers to a method practiced on a subject suffering from viral reactivation from latency (e.g., for herpesvirus).

"Prophylaxis" and grammatical variations thereof refer to contact, administration or in vivo delivery to a subject prior to a viral infection or prior to viral reactivation from latency. In situations where it is not known if a subject has been exposed to or infected with a virus, administration or ex vivo or in vivo delivery of an antagonist of IL-10R or IL-10R ligand (e.g., IL-10) to a subject prior to manifestation or onset of one or more physiological conditions, disorders, illness, diseases or symptoms caused by or associated with a viral infection. In such a method, the effect of contact with, administration, ex vivo or in vivo delivery of an antagonist of IL-10R or IL-10R ligand (e.g., IL-10) can be to eliminate, prevent, inhibit, decrease or reduce the probability of or susceptibility of a viral infection, reactivation from latency or one or more physiological conditions, disorders, illness, diseases or symptoms caused by or associated with a viral infection or viral reactivation from latency.

Methods embodiments, including, for example, treatment methods, are applicable to treating any acute or chronic viral infection, prophylactically or therapeutically, or a physiological condition, disorder, illness, disease and symptom caused by or associated with an acute or chronic viral infection, treatable by administering or contact with an antagonist of IL-10R or IL-10R ligand (e.g., IL-10) expression or activity. The invention compositions and methods are therefore applicable to viruses generally. Virus infection treatable in accordance with an antagonist of IL-10R or IL-10R ligand (e.g., IL-10) may provide one or more objective or subjective benefits to a subject. It is recognized that not all subjects will exhibit a benefit, nor even a majority of subjects in a given group or population, since some subjects will exhibit a greater or less response to treatment than other subjects.

Non-limiting virus classes include herpesvirus (HV), hepatitis virus, immunodeficiency virus, flavivirus, papilloma virus (PV), polyoma virus, rhabdovirus, myxovirus, arenavirus, coronavirus, poxvirus, adenovirus, reovirus, picornavirus, togavirus, bunyavirus, parvovirus, and retrovirus.

For herpesvirus (HV), specific examples include α-herpesvirus, β-herpesvirus, γ-herpesvirus, Epstein Bar Virus (EBV), Cytomegalovirus (CMV), varicella zoster virus (VZV/HHV-3), and human herpes virus 1, 2, 4, 5, 6, 7 and 8 (HHV-8, Kaposi's sarcoma-associated virus). Following a primary or initial infection, the virus establishes "latency" in the host subject which allows the virus to evade immune clearance and remain in the host subject, and infection is lifelong. During latency, HV does not typically cause illness or symptoms, there is little if any viral replication and the subject is not infectious or contagious. A "latent infection" may occur in a different cell type than that of the initial/primary HIV infection. "Reactivation," when used in reference to HV, means activation of HV in the host subject following a period of latency. Reactivation is associated with increased HIV replication and proliferation in the infected host subject, who becomes infectious and contagious again, with manifestation of one or more HV physiological conditions, disorders, illness, diseases or symptoms. Such physiological conditions, disorders, illness, diseases or symptoms caused by or associated with HV reactivation may or may not be of the same type, severity, frequency or duration as those caused by or associated with initial infection.

For hepatitis virus, specific examples include hepatitis A, B, C, D, E and G.

For immunodeficiency virus, specific examples include human immunodeficiency virus (HIV). HIV includes any strain or isolate or subtype or species of HIV, or combination of strains or isolates or subtypes or species of HIV. Particular examples are HIV-1, HIV-2 and HIV-3. Specific non-limiting examples of HIV-1 groups include Groups M, N and O. Additional examples are drug resistant HIV types, groups, subtypes or isolates. Specific non-limiting examples of HIV-1 subtypes include A, B, A/B, A/E, A/G, C, D, F, G, H, J and K subtypes, and mixtures thereof.

For papilloma virus (PV), a specific example includes human papilloma virus (HPV). Exemplary human papilloma virus is HPV strain 1, 6, 11, 16, 18, 30, 31, 42, 43, 44, 45, 51, 52 and 54.

For polyoma virus, specific examples include BK virus (BKV) and JC virus (JCV).

For rhabdovirus, specific examples include rabies virus and vesiculovirus.

For myxovirus, specific examples include paramyxovirus and orthomyxovirus. Exemplary paramyxovirus are measles, mumps, pneumovirus and respiratory syncytial virus (RSV). Exemplary orthomyxovirus include pathogenic influenza virus (e.g., influenza A, influenza B and influenza C). Specific exemplary pathogenic influenza virus include A/PR/34, A/HK8/68, A/HK/1/68, H1N1, H2N2, H3N2, H5N1, H9N2, H2N1, H4N6, H6N2, H7N2, H7N3, H4N8, H5N2, H2N3, H11N9, H3N8, H1N2, H11N2, H11N9, H7N7, H2N3, H6N1, H13N6, H7N1, H11N1, H7N2 and H5N3.

For arenavirus, specific examples include lymphocytic choriomeningitis virus (LCMV), Junin virus, Lassa virus, Guanarito virus, Sabia virus and Machupo virus.

For coronavirus, specific examples include viruses that cause the common cold or severe acute respiratory syndrome (SARS).

For poxvirus, specific examples include vaccinia virus, Molluscum contagiosum, variola major or variola minor smallpox virus, cow pox, camel pox, sheep pox and monkey pox. Particular non-limiting examples of variola major or variola minor smallpox virus include extracellular enveloped virus (EEV), intracellular mature virus (IMV) and cell-associated virus (CEV) forms. Additional exemplary poxvirus include, for example, goatpox, swinepox, buffalopox, sealpox, canarypox, raccoonpox, pigeonpox and rabbitpox.

For flavivirus, specific examples include Yellow Fever virus, Dengue virus, Japanese Encephalitis and West Nile viruses.

For adenovirus, specific examples include adenoviral infection of bronchi, lung, stomach, intestine (gastroenteritis), eye (conjunctivitis), bladder (cystitis) and skin.

For reovirus, specific examples include rotavirus, cypovirus and orbivirus.

For picornavirus, specific examples include rhinovirus, apthovirus, hepatovirus, enterovirus such as poliovirus and cardiovirus. Exemplary rhinoviruses cause the common cold.

For togavirus, specific examples include alphavirus, sindbus virus and rubellavirus.

For bunyavirus, specific examples include hantavirus, phlebovirus and nairovirus.

For retrovirus, specific examples include alpha, beta, delta, gamma, epsilon, lentivirus, oncovirus such as human T-cell leukemia virus (HTLV), immunodeficiency virus such as HIV, and spumavirus. Exemplary lentivirus are immunodeficiency virus, such as bovine, porcine, equine, canine, feline and primate lentivirus. Exemplary HTLV include HTLV-1 and HTLV-2.

Treatment methods are intended to provide an objective effect or benefit, for example, an improvement in the underlying viral infection. Methods of treatment embodiments therefore include, for example, reducing virus titer, amount of a virus protein or an amount of a virus nucleic acid; reducing or inhibiting increases in virus titer, virus proliferation, synthesis of a virus protein or a virus nucleic acid, one or more symptoms of virus infection; increase or stimulate virus clearance; inhibit or reduce virus infection; inhibit or reduce virus reactivation from latency. Methods of treatment embodiments therefore also include, for example, providing a subject with partial or complete protection against infection or pathogenesis (e.g., illness), virus reactivation from latency, or a physiological condition, disorder, illness, disease or symptom associated with or caused by the viral infection or reactivation from latency. Additional non-limiting methods include reducing, decreasing, amounts of, or inhibiting, delaying or preventing increases in, virus titer or load, virus protein or a virus nucleic acid, or virus proliferation or replication, or progression of the viral infection or reactivation from latency.

Treatment methods also included are methods that provide an objective or subjective (perceived) effect or benefit in an associated physiological condition, disorder, illness, disease or symptom. Methods embodiments can therefore result in a beneficial effect or improvement in a subjects' physiological or psychological condition, disorder, illness, disease or symptom.

Methods providing a beneficial effect to a subject, for example, reducing, decreasing, inhibiting, delaying, ameliorating or preventing onset, progression, severity, duration, frequency or probability of a viral infection/reactivation or one or more conditions, disorders, illness, diseases, symptoms or complications associated with or caused by a viral infection/reactivation; reducing, decreasing, inhibiting, delaying or preventing increases in virus titer, viral load, replication, proliferation, or an amount of a viral protein or viral nucleic acid. Stabilizing the underlying viral infection/reactivation, or a condition, disorder, illness, disease, symptom or complication thereof (i.e., preventing, inhibiting or delaying a worsening or progression of the infection/reactivation or a condition, disorder, illness, disease, symptom or complication caused by or associated with viral infection/reactivation), or delaying or inhibiting progression of the underlying viral infection/reactivation or a condition, disorder, illness, disease, symptom or complication caused by or associated with viral infection/reactivation, are also included in various methods embodiments.

As used herein, the term "associated with," when used in reference to a relationship between a viral infection/reactivation, and psychological or physiological condition, disorder, illness, disease or symptom, means that the psychological or physiological condition, disorder, illness, disease or symptom is an effect or consequence of the infection/reactivation, e.g., an adverse complication. A psychological or physiological condition, disorder, illness, disease or symptom present in a subject may therefore be a direct result of a viral infection/reactivation, or may be an indirect result of a viral infection/reactivation, such as a secondary or subsequent effect or consequence of the infection/reactivation. Such effects and consequences are considered to be associated with a viral infection/reactivation.

Methods of treatment embodiments therefore further include treating one or more symptoms, pathologies, or side effects of a psychological or physiological condition, disorder, illness, disease, symptom or an effect or consequence of the viral infection/reactivation or pathogenesis to any degree or for any duration of time (hours, days, weeks, months, years, or cure). Non-limiting examples of treatment methods embodiments include reducing, decreasing, inhibiting, delaying or preventing onset, severity, duration, progression, frequency or probability of a viral infection/reactivation, or one or more psychological or physiological conditions, disorders, illness, diseases and symptoms associated with or caused by a viral infection/reactivation; improving one or more symptoms associated with a virus infection/reactivation or pathology; reducing or ameliorating an adverse complication associated with a virus infection/reactivation or pathology; and accelerating, facilitating or hastening recovery of a subject from a viral infection/reactivation or one or more associated psychological or physiological conditions, disorders, illness, diseases, symptoms or complications.

Additional non-limiting examples of a beneficial effect or improvement include reducing or decreasing probability, susceptibility or likelihood that the subject so treated will manifest one or more physiological conditions, disorders, illness, diseases, symptoms or complications of the viral infection/reactivation. Still further physiological conditions, disorders, illness, diseases, symptoms or complications associated with viral infection/reactivation whose occurrence, frequency, severity, progression, or duration can be reduced, decreased or prevented are known in the art. A beneficial effect or improvement can also include hastening or accelerating recovery from viral infection/reactivation.

Exemplary adverse complications include cancer, immunodeficiency, autoimmunity, increased susceptibility to opportunistic disorders (cancers/tumors) or infections (bacterial, viral, parasite, fungal) or an acute or chronic illness. Additional physiological or psychological conditions, disorders, illness, diseases, symptoms or complications caused by or associated with the viral infection/reactivation are set forth herein and are known in the art and, therefore, improvements in these and other physiological conditions, disorders, illness, diseases, symptoms and complications are included in the various treatment embodiments.

For HIV (e.g., HIV-1, HIV-2 and HIV-3), non-limiting examples of physiological conditions, disorders, illness, diseases and symptoms caused by or associated with HIV infection or pathogenesis, whose onset, progression, severity, frequency, duration or probability can be reduced, decreased, inhibited, delayed ameliorated or prevented include, for example, opportunistic disorders such as bacterial, viral (re-activation of virus from latency such as herpesvirus), fungal, and parasitic infections, cancers and tumors which are due in part to weakened immune system of the infected subject. Such treatment embodiments can therefore target one or more of the underlying infection, an associated opportunistic disorder, or a physiological condition, disorder, illness, disease or symptom associated with HIV infection or an associated opportunistic disorder.

Non-limiting examples of opportunistic disorders include Candidiasis of bronchi, trachea, lungs or esophagus, cervical cancer, Coccidioidomycosis, Cryptococcosis, Cryptosporidiosis, Bacillary Angiomatosis, Cytomegalovirus (CMV), Cytomegalovirus retinitis, Herpes virus, Hepatitis virus, papilloma virus, Histoplasmosis, Isosporiasis, Kaposi's sarcoma, Burkitt's lymphoma, immunoblastic lymphoma, LCMV, *Mycobacterium avium, Mycobacterium tuberculosis, Pneumocystis carinii*, Pneumonia, progressive multifocal leukoencephalopathy (PML), Salmonelosis, Toxoplasmosis, Wasting syndrome and Lymphoid interstitial pneumonia/pulmonary lymphoid type.

Additional non-limiting examples of physiological conditions, disorders, illness, diseases and symptoms caused by or associated with HIV infection or pathogenesis, whose onset, progression, severity, frequency, duration or probability can be reduced, decreased, inhibited, delayed ameliorated or prevented include, for example, fever, fatigue, headache, sore throat, swollen lymph nodes, weight loss, diarrhea, rash, boils, warts, thrush, shingles, chronic or acute pelvic inflammatory disease (PID), dry cough, shortness of breath, bruising, bleeding, numbness or paralysis, muscle weakness, an opportunistic disorder, nerve damage, encephalopathy, dementia and death.

Yet additional non-limiting examples of physiological conditions, disorders, illness, diseases and symptoms caused by or associated with HIV infection or pathogenesis include reduced CD4+ or CD8+ cells, reduced or deficient CTL response. For example, CD4+ cell numbers less than 400 cells/cubic millimeter (mm3) blood, e.g., 300 or 200 cells/cubic millimeter (mm3) blood are typically found in HIV+ AIDS patients.

Methods embodiments therefore also include, for example, an improvement in any of fever, fatigue, headache, sore throat, swollen lymph nodes, weight loss, diarrhea, rash, boils, warts, thrush, shingles, chronic or acute pelvic inflammatory disease (PID), dry cough, shortness of breath, bruising, bleeding, numbness or paralysis, muscle weakness, opportunistic infections disorders and diseases, nerve damage, encephalopathy, dementia, and death; increased CD8+ or CD4+ (e.g., greater than 600, 500, 400, 300 or 200 cells/cubic millimeter (mm3) blood) T cell numbers; increased activity or percentages of CD8+ or CD4+ T cell numbers relative to all lymphocytes; stabilizing the percentage of CD8+ or CD4+ T cells relative to other lymphocytes (e.g., greater than 40%, 25%, or 15%); an improved or increased cytotolytic T lymphocyte (CTL) response against HIV or opportunistic disorders, etc.

Herpesvirus infection can be an initial or primary infection or result from reactivation from latency. In immunocompetent subjects, initial/primary infection is usually either asymptomatic or causes mild pathogenesis or symptoms; only a small proportion of subjects develop more severe clinical illness. Primary infection is self-limiting in immunocompetent patients. In contrast, primary HIV infection in immunocompromised subjects (e.g., immunosuppressant treatment, HIV+, newborns/neonates, pregnant, elderly subjects, etc.), can result in severe symptoms and even be fatal. Symptoms of HIV infection may therefore vary depending upon whether the infection is a primary infection or reactivation from latency and whether the subject is immune-competent or not. For example, VZV/HHV-3 causes chickenpox in a primary infection and shingles upon reactivation. Reactivation can be milder (e.g., asymptomatic) than an initial HIV infection/pathogenesis, in which case it will not always be obvious whether a host subject is in a latent or reactivated state. In immunocompetent host subject's reactivation is typically mild, whereas in immunocompromised host subjects, symptoms associated with or caused by reactivation can be severe and lead to death. Accordingly, HIV infection/reactivation can cause different clinical symptoms or pathologies with varying duration, severity and frequency.

For herpesvirus (e.g., α-herpesvirus, β-herpesvirus, γ-herpesvirus, EBV, CMV, VZV/HHV-3, HHV 1, 2, 4, 5, 6, 7 and 8), non-limiting examples of physiological conditions, disorders, illness, diseases and symptoms caused by or associated with HIV infection, reactivation or pathogenesis, whose onset, progression, severity, frequency, duration or probability can be reduced, decreased inhibited, delayed, ameliorated or prevented include, for example, lesions, ulcers, canker sore, cold sore, rash, boils, Gingivostomatitis, Herpetic whitlow Traumatic herpes (herpes gladiatorum), Eczema herpeticum, fever, fatigue, headache, sore throat, swollen lymph nodes, pneumonitis, pneumonia, hepatitis, meningitis, myelitis, Encephalitis, keratitis, Genital herpes, esophagitis, dysphasia, hemiparesis, coma, shingles, chicken pox, mononucleosis, chronic or acute pelvic inflammatory disease (PID), proctitis, colitis, nerve damage and death. A symptom of HV reactivation is the appearance of "cold sores" around mucosal areas (e.g., mouth, lips, tongue, genitalia, anus, rectum, etc.).

For hepatitis (e.g., hepatitis A, B, C, D, E and G), non-limiting examples of physiological conditions, disorders, illness, diseases and symptoms caused by or associated with hepatitis infection, reactivation or pathogenesis, whose onset, progression, severity, frequency, duration or probability can be reduced, decreased inhibited, delayed, ameliorated or prevented include, for example, loss of appetite, fatigue, fever, muscle or joint aches, nausea, vomiting, abdominal discomfort or pain, diarrhea, dark urine, light-colored stool, jaundice and itching.

For papilloma virus (e.g., HPV strain 1, 6, 11, 16, 18, 30, 31, 42, 43, 44, 45, 51, 52 and 54), non-limiting examples of physiological conditions, disorders, illness, diseases and symptoms caused by or associated with PV infection, reactivation or pathogenesis, whose onset, progression, severity, frequency, duration or probability can be reduced, decreased, inhibited, delayed ameliorated or prevented include, for example, warts on skin or in the genital area or cervix, and cell dysplasia, which can lead to either benign or malignant hyperplasia (cancer/tumor).

For polyoma virus (e.g., BK virus (BKV) and JC virus (JCV)), non-limiting examples of physiological conditions, disorders, illness, diseases and symptoms caused by or associated with polyoma virus infection, reactivation or pathogenesis, whose onset, progression, severity, frequency, duration or probability can be reduced, decreased, inhibited, delayed ameliorated or prevented include, for example, increased serum creatinine, hydronephrosis, progressive multifocal leukoencephalopathy (PML), hemorrhagic cystitis, nephritis, organ and transplant failure.

For rhabdovirus (e.g., rabies virus and vesiculovirus), non-limiting examples of physiological conditions, disorders, illness, diseases and symptoms caused by or associated with rhabdovirus infection, reactivation or pathogenesis, whose onset, progression, severity, frequency, duration or probability can be reduced, decreased, inhibited, delayed ameliorated or prevented include, for example, fever, headache, loss of appetite, convulsions, excessive flow of tears and saliva, insomnia, anxiety, muscle spasms triggered by swallowing, mania, coma and death.

For myxovirus (e.g., paramyxovirus and orthomyoxovirus such as measles, mumps, pneumovirus, RSV and influenza virus), physiological conditions, disorders, illness, diseases and symptoms caused by or associated with myxovirus infection, reactivation or pathogenesis, whose onset, progression, severity, frequency, duration or probability can be reduced, decreased, inhibited, delayed ameliorated or prevented include, for example, fever, headache, sore throat, buccal mucosa spots, rash, maculopapular lesions, cough, congestion, fatigue, body or muscle ache, chills, nausea, vomiting, diarrhea, facial or mouth pain, pneumonia, wheezing, bronchiolitis, encephalitis, swelling of salivary (parotid) glands, pancreas, ovaries or testicles.

For influenza virus, non-limiting examples of physiological conditions, disorders, illness, diseases and symptoms associated with or caused by influenza infection, reactivation or pathogenesis, whose onset, progression, severity, frequency, duration or probability can be reduced, decreased, inhibited, delayed ameliorated or prevented include, for example, chills, fever, cough, sore throat, nasal congestion, sinus congestion, nasal infection, sinus infection, body ache, head ache, fatigue, pneumonia, bronchitis, ear infection, ear ache and death.

For arenavirus (e.g., LCMV, Junin virus, Lassa virus, Guanarito virus, Sabia virus and Machupo virus), non-limiting examples of physiological conditions, disorders, illness, diseases and symptoms caused by or associated with arenavirus infection, reactivation or pathogenesis, whose onset, progression, severity, frequency, duration or probability can be reduced, decreased, inhibited, delayed ameliorated or prevented include, for example, fever, fatigue, malaise, stiff neck, malaise, loss or appetite, abdominal pain, muscle aches, abdominal pain, cough, facial swelling, seizure, tremors, shock, headache, conjunctivitis, athralgia, encephalitis, constipation, diarrhea, nausea and vomiting, eucopenia, oral mucosal ulcers/bleeding, thrombocytopenia and proteinuria.

For coronavirus (e.g., the common cold or SARS), non-limiting examples of physiological conditions, disorders, illness, diseases and symptoms caused by or associated with coronavirus infection, reactivation or pathogenesis, whose onset, progression, severity, frequency, duration or probability can be reduced, decreased, inhibited, delayed ameliorated or prevented include, for example, sore throat, fever, fatigue, malaise, cough, congestion, pneumonia, headache, chills, sinus pain, earache, muscle or body ache.

For poxvirus (e.g., vaccinia virus, Molluscum contagiosum, variola major or variola minor smallpox virus, cow pox, camel pox, sheep pox and monkey pox), non-limiting examples of physiological conditions, disorders, illness, diseases and symptoms caused by or associated with poxvirus infection, reactivation or pathogenesis, whose onset, progression, severity, frequency, duration or probability can be reduced, decreased, inhibited, delayed ameliorated or prevented include, for example, high fever, muscle ache, fatigue, headache, backache, malaise, rash (maculopapular, vesicular or pustular), blisters, pustules or lesions, delirium, vomiting, diarrhea and excess bleeding.

For flavivirus (e.g., Yellow Fever virus, Dengue virus, Japanese Encephalitis and West Nile viruses), non-limiting examples of physiological conditions, disorders, illness, diseases and symptoms associated with or caused by flavivirus infection, reactivation or pathogenesis, whose onset, progression, severity, frequency, duration or probability can be reduced, decreased, inhibited, delayed ameliorated or prevented include, for example, mild, moderate, severe or hemorrhagic fever, headache, body aches, skin rash, swollen lymph glands, neck stiffness and other arthritic symptoms, stupor, disorientation, coma, tremors, convulsions, paralysis and encephalitis.

For adenovirus (e.g., bronchi, lung, stomach, intestine, eye, bladder or skin), non-limiting examples of physiological conditions, disorders, illness, diseases and symptoms associated with or caused by adenovirus infection, reactivation or pathogenesis, whose onset, progression, severity, frequency, duration or probability can be reduced, decreased, inhibited, delayed ameliorated or prevented include, for example, fever, conjunctivitis, keratoconjunctivitis, pharyngoconjunctival fever, headache, chills, febrile respiratory disease, gastroenteritis, sore throat, swollen lymph glands, diarrhea and hemorrhagic cystitis.

For reovirus (e.g., rotavirus, cypovirus and orbivirus), non-limiting examples of physiological conditions, disorders, illness, diseases and symptoms associated with or caused by reovirus infection, reactivation or pathogenesis, whose onset, progression, severity, frequency, duration or probability can be reduced, decreased, inhibited, delayed ameliorated or prevented include, for example, fever, headache, malaise, myalgia, abdominal pain/cramps, vomiting, diarrhea, thirst, dry mouth/tongue, gastroenteritis, leucopenia (Colorado tick fever) and pneumonia.

For picornavirus (e.g., rhinovirus such as those that cause the common cold, apthovirus, hepatovirus, enterovirus such as poliovirus and cardiovirus), non-limiting examples of physiological conditions, disorders, illness, diseases and symptoms associated with or caused by picornavirus infection, reactivation or pathogenesis, whose onset, progression, severity, frequency, duration or probability can be reduced, decreased, inhibited, delayed ameliorated or prevented include, for example, sore throat, fever, fatigue, malaise, myalgia, cough, congestion, pneumonia, headache, nausea, chills, seizure, sinus pain, earache, muscle or body ache, nasal congestion, meningitis, pharyngitis, bronchitis, infectious asthma, encephalitis, acute myocarditis, pericarditis, febrile illness with rash, conjunctivitis, herpangina, paralysis, nervous system infection, muscle infection, heart infection, hepatitis and jaundice.

For togavirus (e.g., alphavirus, sindbus virus and rubellavirus), non-limiting examples of physiological conditions, disorders, illness, diseases and symptoms associated with or caused by togavirus infection, reactivation or pathogenesis, whose onset, progression, severity, frequency, duration or probability can be reduced, decreased, inhibited, delayed ameliorated or prevented include, for example, fever, myalgia, arthritis, headache, fatigue, encephalitis, meningitis, maculopapilar exanthem, arthralgia, maculopapular rash, thrombocytopenic purpura, nausea, swollen lymph nodes, drowsiness, stiff neck, disorientation, convulsions, tremors, coma, death.

For bunyavirus (e.g., hantavirus, phlebovirus and nairovirus), non-limiting examples of physiological conditions, disorders, illness, diseases and symptoms associated with or caused by bunyavirus infection, reactivation or pathogenesis, whose onset, progression, severity, frequency, duration or probability can be reduced, decreased, inhibited, delayed ameliorated or prevented include, for example, fever, hemorrhagic fever, jaundice, hemorrhage, chills, malaise, headache, nausea, vomiting, loss of appetite, abdominal discomfort/pain, back discomfort/pain, muscle pain, tachycardia, tachypnoea, cardiovascular shock, hypoxemia, proteinuria, renal failure, diuresis and liver damage.

For retrovirus (e.g., alpha, beta, delta, gamma, epsilon, lentivirus, oncovirus, immunodeficiency virus and spumavirus), non-limiting examples of physiological conditions, disorders, illness, diseases and symptoms associated with or caused by retrovirus infection, reactivation or pathogenesis, whose onset, progression, severity, frequency, duration or probability can be reduced, decreased, inhibited, delayed ameliorated or prevented include, for example, HIV/AIDS, T cell leukemia and non-demyelinating spastic paraparesis.

Other physiological conditions, disorders, illness, diseases and symptoms associated with or caused by virus infection, reactivation or pathogenesis, are known in the art. Treatment thereof in accordance with the invention methods is also provided.

The invention additionally provides, among other things, compositions and methods embodiments of increasing production of a Th1 cytokine in a subject with or at risk of a viral infection. In one embodiment, a method includes administering to a subject an amount of an IL-10 Receptor (IL-10R) antagonist sufficient to increase Th1 cytokine production in the subject. In another embodiment, a method includes administering to a subject an amount of an IL-10R ligand (e.g., IL-10) antagonist sufficient to increase Th1 cytokine production in the subject. Non-limiting exemplary Th1 cytokines include, interferon (IFN) gamma, TNF-alpha, IL-1alpha, IL-6 and IL-8. Th1 cytokines can be produced, for example, by CD8+ T cells, such as CD8+ T cells specific for a virus comprising a viral infection.

The invention further provides, among other things, compositions and methods embodiments of decreasing IL-10 production in a subject with or at risk of a viral infection. In one embodiment, a method includes administering to a subject an amount of an IL-10 Receptor (IL-10R) antagonist sufficient to decrease IL-10 production in the subject. In another embodiment, a method includes administering to a subject an amount of an IL-10R ligand (e.g., IL-10) antagonist sufficient to decrease IL-10 production in the subject.

The invention moreover provides, among other things, compositions and methods embodiments of increasing immune cell numbers or activation of an immune cell in a subject with or at risk of a viral infection. In one embodiment, a method includes administering to a subject an amount of an IL-10 Receptor (IL-10R) antagonist sufficient to increase immune cell numbers or activation of the immune cell in the subject. In another embodiment, a method includes administering to a subject an amount of an IL-10R ligand (e.g., IL-10) antagonist sufficient to increase immune cell numbers or activation of the immune cell in the subject. Non-limiting exemplary immune cells include T cells and dendritic cells (DC). Additional non-limiting exemplary immune cells include CD4+, CD8+, B220+ and CD11c+ cells.

The invention still further provides, among other things, compositions and methods embodiments of increasing or inducing an antiviral CD8+ T cell response in a subject with or at risk of a viral infection. In one embodiment, a method includes administering to a subject an amount of an IL-10 Receptor (IL-10R) antagonist sufficient to increase or induce an antiviral CD8+ T cell response in the subject. In another embodiment, a method includes administering to a subject an amount of an IL-10R ligand (e.g., IL-10) antagonist sufficient to increase or induce an antiviral CD8+ T cell response in the subject.

In various compositions and methods embodiments, the treated subject is immunosuppressed or at risk of immunosuppression (e.g., is HIV positive, has an immunosuppressive condition, disorder, disease or illness, or is undergoing, has undergone or is a candidate for immunosuppressive treatment or therapy, such as for a tumor or an organ/tissue transplant). Typical numbers of CD8+ T cells range from about 150-1,000 cells/cubic millimeter (mm3) blood in normal (non-immunosuppressed subjects). In a non-limiting example, a subject has reduced numbers of CD4+ cells or antigen-specific CD8+ cells or is suffering from a progressive reduction or loss in CD4+ cell numbers, or has less than 600/cubic millimeter (mm3) blood CD4+ cells, or less than 300/cubic millimeter (mm3) blood CD4+ cells, or less than 200/cubic millimeter (mm3) blood CD4+ cells, or has less than 40% CD4+ cells as a percentage of all lymphocytes in blood, or less than 25% CD4+ cells as a percentage of all lymphocytes in blood, or less than 15% CD4+ cells as a percentage of all lymphocytes in blood. In additional non-limiting examples, a subject has reduced numbers of viral-specific CD8+ T cells. Typical numbers of CD4+ T cells range from about 500-1,500 cells/cubic millimeter (mm3) blood in normal (non-immunosuppressed subjects). Typical numbers of CD4+ T cells, expressed as a percentage of total lymphocytes, range from about 30-70%. In a normal (non-immunosuppressed) subject T-cell ratio, CD4+/CD8+, is usually between 0.9 and 6.0. An immunosuppressed subject may therefore have less than typical amounts, percentages or ratios of CD4+ or CD8+ cells.

Methods embodiments therefore include treatment of a subject that is immunosuppressed (immunocompromised) or is at risk of immunosuppression, as well as a subject having particular physiological conditions, disorders, illnesses, diseases and symptoms, or therapies that can cause or result in transient or longer term immunosuppression, since such subjects have or are at increased risk of opportunistic disorders (e.g., viral infections, such as herpesvirus, arenavirus, etc.) as well as viral infections due to reactivation from latency.

Treatment embodiments also include reducing or eliminating a need, dosage amount or frequency of another treatment, such as another drug or other agent used for treatment. For example, a subject with or at risk of a viral infection/reactivation or pathogenesis or a physiological condition, disorder, illness, disease or symptom caused by or associated with a viral infection/reactivation or pathogenesis may no longer require or may require less of another treatment for the viral infection/reactivation or physiological condition, disorder, illness, disease or symptom associated with caused by or associated with the viral infection/reactivation.

Non-limiting exemplary treatments that may be eliminated or used at reduced doses or frequencies of administration include anti-virals such as protease inhibitors, reverse transcriptase inhibitors, virus fusion inhibitors and virus entry inhibitors. Additional non-limiting exemplary viral treatments that may be eliminated or reduced are as set forth herein (e.g., viral protein or vaccination, antibodies, nucleic acid, etc.) or known in the art.

Methods of the invention providing a beneficial effect or improvement need not result in complete ablation of any particular physiological condition, disorder, illness, disease, or symptom caused by or associated with the viral infection/reactivation. Rather, a treatment can provide a beneficial effect or improvement to any objective or subjective measurable or detectable extent in the viral infection/reactivation or associated physiological condition, disorder, illness, disease, or symptom, in a given subject. A detectable beneficial effect or improvement includes a subjective or objective reduction in the occurrence, frequency, severity, progression, or duration of the viral infection/reactivation or an associated physiological condition, disorder, illness, disease, or symptom thereof; stabilization or inhibition of progression of the viral infection/reactivation or a physiological condition, disorder, illness, disease, or symptom caused by or associated with the viral infection/reactivation; or cure of the viral infection/reactivation or reversal of an associated physiological condition, disorder, illness, disease, or symptom thereof. A treatment that provides a beneficial effect or improvement, "ameliorate" is used synonymously, therefore need not be complete ablation of the infection or any or all associated physiological conditions, disorders, illness, diseases, or symptoms, but is any measurable or detectable, objective or subjective, effect, benefit or improvement in the viral infection/reactivation or an associated physiological condition, disorder, illness, disease, or symptom thereof. Thus, reducing, inhibiting, decreasing, eliminating, delaying, halting or preventing a progression or worsening of the infection/reactivation or a physiological condition, disorder, illness, disease, or symptom caused by or associated with the viral infection/reactivation is a satisfactory outcome.

In embodiments of the methods in which there is a desired outcome, for example, a treatment, identification, screening or diagnostic method, an antagonist of IL-10R or IL-10R ligand (e.g., IL-10) expression or activity can be administered in a sufficient or effective amount. As used herein, a "sufficient amount" or "effective amount" or an "amount sufficient" or an "amount effective" refers to an amount that, in single or multiple doses, alone or in combination with one or more other compounds, treatments, agents (e.g., a drug) or therapeutic regimens, a long term or a short term detectable, measurable or desirable (subjective or objective) outcome. For example, in a treatment method, a measurable or desirable (subjective or objective) outcome includes a detectable improvement or measurable beneficial effect in a given subject, of any degree or for any time period or duration (e.g., for minutes, hours, days, months, years, or cured).

A "sufficient amount" or "effective amount" therefore includes an amount as set forth herein for achieving an objective of a method of the invention. For example, in a treatment method, an objective can be decreasing, reducing, inhibiting, preventing, or delaying onset; decreasing, reducing, inhibiting, delaying, or preventing a progression or worsening of a viral infection/reactivation or an associated physiological condition, disorder, illness, disease, or adverse symptom; or reducing, relieving, ameliorating, or alleviating, severity, frequency, duration, susceptibility or probability of a viral infection/reactivation or associated physiological condition, disorder, illness, disease, or symptom. Hastening a subject's recovery from a viral infection/reactivation or an associated physiological condition, disorder, illness, disease, or symptom is considered a sufficient or effective amount. Additional objectives that reflect a beneficial effect or indicia of therapeutic and prophylactic benefit are as set forth herein and are known to the skilled artisan.

Amounts, frequencies or duration also considered "sufficient" and "effective" are those that result in the elimination or a reduction in amount, frequency or duration of another compound, agent, treatment or therapeutic regimen. Thus, a treatment method in accordance with the invention is considered as having a beneficial or therapeutic effect if contact, administration or delivery in vivo results in the use of a lesser amount, frequency or duration of another compound, agent, treatment or therapeutic regimen to treat the viral infection/reactivation or a physiological condition, disorder, illness, disease, or symptom caused by or associated with the viral infection/reactivation.

A sufficient amount or an effective amount can but need not be provided in a single administration and can but need not be administered alone (i.e., without a second drug, agent, treatment or therapeutic regimen), or in combination with another compound, agent, treatment or therapeutic regimen. In addition, a sufficient amount or an effective amount need not be sufficient or effective if given in single or multiple doses without a second compound, treatment, agent, or therapeutic regimen, since additional doses, amounts, frequency or duration of administration above and beyond such doses, or additional compounds, agents, treatments or therapeutic regimens may be included in order to be effective or sufficient in a given subject.

A sufficient amount or an effective amount need not be effective in each and every subject, nor a majority of subjects in a given group or population. Thus, a sufficient amount or an effective amount means sufficiency or effectiveness in a particular subject, not a group or the general population. As is typical for such methods, some subjects will exhibit a greater or less response to embodiments of the methods than other subjects.

Any compound, agent, treatment or other therapeutic regimen having a desired, beneficial, additive, synergistic or complementary activity or effect can be formulated or used in a combination with or in addition to embodiments of the methods. Methods embodiments therefore include additional treatments, protocols and therapies, which include any other composition, treatment, protocol or therapeutic regimen. In one embodiment, a plurality of antagonists of IL-10R or IL-10R ligand (e.g., IL-10) expression or activity are administered to the subject. In additional embodiments, a compound, agent, treatment or therapeutic regimen is for providing a subject with protection against, treatment of, decreasing susceptibility towards, treating a viral infection/reactivation or a physiological condition, disorder, illness, disease, or symptom caused by or associated with viral infection/reactivation.

Combination methods embodiments include, for example, anti-viral drugs, such as protease inhibitors, reverse transcriptase inhibitors, virus fusion inhibitors and virus entry inhibitors, antibodies to viral proteins, immune stimulating agents, etc.), and include contact with, administration in vitro or in vivo, with another compound, agent, treatment or therapeutic regimen appropriate for the viral infection/reactivation or condition, disorder, illness, disease or symptom thereof.

The compound, agent, treatment or therapeutic regimen may be used in accordance with any method embodiment, as set forth herein, prior to, concurrently or following contacting or administering an antagonist of IL-10R or IL-10R ligand (e.g., IL-10) expression or activity.

Non-limiting examples of combination embodiments include protease inhibitors, reverse transcriptase inhibitors, virus fusion inhibitors and virus entry inhibitors, live or attenuated virus, viral proteins and antibodies that bind to viral proteins. A pool of protease inhibitors, reverse transcriptase inhibitors, virus fusion inhibitors and virus entry inhibitors, inactivated, live or attenuated virus, viral proteins, viral nucleic acid (e.g., antisense or RNAi) or viral binding antibodies (e.g., monoclonal or polyclonal) can be combined with an antagonist of IL-10R or IL-10R ligand (e.g., IL-10) expression or activity or administered separately (prior to, concurrently with or following) administration of an antagonist of IL-10R or IL-10R ligand (e.g., IL-10) expression or activity.

Specific non-limiting examples of combination embodiments include AK602, AMD070, APV, ATV, ATZ, AVX754, AZT, Abacavir, Acyclovir, Adefovir dipivoxil, Adriamycin, Agenerase, Aldesleukin, Alovudine, AmBisome, Amdoxovir, Amphocin, Amphotec, Amphotericin B, Ampligen, Amprenavir, Androderm, Androgel, Aptivus, Atazanavir, Azithromycin, BMS-488043, Bactrim, Baraclude, Biaxin, BufferGel, C31G, CD4-IgG2, CPV, CS, Calanolide A, Capravirine, Carbopol 974P, Carrageenan, Carraguard, Cellulose sulfate, Cidofivir, Clarithromycin, Combivir, Copegus, Cotrimoxazole, Crixivan, Cyanovirin-N, Cytovene, DAPD, DLV, DPC 817, DS, Delavirdine, Depoi-Testosterone, Dextran sulfate, Didanosine, Diflucan, Doxil, Doxorubicin, Dronabinol, Duofilm, EFV, Efavirenz, Elvucitabine, Emtricitabine, Emtriva, Enfuvirtide, Entecavir, Epivir, Epoetin alfa, Epogen, Epzicom, Etopophos (phosphate salt), Etoposide, Etravirine, Fluconazole, Fortovase, Fosamprenavir, Fungizone, Fuzeon, GSK-873,140 (aplaviroc), GW433908, Gammar-P, Ganciclovir, Growth hormone, Human growth hormone, HEC, Hepsera, Hivid, Hydroxyethyl cellulose, IDV, IGIV, Imiquimod cream, Interleukin-2 (IL-2), INH, Immune Globulin, Indinavir, Interferon alfa-2, Interferon alfa-2b, Intron A (2b), Invirase, Isoniazid, Itraconazole, KP-1461, Kaletra, L-000870810, LPV/RTV, Lamivudine, Lexiva, Marinol, Megace, Megestrol, Mycobutin, NFV, NVP, Naphthalene 2-sulfonate polymer, Nebupent, Nelfinavir, Neutrexin, Nevirapine, New-Fill, Norvir, Nydrazid, Occlusal, Onxol, Oseltamivir, PA-457, PMPA, PRO2000, PRO542, Paclitaxel, Paxene, Pegasys (2a), Pentamidine, Peptide T, pleconaril, podofilox, podophyllin, Poly(1)-Poly(C12U), Poly-L-lactic acid, Polygam S/D, Procrit, Proleukin, RCV, RTV, RVT, Racivir, Rebetol, Rescriptor, Retrovir, Reverset, Reyataz, Ribavirin, Rifabutin, Rifadin, Rifampin, Rimactane, Ritonavir, Roferon-A (2a), SCH—C, SCH-D (vicriviroc), SQV, Saquinavir, Savvy, Sculptra, Septra, Serostim, Somatropin, Sporanox, Stavudine, Sulfamethoxazole, Sustanon, Sustiva, T-20, TDF, THC, TMC114, TMC125, TNX-355, Taxol, Tenofovir, Tenofovir disoproxil fumarate, Testosterone, Tipranavir, Toposar, TransVer-Sal, Trichloroacetic acid (TCA), Trimethoprim, Trimetrexate, Trizivir, Truvada, UC-781, UK-427,857 (maraviroc), Ushercell, Valcyte, Valganciclovir, Valproic acid, VePesid, Vicriviroc, Videx, Viracept, Viranol, Viramune, Virazole, Viread, Vitrasert, ZDV, Zalcitabine, Zerit, Ziagen, Zidovudine, Zithromax, Zovirax, D4T, ddC, β-LFddC, P-LFd4C, DDI, f-APV, 3TC, 5-FU and human erythropoietin (EPO).

Additional specific non-limiting examples of combination embodiments include treatments such as steroidal and non-steroidal anti-inflammatory drugs such as acetominophen, ibuprophen, naproxen, indomethacin, piroxicam, ketoprofen and pyrancarboxylic acid (Lodine).

Further additional exemplary treatments include viral protein, antibody that binds to viral protein, viral nucleic acid, passive vaccination such as VIG and vaccination with inactivated virus, virus extract, attenuated virus or live virus.

For HIV, non-limiting proteins include envelope protein gp160, gp120 or gp41, gag protein, pol protein, p7, p17, p24, tat, rev, nef, vif, vpr, vpu, reverse transcriptase, integrase, or protease), an antibody that binds to an HIV protein (e.g., present on one or more of envelope protein gp160, gp120 or gp41, gag protein, pol protein, p7, p17, p24, tat, rev, nef, vif, vpr, vpu, reverse transcriptase, integrase, or protease). HIV proteins and binding antibodies include those present on or that bind to one or more of HIV-1 (e.g., Groups M, N and O, or subtypes include A, B, A/B, A/E, A/G, C, D, F, G, H, J and K subtypes, and mixtures thereof) or HIV-2, drug resistant HIV types, groups, subtypes or isolates.

For herpesvirus (HV), non-limiting proteins include envelope protein (e.g., glycoprotein gp42, gp350, gpK8.1A, B, C, D, E, H, L (gB, gC, gD, gE, gH, gL)), tegument protein (e.g., UL17, UL36, UL37, UL48, UL49, US11, UL11, UL14, UL16, UL21, UL41, UL46, UL47, VP13/14, VP16, VP22, etc.), capsid protein (e.g., VP5, VP19c, VP21, VP23, VP24, VP26, etc.), core protein and polymerase. Still further non-limiting exemplary HV treatments include HV.

For influenza virus, non-limiting proteins include one or more present on A/PR/34, A/HK8/68, A/HK/1/68, H1N1, H2N2, H3N2, H5N1, H9N2, H2N1, H4N6, H6N2, H7N2, H7N3, H4N8, H5N2, H2N3, H11N9, H3N8, H1N2, H11N2, H11N9, H7N7, H2N3, H6N1, H13N6, H7N1, H11N1, H7N2 and H5N3 strains/isolates.

For poxvirus, non-limiting proteins include one or more of B5R, L1R, D8L, A33R, A27L, A17L, L5, A21, H2, H3L, A28, A14, A56, A34, A36, A2, or a B5R, L1R, D8L, A33R, A27L, A17L, L5, A21, H2, A28, A14, A56, A34, A36, or A2. Additional poxvirus treatments include vaccinia immune globulin (VIG) or an antibody that binds to a poxvirus protein (e.g., a vaccinia virus protein), live and attenuated pathogenic or non-pathogenic Vaccinia virus such as vaccinia Ankara (MVA), vaccinia virus Lister strain, vaccinia virus Copenhagen strain, vaccinia virus Connaught strain, vaccinia virus Brighton strain, vaccinia virus LC16 m8 strain, vaccinia virus LC16MO, vaccinia virus IHD-J, vaccinia virus Dairen I, vaccinia virus NYCBOH strain, vaccinia virus Wyeth strain, vaccinia virus Tian Tan, vaccinia virus LIVP, vaccinia virus L-IPV, vaccinia virus Dryvax® and ACAM1000.

Still additional examples of combination embodiments include immune system enhancing treatments. Specific non-limiting examples include cytokines, chemokines, interferons and interleukins; cytokine, chemokine, interferon, and interleukin receptors; and antiviral drugs and agents. Specific non-limiting examples are as set forth herein and are also known in the art.

A "peptide," "polypeptide" or "protein" refers to two or more amino acids covalently linked by an amide bond or non-amide equivalent. Polypeptides include full length native polypeptide, and "modified" forms such as subsequences, variant sequences, fusion/chimeric sequences and dominant-negative sequences. Non-limiting examples of polypeptides include dominant negative forms of IL-10R or IL-10R ligand (e.g., IL-10) having antagonistic activity on IL-10R ligand (e.g., IL-10) or IL-10R expression or activity, respectively. Exemplary IL-10R polypeptides are as follows:

Protein IL-10Ralpha *Homo sapiens* (NCBI:NP_001549.1 GI:4504633) (SEQ ID NO:1)

mlpclvvlla allslrlgsd ahgtelpspp svwfeaeffh hilhwtpipn qsestcyeva llrygieswn sisncsqtls ydltavtldl yhsngyrarv ravdg-srhsn wtvtntrfsv devtltvgsv nleihngfil gkiqlprpkm apandtyesi fshfreyeia irkvpgnftf thkkvkhenf slltsgevge fcvqvkpsva srsnkgmwsk eecisltrqy ftvtnviiff afvlllsgal ayclalqlyv rrrkklpsvl lfkkpspfif isqrpspetq dtihpldeea flkvspelkn ldlhg-stdsg fgstkpslqt eepqfllpdp hpqadrtlgn geppvlgdsc ssgssnstds giclqepsls pstgptweqq vgsnsrgqdd sgidlvqnse gragdtqggs alghhsppep evpgeedpaa vafqgylrqt rcaeekatkt gcleeesplt dglgpkfgrc lvdeaglhpp alakgylkqd plemtlassg aptgqwnqpt eewsllalss csdlgisdws fahdlaplgc vaapggllgs fnsdlvtlpl iss-lqsse Protein IL-10Rbeta *Homo sapiens* (NCBI:NP_000619.3 GI:24430215) (SEQ ID NO:2)

mawslgswlg gcllvsalgm vpppenvrmn svnfknilqw espafakgnl tftaqylsyr ifqdkcmntt ltecdfssls kygdhtlrvr aefadehsdw vnit-fcpvdd tiigppgmqv evladslhmr flapkieney etwtmknvyn swtynvqywk ngtdekfqit pqydfevlrn lepwttycvq vrgflpdrnk agewsepvce qtthdetvps wmvavilmas vfmvclallg cfallwcvyk ktkyafsprn slpqhlkefl ghphhntllf fsfplsdend vfdklsviae dses-gkqnpg dscslgtppg qgpqs Subsequences and fragments refer to polypeptides having one or more fewer amino acids in comparison to a reference (e.g., native) polypeptide sequence. A variant peptide can have a sequence with 50%, 60%, 70%, 75%, 80%, 85%, 90%, 95%, 96%, 97%, 98%, or more identity to a reference sequence. Variant sequences include naturally occurring alterations of sequence, due to intra-species polymorphisms or different species, as well as artificially produced alterations of sequence.

Peptides include L- and D-isomers, and combinations thereof. Peptides can include modifications typically associated with post-translational processing of proteins, for example, cyclization (e.g., disulfide or amide bond), phosphorylation, glycosylation, carboxylation, ubiquitination, myristylation, or lipidation. Modified peptides can have one or more amino acid residues substituted with another residue, added to the sequence or deleted from the sequence. Specific examples include one or more amino acid substitutions, additions or deletions (e.g., 1-3, 3-5, 5-10, 10-20, or more).

Peptides synthesized and expressed as fusion proteins have one or more additional domains linked thereto, and are also referred to as chimeric polypeptides. The additional domain(s) may confer an additional function upon the sequence. For example, IL-10R-IgG (Fc) fusion proteins can have antagonist activity.

The term "fusion," when used in reference to two or more molecules (e.g., polypeptides) means that the molecules are covalently attached. A particular example for attachment of two protein sequences is an amide bond or equivalent. The term "chimeric" and grammatical variations thereof, when used in reference to a protein, means that the protein is comprised of one or more heterologous amino acid residues from one or more different proteins.

The term "heterologous," when used in reference to a polypeptide, means that the polypeptide is not normally contiguous with the other polypeptide in its natural environment. Thus, a chimeric polypeptide means that a portion of the polypeptide does not exist fused with the other polypeptide in normal cells. In other words, a chimeric polypeptide is a molecule that does not normally exist in nature, i.e., such a molecule is produced by the hand man, e.g., artificially produced through recombinant DNA technology.

Proteins include antibodies, which bind to molecules (antigens) via heavy and light chain variable domains, $V_H$ and VL, respectively. An antibody is any polyclonal or monoclonal immunoglobulin molecule, or mixture thereof, such as IgM, IgG, IgA, IgE, IgD, and any subclass thereof, such as $IgG_1$, $IgG_2$, $IgG_3$, $IgG_4$, etc. An antibody also includes a functional (e.g., binding activity) or active (e.g., antagonist activity) subsequence or fragment, such as, for example, Fab, Fab', $F(ab')_2$, Fv, Fd, single-chain Fv (scFv), disulfide linked Fv, light chain variable (VL) and heavy chain variable (VH) unless otherwise expressly stated.

A monoclonal antibody refers to an antibody that is based upon, obtained from or derived from a single clone, including any eukaryotic, prokaryotic, or phage clone. A "monoclonal" antibody is therefore not defined by the method in which it is produced. As used herein, a specific name, numeral or other designation used to refer to a hybridoma or other cells line that produce antibody can also be used to refer to the antibody produced by that cell line.

Antibodies are useful for modulating expression or activity of IL-10R or IL-10R ligand (e.g., IL-10). Particular antibodies decrease, reduce, inhibit, delay or prevent (antagonize) expression or an activity of IL-10R or IL-10R ligand (e.g., IL-10). Antibodies include those specific or selective for binding to IL-10R or IL-10R ligand (e.g., IL-10). That is, binding to molecules other than IL-10R or IL-10R ligand (e.g., IL-10) is such that the binding does not significantly interfere with binding to IL-10R or IL-10R ligand (e.g., IL-10). Selective binding can be distinguished from non-selective binding using specificity, affinity and other binding assays, competitive and non-competitive, known in the art.

Exemplary antibodies include those produced by 1B1.3a (BD Biosciences, Pharmingen Division, Cat. No. 550012), 1B1.2 hybridoma (DNAX) or an anti-mouse IL-10R(R & D Systems, Cat. No. AF-474-NA). Exemplary antibodies also include modified forms of these antibodies. Examples of modifications include one or more amino acid substitutions, additions or deletions of the antibody, provided that the modified antibody has all or at least part of an activity of reference antibody, e.g., antagonist activity.

A particular example of a modification is where an antibody is altered to have a different isotype or subclass by, for example, substitution of the heavy chain constant region. Thus, modifications include deleting small and large regions of amino acid sequences from an antibody and substituting the deleted region with another amino acid sequence, whether the sequence is greater or shorter in length than the deleted region.

Additional modifications included in the invention are antibody derivatives, i.e., the covalent attachment of any type of molecule to the antibody. Specific examples of antibody derivatives include antibodies that have been glycosylated, acetylated, phosphorylated, amidated, formylated, ubiquitinated, and derivatization by protecting/blocking groups and any of numerous chemical modifications.

Amino acid substitutions may be with the same amino acid, except that a naturally occurring L-amino acid is substituted with a D-form amino acid. Modifications therefore include one or more D-amino acids substituted for L-amino acids, or mixtures of D-amino acids substituted for L-amino acids. Modifications further include structural and functional analogues, for example, peptidomimetics having synthetic or non-natural amino acids or amino acid analogues and derivatized forms.

Modifications include cyclic structures such as an end-to-end amide bond between the amino and carboxy-terminus of the molecule or intra- or inter-molecular disulfide bond. Polypeptides may be modified in vitro or in vivo, e.g., post-translationally modified to include, for example, sugar residues, phosphate groups, Modified antibodies having altered characteristics, such as increased binding affinity, can be produced using methods known in the art. For example, affinity maturation techniques can be used to improve antibody binding affinity (US 2004/0162413 A1; U.S. Pat. Nos. 6,656,467, 6,531,580, 6,590,079 and 5,955,358; Fiedler et al., *Protein Eng.* 15:931 (2002); Pancook et al., *Hybrid. Hybridomics* 20:383 (2001); Daugherty et al., *Protein Eng.* 11:825 (1998); Wu et al., *Proc. Nat'l Acad. Sci. USA* 95:6037 (1998); and Osbourn et al., *Immunotechnology* 2:181 (1996)).

A modified protein can have an amino acid substitution, addition or deletion (e.g., 1-3, 3-5, 5-10 or more residues). Amino acid substitutions can be conservative or non-conservative and may be in a constant or variable region of the antibody. One or a few conservative amino acid substitutions in constant or variable regions are likely to be tolerated. Non-conservative substitution of multiple amino acids in hypervariable regions is likely to affect binding activity, specificity or antibody function or activity.

A "conservative substitution" means the replacement of one amino acid by a biologically, chemically or structurally similar residue. Biologically similar means that the substitution is compatible with biological activity, e.g., binding or antagonist activity. Structurally similar means that the amino acids have side chains with similar length, such as alanine, glycine and serine, or similar size. Chemical similarity means that the residues have the same charge or are both hydrophilic or hydrophobic. Particular non-limiting examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine and serine for threonine.

Regional mutability analysis can be used to predict the effect of particular substitutions in CDR and FR domains (Shapiro et al., *J. Immunol.* 163:259 (1999)). In brief, sequence comparison indicates a hierarchy of mutability among di- and trinucleotide sequences located within Ig intronic DNA, which predicts regions that are more or less mutable. Quantitative structure-activity relationship (QSAR) can be used to identify the nature of the antibody recognition domain and, therefore, amino acids that participate in ligand binding. Models based upon QSAR can in turn be used to predict the effect of mutations. For example, the effect of mutations on the association and dissociation rate of an antibody interacting with its antigen has been used to construct quantitative predictive models for both kinetic ($K_a$ and $K_d$) constants, which can in turn be used to predict the effect of other mutations on the antibody (De Genst et al., *J. Biol. Chem.* 277:29897 (2002)).

The effect of a substitution can be assayed in order to identify antibodies retaining at least a part of the binding activity, or antagonist activity of reference antibody. For example, an amino acid substitution in a hypervariable region may be assayed for binding or antagonist activity.

Modified antibodies include amino acid sequence with 50-100%, or 50%, 60%, 70%, 75%, 80%, 85%, 90%, 95%, 96%, 97%, 98%, 99%, or more identity to a reference antibody produced by 1B1.3a (BD Biosciences, Pharmingen Division, Cat. No. 550012), 1B1.2 hybridoma (DNAX) or an anti-mouse IL-10R(R & D Systems, Cat. No. AF-474-NA). The identity can be over a defined area (region or domain) of the sequence.

The term "identity" and grammatical variations thereof mean that two or more referenced entities are the same. Thus, where two antibody sequences are identical, they have the same amino acid sequence. "Areas, regions or domains of identity" mean that a portion of two or more referenced entities are the same. Thus, where two antibody sequences are identical over one or more sequence regions, they share identity in these regions. The term "substantial identity" means that the identity is structurally or functionally significant. That is, the identity is such that the molecules are structurally identical or have at least one of the same activity (e.g., antagonist activity) even though the sequences are different.

Due to variation in the amount of sequence conservation between structurally and functionally related proteins, the amount of sequence identity for substantial identity will depend upon the protein, the region and any function of that region. Although there can be as little as 30% sequence identity for proteins to have substantial identity, typically there is more, e.g., 50%, 60%, 75%, 85%, 90%, 95%, 96%, 97%, 98%, identity to a reference sequence. For nucleic acid sequences, 50% sequence identity or more typically constitutes substantial homology, but again can vary depending on the comparison region and its function, if any.

The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol. Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Additional non-limiting examples of antibodies include antibodies having substantially the same binding affinity as the antibody produced by 1B1.3a (BD Biosciences, Pharmingen Division, Cat. No. 550012), 1B1.2 hybridoma (DNAX) or an anti-mouse IL-10R(R & D Systems, Cat. No. AF-474-NA). As used herein, the term "the same," when used in reference to antibody binding affinity, means that the dissociation constant ($K_d$) is within about 1 to 100 fold of the reference antibody (1-100 fold greater affinity or 1 to 100 fold less affinity, or any numerical value or range or value within such ranges, than the reference antibody). The term "substantially the same" when used in reference to antibody binding affinity, means that the dissociation constant ($K_d$) is within about 5 to 5000 fold of the reference antibody, 5-5000 fold greater affinity or 5-5000 fold less affinity than the reference antibody, e.g., antibody produced by 1B1.3a, BD Biosciences, Pharmingen Division, Cat. No. 550012, 1B1.2 hybridoma, DNAX, or anti-mouse IL-10R, R & D Systems, Cat. No. AF-474-NA). Antibodies with greater or less affinity may have the same or substantially the same binding specificity as the exemplified antibodies. Because the binding affinity of such antibodies may differ from the reference antibody (i.e., have greater or less affinity), the antibodies with substantially the same binding specificity will vary in their ability to compete for binding to IL-10R or IL-10R ligand (e.g., IL-10).

Binding affinity can be determined by association ($K_a$) or dissociation ($K_d$) rate. Equilibrium affinity constant, K, is the ratio of $K_a/K_d$. Association ($K_a$) and dissociation ($K_d$) rates can be measured using surface plasmon resonance (SPR) (Rich and Myszka, Curr. Opin. Biotechnol. 11:54 (2000); Englebienne, Analyst. 123:1599 (1998)). Instrumentation and methods for real time detection and monitoring of binding rates are known and are commercially available (BiaCore 2000, Biacore AB, Upsala, Sweden; and Malmqvist, Biochem. Soc. Trans. 27:335 (1999)).

Further non-limiting examples of antibodies include antibodies that competitively inhibit binding of an antibody produced by 1B1.3a (BD Biosciences, Pharmingen Division, Cat. No. 550012), 1B1.2 hybridoma (DNAX) and anti-mouse IL-10R(R & D Systems, Cat. No. AF-474-NA) to IL-10R. Specific examples include antibodies having substantially the same binding specificity as the antibody produced by 1B1.3a (BD Biosciences, Pharmingen Division, Cat. No. 550012), 1B1.2 hybridoma (DNAX) or an anti-mouse IL-10R(R & D Systems, Cat. No. AF-474-NA); and antibodies that bind to the epitope top which an antibody produced by 1B1.3a (BD Biosciences, Pharmingen Division, Cat. No. 550012), 1B1.2 hybridoma (DNAX) or an anti-mouse IL-10R(R & D Systems, Cat. No. AF-474-NA) binds.

An antibody having "substantially the same," binding specificity is able to compete with a reference antibody (e.g., antibody produced by 1B1.3a (BD Biosciences, Pharmingen Division, Cat. No. 550012), 1B1.2 hybridoma (DNAX) or an anti-mouse IL-10R(R & D Systems, Cat. No. AF-474-NA) for binding to IL-10R or IL-10R ligand (e.g., IL-10). In the context of binding specificity, "the same" means that each antibody can completely inhibit binding of the other antibody to IL-10R or IL-10R ligand (e.g., IL-10). "Substantially the same" in the context of binding specificity means each antibody can at least partially inhibit binding of the other antibody to IL-10R or IL-10R ligand (e.g., IL-10). In particular embodiments, an antibody competitively inhibits binding of antibody produced by 1B1.3a (BD Biosciences, Pharmingen Division, Cat. No. 550012), 1B1.2 hybridoma (DNAX) or an anti-mouse IL-10R(R & D Systems, Cat. No. AF-474-NA) to IL-10R by at least 95%, at least 90%, at least 85%, at least 80%, at least 75%, at least 70%, at least 65%, at least 60%, at least 55%, at least 50%, at least 45%, at least 40%, at least 35%, or at least 30%.

Antibodies include subsequences (e.g., fragments). Non-limiting examples include an Fab, Fab', F(ab')$_2$, Fv, Fd, single-chain Fvs (scFv), single-chain antibodies, disulfide-linked Fvs (sdFv) and VL or VH domain fragments. In particular aspects, an Fab, Fab' and F(ab')2, Fd, single-chain Fvs (scFv), single-chain antibodies, disulfide-linked Fvs (sdFv) and light chain variable ($V_L$) and heavy chain variable ($V_H$) subsequences. Combinations of such subsequences are also included. For example, a combination of $V_L$ or $V_H$ subsequences can be joined by a linker sequence thereby forming a $V_L$-$V_H$ chimera. A combination of single-chain Fvs (scFv) subsequences can be joined by a linker sequence thereby forming a scFv-scFv chimera.

Antibody subsequences an be prepared by proteolytic hydrolysis of the antibody, for example, by pepsin or papain digestion of whole antibodies. The terms "functional subsequence" and "functional fragment" when referring to an antibody refers to a portion of an antibody that retains at least a part of one or more functions or activities as the reference antibody.

Antibody fragments produced by enzymatic cleavage with pepsin provide a 5S fragment, denoted F(ab')2. This fragment can be further cleaved using a thiol reducing agent to produce 3.5S Fab' monovalent fragments. Alternatively, an enzymatic cleavage using pepsin produces two monovalent Fab' fragments and the Fc fragment directly (see, e.g., U.S. Pat. Nos. 4,036,945 and 4,331,647; and Edelman et al., Methods Enymol. 1:422 (1967)). Other methods of cleaving antibodies, such as separation of heavy chains to form monovalent light-heavy chain fragments, further cleavage of fragments, or other enzymatic or chemical may also be used. Genetic techniques include expression of all or a part of the antibody gene into a host cell such as Cos cells or E. coli. The recombinant host cells synthesize intact or single antibody chain, such as a scFv (see, e.g., Whitlow et al., In: Methods: A Companion to Methods in Enzymology 2:97 (1991), Bird et al., Science 242:423 (1988); and U.S. Pat. No. 4,946,778). Single-chain Fvs and antibodies can be produced as described, for example, in U.S. Pat. Nos. 4,946,778 and 5,258,498; Huston et al., Methods Enzymol. 203:46 (1991); Shu et al., Proc. Natl. Acad. Sci. USA 90:7995 (1993); and Skerra et al., Science 240:1038 (1988).

Antibodies include additions/insertions. For example, an addition can be the covalent or non-covalent attachment of any type of molecule to the antibody. Specific examples of additions include glycosylation, acetylation, phosphorylation, amidation, formylation, ubiquitinatation, and derivatization by protecting/blocking groups and any of numerous chemical modifications.

Additions further include fusion (chimeric) polypeptide sequences, which is an amino acid sequence having one or more molecules not normally present in a reference native (wild type) sequence covalently attached to the sequence. A particular example is an amino acid sequence of another antibody to produce a multispecific antibody.

Another particular example of a modified an antibody having an amino acid addition is one in which a second heterologous sequence, i.e., heterologous functional domain is attached that confers a distinct or complementary function upon the antibody. For example, an amino acid tag such as T7 or polyhistidine can be attached to an antibody in order to facilitate purification of the antibody or detection of the antigen. Thus, antibodies can include one or more heterologous domains, wherein the domain confers a complementary or distinct function, on the antibody.

Heterologous functional domains are not restricted to amino acid residues. Thus, a heterologous functional domain includes any of a variety of different types of small or large functional moieties. Such moieties include nucleic acid, peptide, carbohydrate, lipid or small organic compounds, such as a drug (e.g., an antiviral), metals (gold, silver), etc.

Linker sequences may be inserted between the antibody sequence and the heterologous functional domain so that the two entities maintain, at least in part, a distinct function or activity. Linker sequences may have one or more properties that include a flexible conformation, an inability to form an ordered secondary structure or a hydrophobic or charged character which could promote or interact with either domain. Amino acids typically found in flexible protein regions include Gly, Asn and Ser. Other near neutral amino acids, such as Thr and Ala, may also be used in the linker sequence. The length of the linker sequence may vary without significantly affecting a function or activity of the fusion protein (see, e.g., U.S. Pat. No. 6,087,329). Linkers further include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST).

Additional examples of heterologous functional domains are detectable labels. Specific examples of detectable labels include fluorophores, chromophores, radioactive isotopes (e.g., S35, P32, 1125), electron-dense reagents, enzymes, ligands and receptors. Enzymes are typically detected by their activity. For example, horseradish peroxidase is usually detected by its ability to convert a substrate such as 3,3-',5,5-'-tetramethylbenzidine (TMB) to a blue pigment, which can be quantified. Ligands may bind other molecules such as biotin, which may bind avidin or streptavidin, and IgG, which can bind protein A.

Antibodies include "human" forms, which mean that the amino acid sequence of the antibody is fully human or can or do exist in a human antibody. An antibody that is non-human may be made fully human by substituting non-human amino acid residues with amino acid residues that can or do exist in a human antibody. Amino acid residues present in human antibodies, CDR region maps and human antibody consensus residues are known in the art (see, e.g., Kabat, *Sequences of Proteins of Immunological Interest*, 4th Ed.US Department of Health and Human Services. Public Health Service (1987); Chothia and Lesk, *J. Mol. Biol.* 186:651 (1987); Padlan, *Mol. Immunol.* 31:169 (1994); and Padlan, *Mol. Immunol.* 28:489 (1991)). A consensus sequence of human $V_H$ subgroup III, based on a survey of 22 known human $V_H$ III sequences, and a consensus sequence of human $V_L$ kappa-chain subgroup I, based on a survey of 30 known human kappa I sequences is described in Padlan *Mol. Immunol.* 31:169 (1994); and Padlan *Mol. Immunol.* 28:489 (1991)). Human antibodies therefore include antibodies in which one or more amino acid residues have been substituted with one or more amino acids present in another human antibody.

Antibodies include "humanized" forms, which means that the amino acid sequence of the antibody has non-human amino acid residues (e.g., mouse, rat, goat, rabbit, etc.) of one or more complementarity determining regions (CDRs) that specifically bind to the desired antigen in an acceptor human immunoglobulin molecule, and one or more human amino acid residues in the Fv framework region (FR), which are amino acid residues that flank the CDRs. Human framework region residues of the immunoglobulin can be replaced with corresponding non-human residues. Residues in the human framework regions can therefore be substituted with a corresponding residue from the non-human CDR donor antibody to alter, generally to improve, antigen affinity or specificity, for example. In addition, a humanized antibody may include residues, which are found neither in the human antibody nor in the donor CDR or framework sequences. For example, a framework substitution at a particular position that is not found in a human antibody or the donor non-human antibody may improve binding affinity or specificity human antibody at that position. Antibody framework and CDR substitutions based upon molecular modeling are known in the art, e.g., by modeling of the interactions of the CDR and framework residues to identify framework residues important for antigen binding and sequence comparison to identify unusual framework residues at particular positions (see, e.g., U.S. Pat. No. 5,585,089; and Riechmann et al., *Nature* 332:323 (1988)).

Antibodies referred to as "primatized" are within the meaning of "humanized" as used herein, except that the acceptor immunoglobulin molecule and framework region amino acid residues may be any primate amino acid residue (e.g., ape, gibbon, gorilla, chimpanzees orangutan, macaque), in addition to any human residue.

Antibodies include "chimeric" forms, which means that the amino acid sequence of the antibody contains one or more portions that are derived from, obtained or isolated from, or based upon two or more different species. That is, for example, a portion of the antibody may be human (e.g., a constant region) and another portion of the antibody may be non-human (e.g., a murine heavy or light chain variable region). Thus, a chimeric antibody is a molecule in which different portions of the antibody are of different species origins. Unlike a humanized antibody, a chimeric antibody can have the different species sequences in any region of the antibody.

Human antibodies can be produced by immunizing human transchromosomic KM mice™ (WO 02/43478) or HAC mice (WO 02/092812). KM mice™ and HAC mice express human immunoglobulin genes. Using conventional hybridoma technology, splenocytes from immunized mice that respond to the antigen can be isolated and fused with myeloma cells. A monoclonal antibody can be obtained that binds to the antigen. An overview of the technology for producing human antibodies is described in Lonberg and Huszar (*Int. Rev. Immunol.* 13:65 (1995)). Transgenic animals with one or more human immunoglobulin genes (kappa or lambda) that do not express endogenous immunoglobulins are described, for example in, U.S. Pat. No. 5,939,598. Additional methods for producing human polyclonal antibodies and human monoclonal antibodies are described (see, e.g., Kuroiwa et al., *Nat. Biotechnol.* 20:889 (2002); WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598).

Humanized antibodies can be produced by a variety of techniques known in the art including, for example, CDR-grafting (EP 239,400; WO91/09967; U.S. Pat. Nos. 5,225,539; 5,530,101; and 5,585,089), veneering or resurfacing (EP 592,106; EP 519,596; Padlan, *Mol. Immunol.* 28:489 (1991); Studnicka et al., *Protein Engineering* 7:805 (1994); Roguska et al., *Proc. Nat'l. Acad. Sci. USA* 91:969 (1994)), and chain shuffling (U.S. Pat. No. 5,565,332). Human consensus sequences (Padlan, *Mol. Immunol.* 31:169 (1994); and Padlan, *Mol. Immunol.* 28:489 (1991)) have been used to humanize antibodies (Carter et al., *Proc. Natl. Acad. Sci. USA* 89:4285 (1992); and Presta et al., *J. Immunol.* 151:2623 (1993)).

Chimeric antibodies can be produced by methods known in the art (e.g., Morrison, *Science* 229:1202 (1985); Oi et al., *BioTechniques* 4:214 (1986); Gillies et al., *J. Immunol. Methods* 125:191 (1989); and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l. Acad. Sci. USA* 81:6851 (1984); Boulianne et al., *Nature* 312:643 (1984); Capon et al., *Nature* 337:525 (1989); and Traunecker et al., *Nature* 339:68 (1989).

Protein suitable for generating antibodies can be produced by any of a variety of standard protein purification or recombinant expression techniques known in the art. For example, IL-10R or IL-10R ligand (e.g., IL-10) peptides can be produced by standard peptide synthesis techniques, such as solid-phase synthesis. A portion of the protein may contain an amino acid sequence such as a T7 tag or polyhistidine sequence to facilitate purification of expressed or synthesized protein. The protein may be expressed in a cell and purified. The protein may be expressed as a part of a larger protein (e.g., a fusion or chimera) by recombinant methods.

Monoclonal antibodies can be readily generated using techniques including hybridoma, recombinant, and phage display technologies, or a combination thereof (see U.S. Pat. Nos. 4,902,614, 4,543,439, and 4,411,993; see, also *Monoclonal Antibodies, Hybridomas: A New Dimension in Biological Analyses*, Plenum Press, Kennett, McKeam, and Bechtol (eds.), 1980, and Harlow et al., *Antibodies: A Laboratory Manual*, Cold Spring Harbor Laboratory Press, 2nd ed. 1988). Suitable techniques that additionally may be employed in the method including antigen affinity purification, non-denaturing gel purification, HPLC or RP-HPLC, purification on protein A column, or any combination of these techniques. Antibody isotype can be determined using an ELISA assay, for example, a human Ig can be identified using mouse Ig-absorbed anti-human Ig.

Animals which may be immunized include mice, rabbits, rats, sheep, cows or steer, goats, or guinea pigs; such animals include those genetically modified to include human IgG gene loci as set forth herein and known in the art. Such animals can therefore be used to produce antibodies. Additionally, to increase the immune response, antigen can be coupled to another protein such as ovalbumin or keyhole limpet hemocyanin (KLH), thyroglobulin and tetanus toxoid, or mixed with an adjuvant such as Freund's complete or incomplete adjuvant. Initial and any optional subsequent immunization may be through intraperitoneal, intramuscular, intraocular, or subcutaneous routes. Subsequent immunizations may be at the same or at different concentrations of antigen preparation, and may be at regular or irregular intervals.

IL-10R or IL-10R ligand (e.g., IL-10) nucleic acids including antisense and RNAi can modulate expression or activity of IL-10R or IL-10R ligand (e.g., IL-10). Antisense includes single, double or triple stranded polynucleotides and peptide nucleic acids (PNAs) that bind RNA transcript or DNA. For example, a single stranded nucleic acid can target IL-10R or IL-10R ligand (e.g., IL-10) transcript (e.g., mRNA). Oligonucleotides derived from the transcription initiation site of the gene, e.g., between positions −10 and +10 from the start site, are one particular example. Triplex forming antisense can bind to double strand DNA thereby inhibiting transcription of the gene "RNAi" is the use of short antisense RNA sequences that from dsRNA which are cleaved thereby inhibiting expression (see, e.g., Matzke et al., *Nature Rev. Genetics* 6:24 (2005); Kennerdell et al., *Cell* 95:1017 (1998); and Fire et al., *Nature*, 391:806 (1998)). RNA sequences from IL-10R or IL-10R ligand (e.g., IL-10) coding region may therefore be used to inhibit or prevent IL-10R or IL-10R ligand (e.g., IL-10) expression or activity.

Antisense and RNAi can be produced based upon the IL-10R or IL-10R ligand (e.g., IL-10) sequences known in the art. Exemplary IL-10R nucleic acid are as follows:

*Homo sapiens* Interleukin 10 Receptor, Alpha (IL10RA), mRNA (NM 001558) (SEQ ID NO:3)

```
   1 agtcccagcc caagggtagc tggaggcgcg caggccggct ccgctccggc cccggacgat
  61 gcggcgcgcc caggatgctg ccgtgcctcg tagtgctgct ggcggcgctc ctcagcctcc
 121 gtcttggctc agacgctcat gggacagagc tgcccagccc tccgtctgtg tggtttgaag
 181 cagaattttt ccaccacatc ctccactgga cacccatccc aaatcagtct gaaagtacct
 241 gctatgaagt ggcgctcctg aggtatggaa tagagtcctg gaactccatc tccaactgta
 301 gccagaccct gtcctatgac cttaccgcag tgaccttgga cctgtaccac agcaatggct
 361 accggccag agtgcgggct gtggacggca gccggcactc caactggacc gtcaccaaca
 421 cccgcttctc tgtggatgaa gtgactctga cagttggcag tgtgaaccta gagatccaca
 481 atggcttcat cctcgggaag attcagctac ccaggcccaa gatggccccc gcaaatgaca
 541 catatgaaag catcttcagt cacttccgag agtatgagat tgccattcgc aaggtgccgg
 601 gaaacttcac gttcacacac aagaaagtaa aacatgaaaa cttcagcctc ctaacctctg
 661 gagaagtggg agagttctgt gtccaggtga aaccatctgt cgcttcccga agtaacaagg
 721 ggatgtggtc taaagaggag tgcatctccc tcaccaggca gtatttcacc gtgaccaacg
 781 tcatcatctt ctttgccttt gtcctgctgc tctccggagc cctcgcctac tgcctggccc
 841 tccagctgta tgtgcggcgc cgaaagaagc tacccagtgt cctgctcttc aagaagccca
 901 gccccttcat cttcatcagc cagcgtccct cccagagac caagacacc atccacccgc
 961 ttgatgagga ggcctttttg aaggtgtccc cagagctgaa gaacttggac ctgcacggca
1021 gcacagacag tggctttggc agcaccaagc catccctgca gactgaagag cccagttcc
1081 tcctccctga ccctcacccc caggctgaca gaacgctggg aaacggggag cccctgtgc
1141 tgggggacag ctgcagtagt ggcagcagca atagcacaga cagcgggatc tgcctgcagg
```

-continued

```
1201 agcccagcct gagccccagc acagggccca cctgggagca acaggtgggg agcaacagca
1261 ggggccagga tgacagtggc attgacttag ttcaaaactc tgagggccgg gctggggaca
1321 cacaggGtgg ctcggccttg ggccaccaca gtcccccgga gcctgaggtg cctggggaag
1381 aagacccagc tgctgtggca ttccagggtt acctgaggca gaccagatgt gctgaagaga
1441 aggcaaccaa gacaggctgc ctggaggaag aatcgccctt gacagatggc cttggcccca
1501 aattcgggag atgcctggtt gatgaggcag gcttgcatcc accagccctg gccagggct
1561 atttgaaaca ggatcctcta gaaatgactc tggcttcctc aggggcccca acgggacagt
1621 ggaaccagcc cactgaggaa tggtcactcc tggcctttgag cagctgcagt gacctgggaa
1681 tatctgactg gagctttgcc catgaccttg cccctctagg ctgtgtggca gccccaggtg
1741 gtctcctggg cagctttaac tcagacctgg tcaccctgcc cctcatctct agcctgcagt
1801 caagtgagtg actcgggctg agaggctgct tttgatttta gccatgcctg ctcctctgcc
1861 tggaccagga ggagggcccc tggggcagaa gttaggcacg aggcagtctg ggcacttttc
1921 tgcaagtcca ctgggctgg ccccagccag gccctgcagg gctggtcagg gtgtctgggg
1981 caggaggagg ccaactcact gaactagtgc agggtatgtg ggtggcactg acctgttctg
2041 ttgactgggg ccctgcagac tctggcagag ctgagaaggg cagggacctt ctccctccta
2101 ggaactcttt cctgtatcat aaaggattat ttgctcaggg gaaccatggg gctttctgga
2161 gttgtggtga ggccaccagg ctgaagtcag ctcagaccca gacctccctg cttaggccac
2221 tcgagcatca gagcttccag caggaggaag ggctgtagga atggaagctt cagggccttg
2281 ctgctggggt cattttttagg ggaaaaagga ggatatgatg gtcacatggg gaaccctccc
2341 tcatcgggcc tctgggcag gaagcttgtc actggaagat cttaaggtat atatttttctg
2401 gacactcaaa cacatcataa tggattcact gaggggagac aaagggagcc gagaccctgg
2461 atggggcttc cagctcagaa cccatcccctc tggtgggtac ctctggcacc catctgcaaa
2521 tatctccctc tctccaacaa atggagtagc atcccctgg ggcacttgct gaggccaagc
2581 cactcacatc ctcactttgc tgccccacca tcttgctgac aacttccaga gaagccatgg
2641 tttttttgtat tggtcataac tcagccctttc gggcggcctc tgggcttggg caccagctca
2701 tgccagcccc agagggtcag ggttggaggc ctgtgcttgt gtttgctgct aatgtccagc
2761 tacagaccca gaggataagc cactgggcac tgggctgggg tccctgcctt gttggtgttc
2821 agctgtgtga ttttggacta gccacttgtc agagggcctc aatctcccat ctgtgaaata
2881 aggactccac ctttagggga ccctccatgt ttgctgggta ttagccaagc tggtcctggg
2941 agaatgcaga tactgtccgt ggactaccaa gctggcttgt ttcttatgcc agaggctaac
3001 agatccaatg ggagtccatg gtgtcatgcc aagacagtat cagacacagc cccagaaggg
3061 ggcattatgg gccctgcctc cccataggcc atttggactc tgccttcaaa caaaggcagt
3121 tcagtccaca ggcatggaag ctgtgagggg acaggcctgt gcgtgccatc cagagtcatc
3181 tcagccctgc ctttctctgg agcattctga aaacagatat tctggcccag ggaatccagc
3241 catgaccccc acccctctgc caaagtactc ttaggtgcca gtctggtaac tgaactccct
3301 ctggaggcag gcttgaggga ggattcctca gggttccctt gaaagcttta tttatttatt
3361 ttgttcattt atttattgga gaggcagcat tgcacagtga aagaattctg gatatctcag
3421 gagccccgaa attctagctc tgactttgct gtttccagtg gtatgacctt ggagaagtca
3481 cttatcctct tggagcctca gtttcctcat ctgcagaata atgactgact tgtctaattc
```

-continued

```
3541 gtagggatgt gaggttctgc tgaggaaatg ggtatgaatg tgccttgaac acaaagctct
3601 gtcaataagt gatacatgtt ttttattcca ataaattgtc aagaccaca
```

*Homo sapiens* Interleukin 10 Receptor, Beta (IL10RB), mRNA (NM 000628) (SEQ ID NO:4)

```
   1 atctccgctg gttcccggaa gccgccgcgg acaagctctc ccgggcgcgg gcggggtcg
  61 tgtgcttgga ggaagccgcg gaaccccag cgtccgtcca tggcgtggag ccttgggagc
 121 tggctgggtg gctgcctgct ggtgtcagca ttgggaatgg taccacctcc cgaaaatgtc
 181 agaatgaatt ctgttaattt caagaacatt ctacagtggg agtcacctgc ttttgccaaa
 241 gggaacctga ctttcacagc tcagtaccta agttatagga tattccaaga taatgcatg
 301 aatactacct tgacggaatg tgatttctca agtctttcca agtatggtga ccacaccttg
 361 agagtcaggg ctgaatttgc agatgagcat tcagactggg taaacatcac cttctgtcct
 421 gtggatgaca ccattattgg accccctgga atgcaagtag aagtacttgc tgattcttta
 481 catatgcgtt tcttagcccc taaaattgag aatgaatacg aaacttggac tatgaagaat
 541 gtgtataact catggactta taatgtgcaa tactggaaaa acggtactga tgaaaagttt
 601 caaattactc cccagtatga ctttgaggtc tcagaaacc tggagccatg acaacttat
 661 tgtgttcaag ttcgagggtt tcttcctgat cggaacaaag ctggggaatg gagtgagcct
 721 gtctgtgagc aaacaaccca tgacgaaacg gtcccctcct ggatggtggc cgtcatcctc
 781 atggcctcgg tcttcatggt ctgcctggca ctcctcggct gcttcgcctt gctgtggtgc
 841 gtttacaaga agacaaagta cgccttctcc cctaggaatt ctcttccaca gcacctgaaa
 901 gagtttttgg gccatcctca tcataacaca cttctgtttt tctcctttcc attgtcggat
 961 gagaatgatg tttttgacaa gctaagtgtc attgcagaag actctgagag cggcaagcag
1021 aatcctggtg acagctgcag cctcgggacc ccgcctgggc aggggcccca aagctaggct
1081 ctgagaagga acacactcg gctgggcaca gtgacgtact ccatctcaca tctgcctcag
1141 tgagggatca gggcagcaaa caagggccaa gaccatctga gccagcccca catctagaac
1201 tcccagaccc tggacttagc caccagagag ctacatttta aaggctgtct tggcaaaaat
1261 actccatttg ggaactcact gccttataaa ggctttcatg atgttttcag aagttggcca
1321 ctgagagtgt aattttcagc cttttatatc actaaaataa gatcatgttt taattgtgag
1381 aaacagggcc gagcacagtg gctcacgcct gtaataccag caccttagag gtcgaggcag
1441 gcggatcact tgaggtcagg agttcaagac cagcctggcc aatatggtga aacccagtct
1501 ctactaaaaa tacaaaaatt agctaggcat gatggcgcat gcctataatc ccagctactc
1561 gagtgcctga ggcaggagaa ttgcatgaac ccgggaggag gaggaggagg ttgcagtgag
1621 ccgagatagc ggcactgcac tccagcctgg gtgacaaagt gagactccat ctcaaaaaaa
1681 aaaaaaaaa aaattgtgag aaacagaaat acttaaaatg aggaataaga atggagatgt
1741 tacatctggt agatgtaaca ttctaccaga ttatggatgg actgatctga aaatcgaccc
1801 caactcaagg gtggtcagct caatgctaca cagagcacgg acttttggat tctttgcagt
1861 actttgaatt tattttttcta cctatatatg ttttatatgc tgctggtgct ccattaaagt
1921 tttactctgt gttgc
```

Exemplary IL-10R Ligand (e.g., IL-10) Nucleic Acid is as Follows:

*Homo sapiens* Interleukin 10 (IL10), mRNA (NM 000572) (SEQ ID NO:5)

```
   1 acacatcagg ggcttgctct tgcaaaacca aaccacaaga cagacttgca aaagaaggca
  61 tgcacagctc agcactgctc tgttgcctgg tcctcctgac tggggtgagg gccagcccag
 121 gccagggcac ccagtctgag aacagctgca cccacttccc aggcaacctg cctaacatgc
 181 ttcgagatct ccgagatgcc ttcagcagag tgaagacttt ctttcaaatg aaggatcagc
 241 tggacaactt gttgttaaag gagtccttgc tggaggactt taagggttac ctgggttgcc
 301 aagccttgtc tgagatgatc cagttttacc tggaggaggt gatgcccaa gctgagaacc
 361 aagacccaga catcaaggcg catgtgaact ccctggggga gaacctgaag accctcaggc
 421 tgaggctacg gcgctgtcat cgatttcttc cctgtgaaaa caagagcaag gccgtggagc
 481 aggtgaagaa tgcctttaat aagctccaag agaaaggcat ctacaaagcc atgagtgagt
 541 ttgacatctt catcaactac atagaagcct acatgacaat gaagatacga aactgagaca
 601 tcagggtggc gactctatag actctaggac ataaattaga ggtctccaaa atcggatctg
 661 gggctctggg atagctgacc cagcccttg agaaaccta ttgtacctct cttatagaat
 721 atttattacc tctgatacct caaccccat ttctatttat ttactgagct tctctgtgaa
 781 cgatttagaa agaagcccaa tattataatt tttttcaata tttattattt tcacctgttt
 841 ttaagctgtt tccatagggt gacacactat ggtatttgag tgttttaaga taaattataa
 901 gttacataag ggaggaaaaa aaatgttctt tggggagcca acagaagctt ccattccaag
 961 cctgaccacg ctttctagct gttgagctgt ttcccctgac ctccctctaa tttatcttgt
1021 ctctgggctt ggggcttcct aactgctaca aatactctta ggaagagaaa ccagggagcc
1081 cctttgatga ttaattcacc ttccagtgtc tcggagggat tcccctaacc tcattcccca
1141 accacttcat tcttgaaagc tgtggccagc ttgttattta taacaaccta aatttggttc
1201 taggccgggc gcggtggctc acgcctgtaa tcccagcact ttgggaggct gaggcgggtg
1261 gatcacttga ggtcaggagt tcctaaccag cctggtcaac atggtgaaac cccgtctcta
1321 ctaaaaatac aaaaattagc cgggcatggt ggcgcgcacc tgtaatccca gctacttggg
1381 aggctgaggc aagagaattg cttgaaccca ggagatggaa gttgcagtga gctgatatca
1441 tgcccctgta ctccagcctg ggtgacagag caagactctg tctcaaaaaa taaaaataaa
1501 aataaatttg gttctaatag aactcagttt taactagaat ttattcaatt cctctgggaa
1561 tgttacattg tttgtctgtc ttcatagcag attttaattt tgaataaaata aatgtatctt
1621 attcacatc
```

Dominant negative IL-10R or IL-10R ligand (e.g., IL-10) can directly or indirectly modulate IL-10R or FL-10R ligand (e.g., IL-10) activity or expression. For example, soluble FL-10R is capable of binding IL-10R ligand (e.g., IL-10) but does not transmit a signal. Dominant negative IL-10R ligand (e.g., IL-10) is capable of binding IL-10R but does not transmit a signal. Such forms of IL-10R or IL-10R ligand (e.g., IL-10) are therefore useful as antagonists of IL-10R or IL-10R ligand (e.g., IL-10).

The term "subject," also referred to as "patient," means an animal, typically mammalian animal, such as but not limited to non-human primates (apes, gibbons, gorillas, chimpanzees, orangutans, macaques), domestic animals (dogs and cats), a farm animals (chickens, ducks, horses, cows, goats, sheep, pigs), experimental animal (mouse, rat, rabbit, guinea pig) and humans. Subjects include animal models, for example, a model of viral infection (e.g., LCMV), reactivation or pathogenesis. Subjects include naturally occurring or non-naturally occurring mutated or non-human genetically engineered (e.g., transgenic or knockout) animals.

Subjects include animals with or at risk of having a chronic or acute viral infection/reactivation or pathogenesis, or a physiological condition, disorder, illness, disease or symptom caused by or associated with viral infection/reactivation or pathogenesis. Subjects can be any age. For example, a subject (e.g., human) can be a newborn, infant, toddler, child, teenager, adult, or elderly e.g., 50 years or older.

Subjects include those in need of or those that may benefit from a method embodiment, e.g., in need of or benefit from a therapeutic or prophylactic treatment method. A subject is considered to be in need of a method of the invention where a method may provide an objective or subjective benefit to the subject. Various benefits or improvement provided to a subject by various methods embodiments are as set forth herein and known in the art for viral infections and associated physiological conditions, disorders, illnesses, diseases and symptoms.

Subjects appropriate for treatment also include those at risk of viral infection or pathogenesis or at risk of having or developing an viral infection. Candidate subjects therefore include subjects that have been exposed to or contacted with virus, or are at risk of exposure to or contact with virus, regardless of the type, timing or extent of exposure or contact. The invention methods are therefore applicable to a subject who is at risk of virus infection, but has not yet been exposed to virus, contacted with virus or diagnosed with a virus infection/reactivation or pathogenesis.

"At risk" subjects include those having risk factors associated with viral infection, such as an acute exposure to or contact with an infectious agent (e.g., herpesvirus, poxvirus, arenavirus, HIV, etc.). Risk factors include gender, lifestyle occupation (military, medical and clinical personnel), environmental factors (exposure), family history (mother to fetus or newborn transmission, etc.), genetic predisposition, etc. For example, a subject at risk for a herpesvirus or HIV infection is a subject engaging in sexual activity with a partner that has a viral infection (e.g., herpesvirus or HIV), or a fetus or newborn whose mother has a viral infection (e.g., herpesvirus or HIV). Subjects at risk include those that may be in an area, such as deployed military personnel, where exposure to a biological weapon such as a poxvirus, for example, is possible.

At risk subjects appropriate for treatment include subjects exposed to other subjects having viral infection, or where the risk of viral infection is increased due to changes in virus infectivity or cell tropism, immunological susceptibility (e.g., an immunocompromised subject), or environmental risk. At risk subjects appropriate for treatment therefore include human subjects exposed to or at risk of exposure to other humans that have a viral infection.

Appropriate subjects include those having a viral infection/reactivation or pathogenesis or having any physiological condition, disorder, illness, disease or symptom caused by or associated with the virus. Target subjects therefore include subjects that have been infected or diagnosed with virus, or that have developed one or more physiological conditions, disorders, illness, diseases and symptoms caused by or associated with virus infection/reactivation or pathogenesis (e.g., illness) as set forth herein or known in the art, regardless of the virus type, timing or degree of onset, progression, severity, frequency, duration of any virus infection/reactivation, or pathogenesis. Subjects that have not been diagnosed with an autoimmune disease or an inflammatory disease are appropriate since it is possible that an antagonist of IL-10R or IL-10R ligand (e.g., IL-10) activity or expression may exacerbate an autoimmune disease or inflammatory disease to the extent that they may outweigh the anti-viral benefits.

Embodiments include pharmaceutical compositions/formulations, which are useful for contact or administration to a subject, in vivo or ex vivo. Pharmaceutical compositions and formulations include carriers or excipients for administration to a subject. As used herein the terms "pharmaceutically acceptable" and "physiologically acceptable" mean a biologically compatible formulation, gaseous, liquid or solid, or mixture thereof, which is suitable for one or more routes of administration, in vivo delivery or contact. A formulation is compatible in that it does not destroy activity of an active ingredient therein, for example, an antagonist of IL-10R or IL-10R ligand (e.g., IL-10) expression or activity, or induce adverse side effects that far outweigh any prophylactic or therapeutic effect or benefit.

Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

The formulations may, for convenience, be prepared or provided as a unit dosage form. Preparation techniques include bringing into association the active ingredient and a pharmaceutical carrier(s) or excipient(s). In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient (e.g., antagonist of IL-10R or IL-10R ligand (e.g., IL-10) expression or activity) in a free-flowing form such as a powder or granules, optionally mixed with a binder, lubricant, inert diluent, preservative, surface-active or dispersing agent. Molded tablets may be produced by molding, in a suitable apparatus, a mixture of powdered compound (e.g., antagonist of IL-10R or IL-10R ligand (e.g., IL-10) expression or activity) moistened with an inert liquid diluent. The tablets may optionally be coated or scored and may be formulated so as to provide a slow or controlled release of the active ingredient therein.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Supplementary active compounds (e.g., preservatives, antioxidants, antimicrobial agents including biocides and biostats such as antibacterial, antiviral and antifungal agents) can also be incorporated into the compositions. Preservatives and other additives include, for example, antimicrobials, antioxidants, chelating agents and inert gases (e.g., nitrogen). Pharmaceutical compositions may therefore include preservatives, antimicrobial agents, anti-oxidants, chelating agents and inert gases.

Preservatives can be used to inhibit microbial growth or increase stability of the active ingredient thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include, antibacterial, antiviral, antifungal and antiparasitics. Antimicrobials include agents and compounds that kill or destroy (-cidal) or inhibit (-static) contamination by or growth, infectivity, replication, proliferation, reproduction of the microbial organism.

Exemplary antibacterials (antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, chlortetracycline, minocycline, and tetracycline), aminoglycosides (e.g., amikacin, gentamycin, kanamycin, neomycin, streptomycin, netilmicin, paromomycin and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, vancomycin, aztreonam, clavulanic acid, imipenem, polymyxin, bacitracin, amphotericin and nystatin.

Particular non-limiting classes of anti-virals include reverse transcriptase inhibitors; protease inhibitors; thymidine kinase inhibitors; sugar or glycoprotein synthesis inhibitors; structural protein synthesis inhibitors; nucleoside analogues; and viral maturation inhibitors. Specific non-limiting examples of anti-virals include those set forth above and, nevirapine, delavirdine, efavirenz, saquinavir, ritonavir, indinavir, nelfinavir, amprenavir, zidovudine (AZT), stavudine (d4T), larnivudine (3TC), didanosine (DDI), zalcitabine (ddC), abacavir, acyclovir, penciclovir, valacyclovir, ganciclovir, 1,-D-ribofuranosyl-1,2,4-triazole-3 carboxamide, 9->2-hydroxy-ethoxy methylguanine, adamantanamine, 5-iodo-2'-deoxyuridine, trifluorothymidine, interferon and adenine arabinoside.

Exemplary antifungals include agents such as benzoic acid, undecylenic alkanolamide, ciclopiroxolamine, polyenes, imidazoles, allylamine, thicarbamates, amphotericin B, butylparaben, clindamycin, econaxole, ammolfine, butenafine, naftifine, terbinafine, ketoconazole, elubiol, econazole, econaxole, itraconazole, isoconazole, miconazole, sulconazole, clotrimazole, enilconazole, oxiconazole, tioconazole, terconazole, butoconazole, thiabendazole, voriconazole, saperconazole, sertaconazole, fenticonazole, posaconazole, bifonazole, fluconazole, flutrimazole, nystatin, pimaricin, amphotericin B, flucytosine, natamycin, tolnaftate, mafenide, dapsone, caspofungin, actofunicone, griseofulvin, potassium iodide, Gentian Violet, ciclopirox, ciclopirox olamine, haloprogin, ketoconazole, undecylenate, silver sulfadiazine, undecylenic acid, undecylenic alkanolamide and Carbol-Fuchsin.

Pharmaceutical compositions can optionally be formulated to be compatible with a particular route of administration. Thus, pharmaceutical compositions include carriers (excipients, diluents, vehicles or filling agents) suitable for administration by various routes and delivery, locally, regionally or systemically, ex vivo or in vivo.

Exemplary routes of administration for contact or ex vivo or in vivo delivery include inhalation, respiration, intubation, intrapulmonary instillation, oral (buccal, sublingual, mucosal), intrapulmonary, rectal, vaginal, intrauterine, intradermal, topical, dermal, parenteral (e.g., subcutaneous, intramuscular, intravenous, intradermal, intraocular, intratracheal and epidural), intranasal, intrathecal, intraarticular, intracavity, transdermal, iontophoretic, ophthalmic, optical (e.g., corneal), intraglandular, intraorgan, intralymphatic.

Formulations suitable for parenteral administration include aqueous and non-aqueous solutions, suspensions or emulsions of the compound, which may include suspending agents and thickening agents, which preparations are typically sterile and can be isotonic with the blood of the intended recipient. Non-limiting illustrative examples of aqueous carriers include water, saline (sodium chloride solution), dextrose (e.g., Ringer's dextrose), lactated Ringer's, fructose, ethanol, animal, vegetable or synthetic oils. Examples of non-aqueous solvents are propylene glycol, polyethylene glycol, vegetable oils such as olive oil, and injectable organic esters such as ethyl oleate. Intravenous vehicles include fluid and nutrient replenishers, electrolyte replenishers (such as those based on Ringer's dextrose). The formulations may be in unit-dose or multi-dose kits, for example, ampules and vials, and may be stored in a freeze-dried (lyophilized) condition requiring addition of a sterile liquid carrier, for example, water for injections.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, pastes, lotions, oils or creams as generally known in the art.

For topical administration, for example, to skin, pharmaceutical compositions typically include ointments, creams, lotions, pastes, gels, sprays, aerosols or oils. Carriers which may be used include Vaseline, lanolin, polyethylene glycols, alcohols, transdermal enhancers, and combinations thereof. An exemplary topical delivery system is a transdermal patch containing an active ingredient (e.g., antagonist of IL-10R or IL-10R ligand (e.g., IL-10) expression or activity).

For oral administration, pharmaceutical-compositions include capsules, cachets, lozenges, tablets or troches, as powder or granules. Oral administration formulations also include a solution or a suspension (e.g., aqueous liquid or a non-aqueous liquid; or as an oil-in-water liquid emulsion or a water-in-oil emulsion).

For rectal administration, pharmaceutical compositions can be included as a suppository with a suitable base comprising, for example, cocoa butter or a salicylate. For vaginal administration, pharmaceutical compositions can be included as pessaries, tampons, creams, gels, pastes, foams or spray formulations containing in addition to the active ingredient (e.g., antagonist of IL-10R or IL-10R ligand (e.g., IL-10) expression or activity) a carrier, examples of appropriate carriers which are known in the art.

Pharmaceutical formulations and delivery systems appropriate for the compositions and methods of the invention are known in the art (see, e.g., *Remington: The Science and Practice of Pharmacy* (2003) 20$^{th}$ ed., Mack Publishing Co., Easton, Pa.; *Remington's Pharmaceutical Sciences* (1990) 18$^{th}$ ed., Mack Publishing Co., Easton, Pa.; *The Merck Index* (1996) 12$^{th}$ ed., Merck Publishing Group, Whitehouse, N.J.; *Pharmaceutical Principles of Solid Dosage Forms* (1993), Technonic Publishing Co., Inc., Lancaster, Pa.; *Ansel* and *Stoklosa, Pharmaceutical Calculations* (2001) 11$^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

Embodiments including pharmaceutical formulations can be packaged in unit dosage forms for ease of administration and uniformity of dosage. A "unit dosage form" as used herein refers to a physically discrete unit suited as unitary dosages for treatment or administration; each unit containing a predetermined quantity of compound optionally in association with a pharmaceutical carrier (excipient, diluent, vehicle or filling agent) which, when administered in one or more doses, is calculated to produce a desired effect (e.g., a desired effect or benefit). Unit dosage forms can contain a daily dose or unit, daily sub-dose, or an appropriate fraction thereof, of an administered molecule (e.g., antagonist of IL-10R or IL-10R ligand (e.g., IL-10) expression or activity). Unit dosage forms also include, for example, capsules, troches, cachets, lozenges, tablets, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Unit dosage forms further include compounds for transdermal administration, such as "patches" that contact with the epidermis of the subject for an extended or brief period of time. The individual unit dosage forms can be included in multi-dose kits or containers. Pharmaceutical formulations can be packaged in single or multiple unit dosage forms for ease of administration and uniformity of dosage.

Methods embodiments include contact or administration in vitro, ex vivo and in vivo at any frequency as a single bolus or multiple dose e.g., one, two, three, four, five, or more times hourly, daily, weekly, monthly or annually or between about 1 to 10 days, weeks, months, or for as long as appropriate. Exemplary frequencies are typically from 1-7 times, 1-5 times, 1-3 times, 2-times or once, daily, weekly or monthly. Timing of contact, administration ex vivo or in vivo delivery can be dictated by the physiological condition, disorder, illness, disease or symptom to be treated. For example, an amount can be administered to the subject substantially contemporaneously with, or within about 1-60 minutes, hours or days of the onset of a exposure or viral infection/reactivation or a condition, disorder, illness, disease or symptom caused by or associated with viral infection/reactivation.

Compositions and methods embodiments include contact or administration in vitro, ex vivo or in vivo. Compositions and methods embodiments may be practiced via systemic, regional or local administration, by any route. Compositions and methods embodiments may be administered as a single or multiple doses to provide the intended effect.

A subject may be administered in single bolus or in divided/metered doses, which can be adjusted to be more or less according to the various considerations set forth herein and known in the art. Doses may vary depending upon the viral infection/reactivation or a physiological condition, disorder, illness, disease or symptom thereof to be treated, the onset, progression, severity, frequency, duration, probability of or susceptibility of the infection or physiological condition, disorder, illness, disease or symptom to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history). Dose amount, frequency or duration may be increased or reduced, as indicated by the clinical outcome or beneficial effect desired, status of the infection or a physiological condition, disorder, illness, disease or symptom, any adverse side effects of the treatment or therapy, etc. For example, once virus control or a particular endpoint is achieved, for example, dose amount, frequency or duration can be reduced.

The skilled artisan will appreciate the factors that may influence the dosage, frequency and timing required to provide an amount sufficient or effective for treatment.

For therapeutic treatment, a method is performed as soon as practical, typically within 0-72 hours or days within or after a subject is exposed to, contacted or manifests, or is diagnosed with a viral infection/reactivation, or an associated physiological condition, disorder, illness, disease or symptom. For prophylactic treatment, a method is performed immediately or within 0-72 after suspected contact with, or 0-4 weeks, e.g., 1-3 days or weeks, prior to an anticipated or potential virus infection/reactivation, exposure or contact, or manifestation of a physiological condition, disorder, illness, disease or symptom caused by or associated with viral infection/reactivation.

Doses can be based upon current existing treatment protocols, empirically determined, determined using animal disease models or optionally in human clinical studies. For example, initial study doses can be based upon animal studies, such as primates, and the amount of compound administered to achieve a prophylactic or therapeutic effect or benefit. The dose can be adjusted according to the mass of a subject, and will generally be in a range from about 25-250, 250-500, 500-1000, 1000-2500 or 2500-5000,5000-25,000,5000-50,000, 50,000-100,000 pg/kg; from about 0.1-1 ug/kg, 1-10 ug/kg, 10-25 ug/kg, 25-50 ug/kg, 50-100 ug/kg, 100-500 ug/kg, 500-1,000 ug/kg, 1-5 mg/kg, 5-10 mg/kg, 10-20 mg/kg, 20-50 mg/kg, 50-100 mg/kg, 100-250 mg/kg, 250-500 mg/kg, or more, of subject body weight, two, three, four, or more times per hour, day, week, month or annually. Of course, doses can be more or less, as appropriate, for example, 0.00001 mg/kg of subject body weight to about 10,000.0 mg/kg of subject body weight, about 0.001 mg/kg, to about 100 mg/kg, about 0.01 mg/kg, to about 10 mg/kg, or about 0.1 mg/kg, to about 1 mg/kg of subject body weight over a given time period, e.g., 1, 2, 3, 4, 5 or more hours, days, weeks, months, years.

The invention provides, among other things, kits including an antagonist of IL-10R or an antagonist of IL-10R ligand (e.g., IL-10) expression or activity, combination compositions thereof and pharmaceutical compositions/formulations thereof, packaged into a suitable packaging material. In one embodiment, a kit includes packaging material, antagonist of IL-10R or an antagonist of IL-10R ligand (e.g., IL-10) expression or activity, and instructions. In various aspects, the instructions are for treating a subject having or at risk of having a viral infection.

The term "packaging material" refers to a physical structure housing one or more components of the kit. The packaging material can maintain the components sterilely, and can be made of material commonly used for such purposes (e.g., paper, corrugated fiber, glass, plastic, foil, ampules, vials, tubes, etc.). A kit can contain a plurality of components, e.g., two or more antagonists of IL-10R or IL-10R ligand (e.g., IL-10) expression or activity, alone or in combination with an another treatment or drug (e.g., an anti-viral or immune enhancing compound or agent), optionally sterile.

A kit optionally includes a label or insert including a description of the components (type, amounts, doses, etc.), instructions for use in vitro, in vivo, or ex vivo, and any other components therein. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacturer location and date, expiration dates.

Labels or inserts can include information on a physiological condition, disorder, illness, disease or symptom, for which a kit component may be used. Labels or inserts can include instructions for a clinician or subject for using one or more of the kit components in a method, treatment protocol or therapeutic/prophylactic regimen, including the methods embodiments. Instructions can include amounts of compound, frequency or duration of administration, and instructions for carrying out any of the methods, treatment protocols or prophylactic or therapeutic regimes described herein.

Labels or inserts can also include information on any desired effect or benefit, or adverse side effects, a kit component may provide, such as a prophylactic or therapeutic effect or benefit. For example, a label or insert could provide a description of reducing, decreasing, inhibiting, ameliorating or preventing onset, severity, duration, progression, frequency or probability of viral infection/reactivation or a physiological condition, disorder, illness, disease or symptom caused by or associated with viral infection/reactivation.

Labels or inserts can further include information on potential adverse side effects. Labels or inserts can further include warnings to the clinician or subject regarding situations or conditions where a subject should stop or reduce use of a particular kit component. Adverse side effects could also occur when the subject has, will be or is currently taking one or more other medications that may be incompatible with treatment, or the subject has, will be or is currently undergoing another treatment protocol or therapeutic regimen which would be incompatible with treatment and, therefore, labels or inserts could include information regarding such side effects or incompatibilities.

Invention kits can moreover include a buffering agent, or a preservative or a stabilizing agent in a pharmaceutical formulation containing a compound of the invention. Each component of the kit can be enclosed within an individual container and all of the various containers can be within a single package. Invention kits can be designed for cold storage.

Invention kits can additionally include components, such as devices for practicing a method of the invention or administering an antagonist of IL-10R or IL-10R ligand (e.g., IL-10) expression or activity, to a subject, ex vivo or in vivo. The device can be a delivery device, such as a ampule, vial or syringe, a compressible (e.g., squeezable) tube or dermal patch for mucosal, skin/dermis or corneal delivery, or an aerosol delivery device.

The invention provides, among other things, methods of identifying and screening for agents for treating viral infection/reactivation. In one embodiment, a method includes contacting a test agent or sample containing a test agent with IL-10R or IL-10R ligand (e.g., IL-10); ascertaining the presence of binding between the test agent and L-10R or IL-10R ligand (e.g., IL-10), or ascertaining the inhibition of binding between L-10R and IL-10R ligand (e.g., IL-10), or ascertaining the inhibition of IL-10 signaling. A test agent that binds L-10R or IL-10R ligand (e.g., IL-10), inhibits binding between L-10R and IL-10R ligand (e.g., IL-10) or signaling is candidate agent for treating a viral infection/reactivation. In another embodiment, a method includes contacting a test agent or sample containing a test agent with nucleic acid encoding IL-10R or IL-10R ligand (e.g., IL-10) and ascertaining the presence of binding between the test agent and nucleic acid encoding L-10R or IL-10R ligand (e.g., IL-10). A test agent that binds to nucleic acid encoding L-10R or IL-10R ligand (e.g., IL-10) is candidate agent for treating a viral infection/reactivation.

In various aspects, the test agent is a polypeptide, such as an antibody (e.g., polyclonal or monoclonal), subsequences and fragments thereof (e.g., Fab, Fab', F(ab')$_2$, Fv, Fd, single-chain Fv (scFv), disulfide linked Fv, light chain variable (VL) and heavy chain variable (VH)). Such antibodies include, for example, mammalian, primatized, humanized and fully human forms. Test agents further include nucleic acids and small molecules. Target IL-10R and IL-10R ligand (e.g., IL-10) include mammalian (e.g., human) polypeptide and nucleic acid sequences.

The invention provides, among other things, methods of identifying a subject in need of a treatment with an antagonist of IL-10R or IL-10R ligand (e.g., IL-10) expression or activity. In one embodiment, a method includes determining an amount of IL-10 produced in a subject with or at risk of a viral infection/reactivation or pathogenesis. An amount of IL-10 produced in the subject considered to be undesirably or abnormally high indicates that the subject is in need of treatment with an antagonist of IL-10R or IL-10R ligand (e.g., IL-10) expression or activity.

The invention provides, among other things, methods of screening for and identifying a subject that is a candidate for treatment with an antagonist of IL-10R or IL-10R ligand (e.g., IL-10) expression or activity. In one embodiment, a method includes providing a biological sample from a subject; and assaying the sample for the presence of IL-10. An amount of IL-10 considered to be undesirably or abnormally high identifies the subject as in need of a treatment with an antagonist of IL-10R or IL-10R ligand (e.g., IL-10) expression or activity.

Unless otherwise defined, all technical and scientific terms used herein have the same meaning as commonly understood by one of ordinary skill in the art to which this invention relates. Although methods and materials similar or equivalent to those described herein can be used in the practice or testing of the present invention, suitable methods and materials are described herein.

All publications, patents and other references cited herein are incorporated by reference in their entirety. In case of conflict, the present specification, including definitions, will control.

As used herein, the singular forms "a", "and," and "the" include plural referents unless the context clearly indicates otherwise. Thus, for example, reference to "antagonist of IL-10R or IL-10R ligand (e.g., IL-10)" includes a plurality of antagonists that antagonize IL-10R or IL-10R ligand (e.g., IL-10) expression or activity. Reference to "a physiological condition, disorder, illness, disease or symptom" includes a plurality of physiological conditions, disorders, illness, diseases or symptoms. Of course, this does not preclude limiting certain embodiments of the invention to specific antagonists of IL-10R or IL-10R ligand (e.g., IL-10) expression or activity, particular physiological conditions, disorders, illness, diseases or symptoms, particular subjects, etc., using appropriate language.

The invention is generally disclosed herein using affirmative language to describe the numerous embodiments. The invention also includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless expressly or inherently disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes various materials and methods.

Mice and Virus: BALB/c and C57BL/6 (B6) mice (6 week old) were purchased from The Jackson laboratory (Maine, USA). LCMV-GP61-80-specific CD4$^+$ TCR tg SMARTA mice (Oxenius et al., *Eur J Immunol* 28:390 (1998)) were obtained from La Jolla Institute for Allergy and Immunology and housed under specific pathogen-free conditions. LCMV plaques were purified three times on Vero cells and viral stocks prepared by a single passage on BHK-1 cells. Age-matched BALB/c mice were infected intravenous (i.v.) with a single dose of either 2×10$^6$ PFU LCMV Clone 13 (Cl13), 2×10$^6$ LCMV Armstrong (Arm) or an interparenteral (i.p.) dose of 1×10$^5$ PFU LCMV Arm per mouse. For IL-10 blocking studies, mice were injected i.p. with 250 µg anti-mouse IL-10R (1B1.3a, Becton Dickinson Pharmingen, CA, USA), mAb or isotype control Ab (CD210) (rat IgG1, (BD Pharmingen, CA, USA) at day 0, 7 and 14 post infection. Mice were weighed every 2-3 days and data presented as difference in weight (g/mouse) compared to age-matched non-infected BALB mice (FIGS. 1 and 2). All animal studies were approved by institutional and governmental review boards.

Plague assay: Kidney and livers were quik-frozen, weighed and homogenized. Briefly, three different dilutions of homogenized organ were prepared and triplicates were set up. Dilutions were incubated at 37° C., 5% $CO_2$ for 1 hour with Vero cell monolayers grown in 6-well plates (Costar, Cambridge, Mass.). The plates were then overlaid with 1% agarose in minimal essential medium 199 (Invitrogen, NY, USA) containing 10% fetal calf serum (FCS, HyClone, Utah, USA) and incubated at 37° C., 5% $CO_2$ for 5 days. The wells were treated with 25% formaldehyde and stained with 0.1% crystal violet for 2 minutes. The agarose overlay was removed, infectious centers were counted and the counts were averaged. Additionally, viral LCMV stock were used as positive controls.

RT-PCR: Frozen kidney and livers were weighed and homogenized. RNA was isolated from 50 µl serum or 10 mg tissue samples using RNAqueous (Ambion, Austin, Tex.). All samples were frozen at −80° C. until RNA extraction. RNA was eluted in a volume of 20 µl and purified RNA was frozen at −80 C until use. 10 µl of RNA was used in a 20 µl cDNA reaction with SuperScript III Reverse Transcriptase (Invitrogen, Carlsbad, Calif.) and a gene specific primer (GP-R, GCAACTGCTGTGTTCCCGAAAC" (SEQ ID NO.:6)) 5 µl of cDNA was then used as template for a 25 µl quantitative real time PCR (QPCR) reaction on a GeneAmp 5700 (ABI, Redwood City, Calif.), using primers GP-R and GP-F (CAT-TCACCTGGACTTTGTCAGACTC (SEQ ID NO.:7)). A standard curve was generated using pSG5-GP plasmid (Lee et al., *J Virol* 76:6393 (2002). Data were analyzed using Graphpad Prism linear regression analysis.

IL-10R Antibodies and Screening Assays: IL-10R antibody clone 1B1.34 (BD Biosciences, Pharmingen Division, Cat. No. 550012), which reacts with the extracellular region of mouse CD210 receptor, was used in the studies. IL-10R antibodies also include an IL-10R antibody producing hybridoma 1B1.2 (DNAX), and sf 21-derived rmIL-10 sRα, an anti-mouse IL-10R(R & D Systems, Cat. No. AF-474-NA), reported to neutralize IL-10 activity in vitro.

In order to detect L-10R binding antibodies, a FACS or an ELISA analysis could be performed. Antibodies that bind IL-10R can subsequently be screened for antagonist activity, for example, by assaying for signaling, such as activation of STAT 3 or STAT1 in a responder cell line (as described, for example, in Donnelly et al., *J. Leukoc Biol* 76:314 (2004)).

Quantification of IL-10: Quantification of cytokines in cell culture supernatant was performed by sandwich enzyme-linked immunosorbent assay (ELISA). Splenocytes were counted and total number/spleen calculated. 2–5×10$^6$ splenocytes were incubated for 48 hours in complete RPMI 1640 (Invitrogen, GmbH, Germany) supplemented with 10% fetal calf serum (Sigma-Aldrich, MO, USA), L-glutamine (2 mM, Sigma-Aldrich, MO, USA), 2-β-mercaptoethanol (50 um, Sigma-Aldrich, MO, USA), and Hepes (5 mM, Sigma-Aldrich, MO, USA) in 24-well plates (Invitrogen, NY, USA). After washing and blocking, supernatant was removed at the indicated time points and ELISA was performed in accordance with the manufacturer's recommendations and standardized with murine recombinant cytokine BD Pharmingen, CA, USA). Plates were further incubated with matched biotinylated detection antibodies and a streptavidin-peroxidase conjugate. For color reaction $H_2O_2$-activated 2,2'-Azino-di-[3-ethylbenzthiazolin-6-sulfonic acid] (ABTS; Sigma-Aldrich, MO, USA) solution was added. Plates were read at 405 nm (Spectra Max 250, Molecular Devices, CA, USA). The sensitivity of the IL-10 ELISA was 10 pg/ml. Data shown is concentration of IL-10 (pg/ml) per 1×10$^6$ cells.

Intracellular cytokine staining, cell surface staining, flow cytometry and isolation of IL-10-producing cells: To detect the cytokine-producing cell subsets, splenocytes were incubated for 5 hours in complete RPMI 1640 with Brefeldin A (Sigma, Mo., USA), with LCMV infected irradiated at 37° C. Cells were resuspended in staining buffer containing 1% FCS and 0.2% $NaN_3$, labeled with anti-CD4, anti-CD8, fixed in 1% paraformaldehyde, and permeabilized with 0.1% saponin buffer. Intracellular staining was performed with fluorescent antibodies to IL-10, IFN-γ, TNF-α, or isotype controls (All antibodies were from BD Pharmingen, CA, USA). Events were acquired using a FACSCalibur™ flow cytometer and analyzed using CellQuest™ software (Beckton Dickinson and Co) 10,000-20,000 events were acquired and live cells were gated based on forward/side scatter properties. When analyzing CD11c+ positive subsets CD3− expressing cells were gated out to avoid contamination of previously reported expression of myeloid markers by T cells (McFarland et al., *J Immunol* 149:1326 (1992), Lin et al., *Eur J Immunol* 33:2736 (2003)) and expression of the indicated cell surface molecules was detected on CD11c and CD8α$^{+/−}$ cells. Results are depicted as number of CD11c$^+$CD8α$^{+/−}$ cells which was calculated by relating the frequency of the cell subsets with the overall number of cells per spleen. IL-10-secreting cells were isolated and enriched using MACS (Miltenyi Biotech, CA, USA) mouse IL-10 cell enrichment kit according to the manufacturer's recommendation. Briefly, cells were re-stimulated for 5 hours with LCMV virus. Upon antigen stimulation IL-10 secreting cells were captured with a mouse IL-10 catch reagent followed by labeling of cells with a PE-conjugated IL-10 detection antibody. Lastly, cells were magnetically labeled with anti-PE microbeads and isolated using MS or LS columns and appropriate MACS magnetic cell separators. IL-10 secreting cell subsets were identified by labeling cells with antibodies to CD4, CD8, CD11c, and CD11 b and analyzed by FACS.

Sorting of CD11c$^+$CD8α$^-$ and CD11c$^+$CD8α$^+$ cells: Splenocytes from mice infected 2, 7 or 15 days earlier with LCMV Arm or LCMV CI13 were incubated with RPMI 1640 complete medium containing collagenase D (0.5 mg/ml: Sigma-Aldrich, MO, USA) at 37° C., 5% $CO_2$ for 30 minutes. EDTA was added (0.01 M) to disrupt T cell-DC complexes. Next, cells were depleted of CD3-expressing cells (Dynal CD3-beads, Dynal, Oslo, Norway), incubated with CD11c microbeads (Miltenyi Biotech, CA, USA) and positively selected using MACS columns. The enriched CD11c$^+$ cells were labeled with APC-conjugated CD11c and PE-conjugated CD8α mAb (BD Pharmingen, CA, USA) and sorted using an Aria cell sorter (Becton Dickinson) into CD8α$^-$ and CD8α$^+$ CD11c$^+$ cells. $1.5 \times 10^5$ sorted CD11c+ cells were then placed in 96 well plates in complete RPMI 1640 medium and irradiated with 2,900 Rad. Assessment of the polarization of antigen-specific CD4$^+$ T cells by DCs ex vivo was adapted from a previously described method (Filippi et L., *J Exp Med* 198:201 (2003)). LCMV $GP_{61-80}$-specific CD4$^+$ T cells isolated from TCR tg SMARTA mice (Oxenius et al., *Eur J Immunol* 28:390 (1998)) were purified using CD4 Dynal beads, and $6 \times 10^5$ cells were added to DCs in the presence or absence of 1 μg/ml GP61 peptide. Supernatants were isolated 3 and 5 days later and analyzed for the presence of IL-10 and IFN-γ cytokines by ELISA, as previously described.

Statistical analysis: Statistical analysis was performed using Student's t test. Asterisk denotes $p<0.01$*, $p<0.001$, and $p<0.001$*.

Example 2

This example describes data indicating that persistent infection with LCMV CI13 is associated with increased IL-10 production.

Previous reports described increases in systemic IL-10 production in various chronic viral infections. Here, the kinetics of IL-10 secretion in chronic LCMV infections were analyzed.

Spleen cells were isolated from BALB/c mice day 0, 2, 8, 14, 20, 40, 94, and 124 days post infection with LCMV (CI13) or LCMV Ann ($2 \times 10^6$ PFU/mouse). ELISA for IL-10 were performed using isolated spleenocytes cultured for 48 hours in the absence of exogenous antigen (to allow for direct ex vivo presentation of viral antigens by splenic APCs) in complete RPMI. At the end of this culture period, the concentration of IL-10 in the supernatants was measured by ELISA. Data are represented as IL-10 (pg/ml) per $1 \times 10^6$ cells and are means of 3 mice per timepoint (FIGS. 3 and 4a).

IL-10 secretion peaks between days 14 and post LCMV CI13 infection (FIGS. 3 and 4a). In comparison, cells from mice infected with medium or high LCMV Arm secreted significantly less IL-10 (FIG. 4a). This difference was apparent regardless of the initial dose of virus, as increasing the inoculum of LCMV Arm from $1 \times 10^5$ PFU to $2 \times 10^6$ PFU resulted in comparable kinetics and levels of expression of IL-10. By day 40, while IL-10 production was undetectable in LCMV Arm-infected mice, mice infected with LCMV CI13 still produced significant amounts of this cytokine (FIG. 4a).

Additionally, CD8 T cells expressing IFN-γ responses predominate in the early phase of LCMV CI13 infection (FIG. 4b) at time points where IL-10 levels in both LCMV Arm and CI13-infected mice are non-detectable (FIG. 4a). Additionally, significantly higher levels of CD8 T cell IFN-γ was detected at earlier timepoints (day 5) in LCMV CI13 infected mice as compared to later (day 7) detection of peak IFN-γ responses in LCMV Arm infected. Increasing the dosages of LCMV Arm did not induce early day 5 response.

Taken together, these results indicate that LCMV CI13 induces a faster anti-viral response, possible linked to a higher binding affinity of the virus to its α-dystroglycan receptor.

Splenocytes secreting IL-10 were isolated upon stimulation with LCMV infected macrophages using anti-IL-10 antibodies and columns to capture the anti-IL-10 antibody labeled cells. Upon isolation of IL-10 secreting cells, surface marker expression was assessed by FACS. Increased numbers of CD4$^+$, CD8$^+$ and CD11 b$^+$ cells produced IL-10 in CI13-infected mice compared to Armstrong-infected mice was observed. Importantly, the majority of cells that produced IL-10 in CI13-infected mice were CD4$^+$ T lymphocytes (FIG. 4c). It is hypothesized that immune suppression mediated by LCMV CI13 infection is causatively linked to a shift in anti-viral associated cytokine production to production of the immunosuppressive cytokine IL-10. Blocking the signaling pathway of IL-10 may stimulate anti-viral T cells to initiate viral clearance.

Example 3

This example describes data indicating that anti-IL-10R mAb therapy decreases IL-10 and viral titers, and leads to disease amelioration.

To ascertain levels of IL-10 after IL-10R antibody treatment, spleen cells were isolated from BALB/c mice day 20 post LCMV (CI13) infection ($2 \times 10^6$ PFU/mouse). ELISA for IL-10 were performed after culturing the isolated spleen cells in complete RPMI for 48 hours. Data are represented as IL-10 pg/ml per $1 \times 10^6$ cells and are an average of 3 mice per group (FIG. 5).

Statistically significant differences (P=0.002 by Student's t test) were found between IL-10 levels in IL-10R antibody treated and control (PBS) treated mice. Mice treated with IL-10R antibody have reduced levels of IL-10.

IL-10 can inhibit immune responses by suppressing or skewing the development of helper T cell responses. (Fiorentino et al., *J Immunol* 146:3444 (1991), Liu et al., *Int Immunol* 10:1017 (1998)). Based on the finding that cells from mice persistently infected secreted high concentrations of IL-10, blocking the IL-10/IL-10R signaling pathway was studied to determine if removing the LCMV-CI13-induced immune suppression will re-establish an anti-viral Th1/Tc1 response.

BALB/c mice with LCMV CI13 and injected age-matched groups were infected with either a neutralizing anti-IL-10R mAb (which specifically targets the IL-10 receptor α-chain) or an IgG$_1$ isotype control mAb (FIGS. 6a and 6c) on days 0, 7 and 14 post-infection, or therapeutically treated after establishment of LCMV CI13 infection (FIGS. 6b and 6d). Disease severity was monitored in control or anti-IL-10R-treated LCMV CI13-infected mice by assessing overall health, body-weight, and spleen cell number over time. Bodyweight (grams) was measured every third day and clinical phenotype was monitored daily.

LCMV C13-infected mice treated with isotype control were observed to gradually lose body mass, weighing 30-40% less than age-matched naive mice (FIG. 6a). These mice also exhibited a non-shiny, scruffy coat (FIG. 7a).

Overall clinical appearance in mice treated with IL-10R antibody (250 μg/mouse) was improved as reflected in an 13.8% increased body weight (FIGS. 7c and 7d). These mice also exhibited a healthy shiny coat (FIG. 7b) and increased physical activity 15 days post infection.

Importantly, anti-IL-10R antibody was administered to LCMV CI13-infected mice at time points when the mice are already suffering from lymphopenia (day 5 and 12 after LCMV CI13 infection, when total numbers of splenocytes are 25% less than before infection, or day 7 and 14 after LCMV CI13 infection, when total numbers of splenocytes are reduced with 41%) and the same effect of the IL-10R antibody treatment was observed (FIG. 6b).

Whether protection of LCMV CI13-infected mice from symptoms of prolonged viral infection upon treatment with anti-IL-10R was associated with an improvement in viral clearance was studied. Viral loads were monitored at various timepoints in lymphoid versus non-lymphoid organs isolated from persistently infected mice treated with anti-IL-10R or IgG1. Viral titers were measured by conventional plaque assay and by a more recently developed, highly sensitive RT-PCR method (FIGS. 6c to 6f). The results are means of 4 studies with 5 mice per group.

RNA was isolated from homogenized organs of LCMV CI13 infected-mice treated with IL-10R antibody or isotype control. Quantitative real time PCR for LCMV genome copies on the cDNA obtained by reverse transcription was performed as described in Example 1.

In mice treated with anti-IL-10R, very low viral titers were detected by plaque assay in kidney, liver and lung 6 weeks after treatment, and this technique did not enable the detection of virus after 26 weeks. Furthermore, only low numbers of LCMV genomic copies were detected by the more sensitive RT-PCR technique in organs from anti-IL-10R-treated mice. Viral titers in organs from control IgG$_1$-treated mice remained high both in kidney and liver, and virus predominated in the kidney, which is characteristic of persistent LCMV infection. Data from these studies show that IL-10R antibody treatment is effective even when given therapeutically during established infection, as these mice did not exhibit any overt signs of disease and had a substantial reduction in viral titer in the liver, lung, and kidney 11 weeks after treatment (FIGS. 6d and 6f).

Splenocytes were incubated for 5 hours with NP118 peptide and Brefeldin A. CD8 T cell IFN-γ production was detected by means of intracellular cytokine antibody staining followed by FACS analysis. The total number of cytokine positive cells was calculated by relating the percentage of cytokine positive cells total number of spleen cells. Quantification of anti-LCMV antibodies early and late post treatment showed not difference between the IL-10R and isotype antibody-treated mice indicating that viral clearance was merely a result of enhancement of anti-viral T cells (FIG. 4b) and not enhancement of anti-LCMV antibodies. Finally, when similar studies were performed in B6 mice, where elevated levels of IL-10 have previously been reported (Brooks et al., J Virol 79:10514 (2005)), comparable effects of anti-IL-10R antibody treatment were found when administered at the time of infection, however less efficient upon therapeutic treatment, a result that might be linked to the slightly different Th1 rather that Th2 cytokine responses in this model.

Taken together, these results demonstrate that blocking IL-10 signaling results in T cell-mediated viral clearance. IL-10R antibody treatment is effective even when given therapeutically during established infection, as these mice did not exhibit any overt signs of disease and had a substantial reduction in viral titer in liver, lung, and kidney compared to control-treated mice.

Example 4

This example describes data indicating that anti-IL-10R therapy of mice persistently infected restores anti-viral CD8$^+$ responses.

BALB/c mice (6-week old) were infected with 2×10$^6$ pfu LCMV CI13. Mice were then treated with anti-IL-10R neutralizing antibody (250 μg injected i.p), or with IgG1 isotype control antibody on days 0, 7, and 14, or therapeutically day 7, and 14 post-infection. At 3 and 26 weeks, a drastic decrease in the overall number of spleen cells was observed in CI13-infected mice compared to non-infected littermates (FIG. 8a). Lymphopenia was reversed upon anti-IL-10R treatment, as significantly more splenocytes were isolated from anti-IL-10R than control IgG$_1$-injected mice (FIG. 8a) at 150 days after infection (p=0.0012). This quantitative increase of total cell numbers was confirmed in mice treated therapeutically with IL-10R antibody (FIG. 8a).

In addition, endogenous IL-10 production by splenocytes isolated early after CI13 infection was significantly reduced in anti-IL-10R-treated mice (p=0.002), but not saline or IgG1-injected mice, as detected by ELISA of splenocyte supernatants three weeks post treatment, indicating that early blockade of IL-10 prevented long term immunosuppressive effects mediated by CI13 infection (FIG. 8b). Qualitative LCMV antigen-specific early and late memory immune responses were studied in control-treated mice as well as mice treated with IL-10R antibody day 0, 7, and 14 or therapeutically treated day 7 and 14 post LCMV CI13. Splenocytes from IgG1-injected and anti-IL-10R-treated mice were isolated at early and late memory phase timepoints and stimulated with the MHC class I-restricted immuno-dominant LCMV peptide NP$_{118-126}$. The number of cytokine-producing cells was measured by intracellular cytokine staining and anti-IL-10R-treated mice were found to have significantly higher numbers of CD8$^+$ T cells producing IFN-γ than IgG1-injected mice (FIG. 8c).

Anti-viral NP$_{118-126}$ specific response increased at later memory stages in anti-IL-10R-treated mice compared to control IgG$_1$-injected mice. Importantly, therapeutic treatment with IL-10R antibody at day 7, and 14 post LCMV CI13 resulted in a similar significant increase of anti-viral memory responses. Thus, anti-IL-10R antibody treatment resulted in increased frequency and numbers of immune cells in mice persistently infected, and notably, a re-emergence of a potent anti-viral IFN-γ$^+$ CD8$^+$ T cell response.

The PD-1 inhibitory pathway, known to regulate immune responses (Ishida et al., Embo J 11:3887 (1992), Sharpe et al., Nat Rev Immunol 2:116 (2002), Freeman et al., J Exp Med 192:1027 (2000)) was also studied. It was previously reported that high expression of PD-1 was a characteristic of exhausted CD8 T cells in LCMV CI13 infected mice and that treatment with anti-PD-1 antibodies lead to proliferation of anti-viral T cells and enhancement of viral clearance (Barber et al., Nature 439:682 (2006)).

To study whether PD-1 was involved, mice were treated with IL-10R antibody or isotype on day 7 and 14 post-CI13 infection. Increase in anti-viral responses and enhancement of viral clearance were monitored upon therapeutically blocking IL-10 signaling with IL-10R antibody, T cell expression of PD-1 in IL-10R and isotype antibody treated mice. PD-1 was expressed on both CD4 and CD8 T cells upon LCMV CI13 infection, as detected by labeling of the splenocytes with a fluorescent PD-1 antibody followed by FACS analysis (FIG. 8d). However, anti-IL10R antibody treatment significantly reduced PD-1 expression. These results point to the beneficial role of IL-10R antibody treatment on reducing expression of CD8 PD-1 in chronically infected mice leading to circumvention of CD8 T cell exhaustion and enhanced viral clearance.

To further study the effect of anti-IL-10R antibody treatment on the immune response to LCMV, the phenotype of splenocytes in IgG1-injected and anti-IL10R-treated CI13-infected mice were compared (FIG. 9). The effect of treatment with IgG1 isotype control mAb or anti-IL-10R antibody on day 0, 7 and 14 after infection on different splenic cell subsets quantitatively was monitored. Spleens of mice infected 20 and 150 days previously with LCMV CI13 were harvested, and cell suspensions stained with cell surface antibodies. Age-matched uninfected mice were included as controls.

Although CI13 infection caused a reduction in the numbers of immune cells present in the spleen at day 21 regardless of treatment, by day 150 post-infection the numbers of $CD4^+$, $CD8^+$, $B220^+$ and $CD11c^+$ cells in anti-IL-10R-treated mice were similar to those in naive mice, whereas the numbers of these cell types in IgG1-injected mice remained scarce. To rule out that reappearance of B cells could lead to antibody-mediated viral clearance, the concentration of LCMV specific IgG antibodies were measured-no difference in antibody levels was found between IL-10R antibody and IgG1 antibody treated mice. Furthermore, numbers of $CD11b^+$ cells in the spleen at day 150 post-infection were comparable between groups, suggesting that the decrease in viral titers after anti-IL-10R treatment was not due solely to enhanced clearance of virally infected macrophages.

Taken together, these results indicated that anti-IL-10R treatment restores cell numbers in LCMV CI13-infected mice.

Example 5

This example describes data indicating that CD8α+ DCs are eliminated following LCMV CI13 but not Arm infection.

Whether the loss of anti-viral T cells following LCMV CI13 infection could be mediated by APCs was studied by assessing the effect of persistent LCMV CI13 infection on the ratio of different subsets of dendritic cells (DCs), which are the most potent APCs and have been shown to play a crucial role in the priming of LCMV-specific CTLs (Probst et al., *J Immunol* 174:3920 (2005)). The ratio of $CD8α^-$ and $CD8α^+$ DC within the $CD11c^{30}$ $CD3^-$ subset was determined following LCMV infection. Splenocytes were isolated from LCMV Armstrong or LCMV CI13 infected BALB/c mice 1-6 weeks post infection. Cell suspensions were prepared by digestion with collagenase D, and DC-T cell complexes were disrupted by incubating cell suspension in EDTA buffer. Cells were then stained with fluorescent mAb to CD11c, CD3 and CD8α. BALB/c mice were infected with LCMV CI13. Mice were treated with IL-10R antibody or control IgG1 day 7 and 14 post infection, and $CD8a^+$ and $CD8a^+$ subsets were quantified.

At day 7 post-infection a decline in the percentage of CD11c+CD8+ DCs was observed in both Arm- and CI13-infected mice. This is possibly because at this time point more than 50% of CD11c+ DCs are infected in CI13-infected mice (Sevilla et al., *J Exp Med* 192:1249 (2000)), making this DC subset an excellent target for destruction by the host immune system. In contrast, a minimal infection of CD11c+ cells was observed in LCMV Arm-infected mice in the same study. A gradual and significant loss of splenic $CD8α^+$ DCs in mice infected with LCMV CI13 compared to mice infected with LCMV Arm was observed (FIG. 10a).

The percent of $CD8α^+$ DCs was significantly lower at day 43 after LCMV CI13, but not LCMV Arm infection. In contrast, an increase in the fraction of $CD8α^-$ cells was observed in the early phase of CI13 infection, possibly as a compensatory mechanism to the loss off the $CD8α^+$ population (FIG. 10c). By day 43 this subset was comparable to that of non-infected mice. In LCMV Arm infected, mice $CD8α^-$ DCs were reduced in the early phase of infection indicating that the viral strains target different DC subsets. The predominant loss of $CD8α^+$ DCs after LCMV CI13 infection could was significantly restored by therapeutic IL-10R antibody treatment 6 weeks post LCMV CI13 infection (FIG. 10b). Additionally, this treatment restored the imbalance between CD8α+ and CD8α- DC subsets (FIG. 10d).

Collectively, these data strengthen the hypothesis that in chronically infected mice the CD8+ DC population is selectively and continually eliminated leading to a gradual skewing of the ratio of DC subsets. As a result, although IFN-γ and TNF-α responses prevail early in the CI13 infection (FIG. 4b), once the CD8+ Th1-promoting DC subset is eliminated, CD8- DC subsets will predominate, promoting increased IL-10 production (FIG. 4a).

Example 6

This example describes data indicating that $CD8α^-$ DCs preferentially prime IL-10 production during the development of chronic infection.

Previous studies suggest that different DC subsets vary in their ability to prime effector T cells (Maldonado-Lopez et al., *J Exp Med* 189:587 (1999), Pulendran et al., *Proc Natl Acad Sci USA* 96:1036 (1999), Liu et al., *Cell* 106:259 (2001)). In particular, evidence suggests that DCs can induce the production of Th1 or Th2 cytokines or IL-10 depending on the cytokine milieu in which they encounter antigen (Maldonado-Lopez et al., *J Immunol* 167:4345 (2001), Maldonado-Lopez et al., *Semin Immunol* 13:275 (2001), Liu et al., *Int Immunol* 10: 1017 (1998)). Thus, whether differential T cell priming by DC subsets modulated the nature of the anti-viral T cell response was studied.

$CD11c^+CD3^-$ cells were isolated from the spleens of LCMV CI13-infected mice and sorted into $CD8α^+$ and $CD8α^-$ DCs by flow cytometry 2, 7, and 15 days after infection with LCMV CI13 or LCMV Armstrong (FIG. 11a). Early time points after infection were chosen to allow for capture and processing of viral antigens by DCs directly in vivo, during the early phase of LCMV infection, which is associated with viral dissemination and replication. At the early time points, viral antigen is still detectable in vivo to induce stimulation in the system as detected by RT-PCR. The isolated DCs were then cultured for 5 days with $GP_{61-80}$-specific $CD4^+$ T cells isolated from naive T cell receptor (TCR) transgenic (tg) SMARTA mice at a ratio of 4:1. No exogenous antigen was added to the cultures to ensure that only viral antigen processed in vivo was presented by the DCs. The ability of the different DC subsets to stimulate LCMV-specific $CD4^+$ T cells was determined by measuring the amounts of cytokines released in the supernatants at the end of the culture.

IL-10 production by anti-viral $CD4^+$ T cells was induced predominantly by DCs isolated from LCMV CI13-infected mice, and was preferentially mediated by the $CD8α^-$ DC subset (FIG. 11b). Production of IL-10 by $CD4^+$ T cells stimulated with $CD8α^-$ DCs from LCMV CI13-infected mice was highest when DCs were isolated from mice infected 7 days earlier. This corresponded to the time point at which $CD8α^+$ DC numbers started to decline, suggesting that IL-10 induction upon LCMV Cl13 infection was the consequence of T cell priming by the remaining CD8α⁻ DCs.

In contrast, very low or undetectable levels of IL-10 were produced by T cells stimulated with CD8α⁻ (FIG. 11b) or CD8α⁺ DCs (FIG. 1e) from mice infected with LCMV Arm (open bars). Additionally, both CD8α⁻ and CD8α⁺ DCs from LCMV Cl13- and LCMV Arm-infected mice were able to stimulate IFN-γ production by CD4⁺ T cells (FIGS. 11c and 11f).

To rule out any contamination due to cytokine release by APCs, DCs were irradiated, and levels of both IL-10 and IFN-γ were measured in the supernatants of DC cultures devoid of T cells. These background levels were below 1 pg/ml.

CD11c⁺CD8α⁻ cells from LCMV Cl13-infected mice were found to induce significantly higher amounts of IL-10 compared to CD8α⁺ DCs (FIGS. 11d and 11g). While the amount of IL-10 and IFN-γ varied from one condition to another, the IL-10/IFN-γ ratio was significantly higher when DCs from LCMV Cl13-infected mice were used, regardless of the time at which these cells were isolated.

These results indicate that the predominant loss of the CD8α⁺ DC population in LCMV Cl13-infected mice (FIG. 10a and 10c) allows the remaining CD8α⁻ subset to stimulate IL-10 production by T cells, resulting in suppression of the anti-viral T cell response and maintenance of the viral infection. CD8α⁺/CD8α⁻ DC imbalance is restored upon IL-10R antibody treatment (FIG. 10b and 10d).

What is claimed is:

1. A method of treating a subject with an established or chronic arenavirus or a herpesvirus infection, comprising administering to a subject an amount of an IL-10 Receptor (IL-10R) antagonist sufficient to reduce arenavirus or herpesvirus titer.

2. The method of claim 1, wherein the antagonist comprises a polypeptide.

3. The method of claim 1, wherein the antagonist comprises an antibody.

4. The method of claim 3, wherein the antibody is mammalian, primatized, humanized or fully human.

5. The method of claim 3, wherein the antibody is monoclonal or polyclonal.

6. The method of claim 3, wherein the antibody binds to IL-10R alpha chain extracellular domain.

7. The method of claim 3, wherein the antibody binds to IL-10R beta chain extracellular domain.

8. The method of claim 3, wherein the antibody is selected from or produced by 1B1.3a, 1B1.2 hybridoma and anti-mouse IL-10R.

9. The method of claim 3, wherein the antibody has substantially the same binding affinity as an antibody selected from or produced by 1B1.3a, 1B1.2 hybridoma and anti-mouse IL-10R.

10. The method of claim 3, wherein the antibody competitively inhibits binding of an antibody selected from or produced by 1B1.3a, 1B1.2 hybridoma and anti-mouse IL-10R to IL-10R.

11. The method of claim 3, wherein the antibody comprises a fragment or subsequence of a full length antibody having two heavy chains and two light chains.

12. The method of claim 11, wherein the fragment or subsequence of a full length antibody is selected from Fab, Fab', F(ab')$_2$, Fv, Fd, single-chain Fv (scFv), disulfide linked Fv, light chain variable (VL) and heavy chain variable (VH).

13. The method of claim 1, wherein the IL-10 Receptor (IL-10R) antagonist comprises soluble IL-10R.

14. The method of claim 1, wherein the antagonist inhibits IL-10 signaling or expression.

15. The method of claim 1, wherein the IL-10 Receptor (IL-10R) antagonist inhibits binding of a ligand to IL-10R.

16. The method of claim 15, wherein the ligand comprises IL-10.

17. The method of claim 1, wherein the viral infection is chronic.

18. The method of claim 1, wherein the subject is a mammal.

19. The method of claim 1, wherein the subject is a human.

20. The method of claim 1, wherein the subject has not been diagnosed with an autoimmune disease or an inflammatory disease.

21. The method of claim 1, wherein the herpesvirus is β-herpesvirus, γ-herpesvirus, Epstein Barr Virus (EBV), Cytomegalovirus (CMV), varicella zoster virus (VZV/HHV-3), or human herpes virus 1, 2, 4, 5, 6, 7, or 8 (HHV-8, Kaposi's sarcoma-associated virus).

22. The method of claim 1, wherein the arenavirus is lymphocytic choriomeningitis virus (LCMV), Junin virus, Lassa virus, Guanarito virus, Sabia virus or Machupo virus.

23. The method of claim 1, wherein the treatment reduces virus proliferation, reduces the amount of a virus protein or reduces the amount of a virus nucleic acid.

24. The method of claim 1, wherein the amount of antagonist is sufficient to increase or stimulate virus clearance, reduce or inhibit virus infection, reduce or inhibit increase in virus titer, reduce or inhibit virus proliferation, reduce or inhibit synthesis of a virus protein or a virus nucleic acid, or reduce or inhibit virus reactivation from latency.

25. The method of claim 1, wherein the treatment reduces one or more physiological conditions, disorders, illness, diseases or symptoms caused by or associated with virus infection, reactivation or pathology.

26. The method of claim 1, wherein the treatment improves one or more physiological conditions, disorders, illness, diseases or symptoms caused by or associated with virus infection, reactivation or pathology.

27. The method of claim 1, wherein the treatment reduces or ameliorates an adverse complication associated with virus infection, reactivation or pathology.

28. The method of claim 1, wherein the antagonist is administered following infection of the subject with virus.

29. The method of claim 1, wherein the antagonist is administered prior to, substantially contemporaneously with or following virus reactivation from latency.

30. The method of claim 1, wherein a plurality of antagonists are administered to the subject.

31. A method of increasing numbers or activation of an immune cell in a subject with an established or chronic arenavirus or a herpesvirus infection to reduce virus titer, comprising administering to a subject an amount of an IL-10 Receptor (IL-10R) antagonist sufficient to increase numbers or activation of the immune cell in the subject thereby reducing virus titer.

32. The method of claim 31, wherein the immune cell is a T cell or dendritic cell (DC).

33. The method of claim 31, wherein the immune cell expresses a protein selected from the group consisting of: CD4+, CD8+, B220+ and CD11c+ cells.

34. A method of increasing or inducing an antiviral CD8+ T cell response in a subject with an established or chronic arenavirus or a herpesvirus infection to reduce virus titer, comprising administering to a subject an amount of an IL-10 Receptor (IL-10R) antagonist sufficient to increase or induce an antiviral CD8+ T cell response in the subject thereby reducing virus titer.

* * * * *

SEQUENCE LISTING

<160> NUMBER OF SEQ ID NOS: 7

<210> SEQ ID NO 1
<211> LENGTH: 578
<212> TYPE: PRT
<213> ORGANISM: Homo sapiens

<400> SEQUENCE: 1

```
Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Tyr Phe Thr Val Thr Asn Val Ile Ile Phe Phe
225                 230                 235                 240

Ala Phe Val Leu Leu Leu Ser Gly Ala Leu Ala Tyr Cys Leu Ala Leu
                245                 250                 255
```

```
Gln Leu Tyr Val Arg Arg Lys Lys Leu Pro Ser Val Leu Leu Phe
                260                 265                 270
Lys Lys Pro Ser Pro Phe Ile Phe Ile Ser Gln Arg Pro Ser Pro Glu
            275                 280                 285
Thr Gln Asp Thr Ile His Pro Leu Asp Glu Ala Phe Leu Lys Val
            290                 295                 300
Ser Pro Glu Leu Lys Asn Leu Asp Leu His Gly Ser Thr Asp Ser Gly
305                 310                 315                 320
Phe Gly Ser Thr Lys Pro Ser Leu Gln Thr Glu Pro Gln Phe Leu
                325                 330                 335
Leu Pro Asp Pro His Pro Gln Ala Asp Arg Thr Leu Gly Asn Gly Glu
                340                 345                 350
Pro Pro Val Leu Gly Asp Ser Cys Ser Ser Gly Ser Asn Ser Thr
                355                 360                 365
Asp Ser Gly Ile Cys Leu Gln Glu Pro Ser Leu Ser Pro Ser Thr Gly
    370                 375                 380
Pro Thr Trp Glu Gln Gln Val Gly Ser Asn Ser Arg Gly Gln Asp Asp
385                 390                 395                 400
Ser Gly Ile Asp Leu Val Gln Asn Ser Glu Gly Arg Ala Gly Asp Thr
                405                 410                 415
Gln Gly Gly Ser Ala Leu Gly His His Ser Pro Pro Glu Pro Glu Val
                420                 425                 430
Pro Gly Glu Glu Asp Pro Ala Ala Val Ala Phe Gln Gly Tyr Leu Arg
            435                 440                 445
Gln Thr Arg Cys Ala Glu Glu Lys Ala Thr Lys Thr Gly Cys Leu Glu
            450                 455                 460
Glu Glu Ser Pro Leu Thr Asp Gly Leu Gly Pro Lys Phe Gly Arg Cys
465                 470                 475                 480
Leu Val Asp Glu Ala Gly Leu His Pro Pro Ala Leu Ala Lys Gly Tyr
                485                 490                 495
Leu Lys Gln Asp Pro Leu Glu Met Thr Leu Ala Ser Ser Gly Ala Pro
            500                 505                 510
Thr Gly Gln Trp Asn Gln Pro Thr Glu Glu Trp Ser Leu Leu Ala Leu
            515                 520                 525
Ser Ser Cys Ser Asp Leu Gly Ile Ser Asp Trp Ser Phe Ala His Asp
            530                 535                 540
Leu Ala Pro Leu Gly Cys Val Ala Ala Pro Gly Gly Leu Leu Gly Ser
545                 550                 555                 560
Phe Asn Ser Asp Leu Val Thr Leu Pro Leu Ile Ser Ser Leu Gln Ser
                565                 570                 575
Ser Glu

<210> SEQ ID NO 2
<211> LENGTH: 325
<212> TYPE: PRT
<213> ORGANISM: Homo sapiens

<400> SEQUENCE: 2

Met Ala Trp Ser Leu Gly Ser Trp Leu Gly Gly Cys Leu Leu Val Ser
1               5                   10                  15
Ala Leu Gly Met Val Pro Pro Glu Asn Val Arg Met Asn Ser Val
                20                  25                  30
Asn Phe Lys Asn Ile Leu Gln Trp Glu Ser Pro Ala Phe Ala Lys Gly
                35                  40                  45
```

-continued

```
Asn Leu Thr Phe Thr Ala Gln Tyr Leu Ser Tyr Arg Ile Phe Gln Asp
 50                  55                  60
Lys Cys Met Asn Thr Thr Leu Thr Glu Cys Asp Phe Ser Ser Leu Ser
 65                  70                  75                  80
Lys Tyr Gly Asp His Thr Leu Arg Val Arg Ala Glu Phe Ala Asp Glu
                 85                  90                  95
His Ser Asp Trp Val Asn Ile Thr Phe Cys Pro Val Asp Asp Thr Ile
            100                 105                 110
Ile Gly Pro Pro Gly Met Gln Val Glu Val Leu Ala Asp Ser Leu His
        115                 120                 125
Met Arg Phe Leu Ala Pro Lys Ile Glu Asn Glu Tyr Glu Thr Trp Thr
130                 135                 140
Met Lys Asn Val Tyr Asn Ser Trp Thr Tyr Asn Val Gln Tyr Trp Lys
145                 150                 155                 160
Asn Gly Thr Asp Glu Lys Phe Gln Ile Thr Pro Gln Tyr Asp Phe Glu
                165                 170                 175
Val Leu Arg Asn Leu Glu Pro Trp Thr Thr Tyr Cys Val Gln Val Arg
            180                 185                 190
Gly Phe Leu Pro Asp Arg Asn Lys Ala Gly Glu Trp Ser Glu Pro Val
        195                 200                 205
Cys Glu Gln Thr Thr His Asp Glu Thr Val Pro Ser Trp Met Val Ala
210                 215                 220
Val Ile Leu Met Ala Ser Val Phe Met Val Cys Leu Ala Leu Leu Gly
225                 230                 235                 240
Cys Phe Ala Leu Leu Trp Cys Val Tyr Lys Lys Thr Lys Tyr Ala Phe
                245                 250                 255
Ser Pro Arg Asn Ser Leu Pro Gln His Leu Lys Glu Phe Leu Gly His
            260                 265                 270
Pro His His Asn Thr Leu Leu Phe Phe Ser Phe Pro Leu Ser Asp Glu
        275                 280                 285
Asn Asp Val Phe Asp Lys Leu Ser Val Ile Ala Glu Asp Ser Glu Ser
290                 295                 300
Gly Lys Gln Asn Pro Gly Asp Ser Cys Ser Leu Gly Thr Pro Pro Gly
305                 310                 315                 320
Gln Gly Pro Gln Ser
                325

<210> SEQ ID NO 3
<211> LENGTH: 3649
<212> TYPE: DNA
<213> ORGANISM: Homo sapiens

<400> SEQUENCE: 3
agtcccagcc caagggtagc tggaggcgcg caggccggct ccgctccggc cccggacgat    60
gcggcgcgcc caggatgctg ccgtgcctcg tagtgctgct ggcggcgctc ctcagcctcc   120
gtcttggctc agacgctcat gggacagagc tgcccagccc tccgtctgtg tggtttgaag   180
cagaattttt ccaccacatc ctccactgga cacccatccc aaatcagtct gaaagtacct   240
gctatgaagt ggcgctccct aggtatggaa tagagtcctg gaactccatc tccaactgta   300
gccagaccct gtcctatgac cttaccgcag tgaccttgga cctgtaccac agcaatggct   360
accgggccag agtgcgggct gtggacggca gccggcactc caactggacc gtcaccaaca   420
cccgcttctc tgtggatgaa gtgactctga cagttggcag tgtgaaccta gagatccaca   480
atggcttcat cctcgggaag attcagctac ccaggcccaa gatggccccc gcaaatgaca   540
```

```
catatgaaag catcttcagt cacttccgag agtatgagat tgccattcgc aaggtgccgg    600
gaaacttcac gttcacacac aagaaagtaa acatgaaaa cttcagcctc ctaacctctg    660
gagaagtggg agagttctgt gtccaggtga aaccatctgt cgcttcccga agtaacaagg    720
ggatgtggtc taaagaggag tgcatctccc tcaccaggca gtatttcacc gtgaccaacg    780
tcatcatctt ctttgccttt gtcctgctgc tctccggagc cctcgcctac tgcctggccc    840
tccagctgta tgtgcggcgc cgaaagaagc tacccagtgt cctgctcttc aagaagccca    900
gcccctttcat cttcatcagc cagcgtccct ccccagagac ccaagacacc atccacccgc    960
ttgatgagga ggccttttg aaggtgtccc cagagctgaa gaacttggac ctgcacggca    1020
gcacagacag tggctttggc agcaccaagc catccctgca gactgaagag ccccagttcc    1080
tcctccctga ccctcacccc caggctgaca gaacgctggg aaacggggag cccctgtgc    1140
tgggggacac ctgcagtagt ggcagcagca atagcacaga cagcgggatc tgcctgcagg    1200
agcccagcct gagcccagc acagggccca cctgggagca acaggtgggg agcaacagca    1260
ggggccagga tgacagtggc attgacttag ttcaaaactc tgagggccgg gctggggaca    1320
cacagggtgg ctcggccttg ggccaccaca gtccccgga gcctgaggtg cctggggaag    1380
aagacccagc tgctgtggca ttccagggtt acctgaggca gaccagatgt gctgaagaga    1440
aggcaaccaa gacaggctgc ctggaggaag aatcgcccct gacagatggc cttggcccca    1500
aattcgggag atgcctggtt gatgaggcag gcttgcatcc accagccctg gccaagggct    1560
atttgaaaca ggatcctcta gaaatgactc tggcttcctc aggggcccca acggacagt    1620
ggaaccagcc cactgaggaa tggtcactcc tggccttgag cagctgcagt gacctgggaa    1680
tatctgactg gagctttgcc catgaccttg cccctctagg ctgtgtggca gccccaggtg    1740
gtctcctggg cagctttaac tcagacctgg tcaccctgcc cctcatctct agcctgcagt    1800
caagtgagtg actcgggctg agaggctgct tttgatttta gccatgcctg ctcctctgcc    1860
tggaccagga ggagggcccc tggggcagaa gttaggcacg aggcagtctg ggcacttttc    1920
tgcaagtcca ctgggctgg ccccagccag gccctgcagg gctggtcagg gtgtctgggg    1980
caggaggagg ccaactcact gaactagtgc agggtatgtg ggtggcactg acctgttctg    2040
ttgactgggg ccctgcagac tctggcagag ctgagaaggg cagggacctt ctccctccta    2100
ggaactcttt cctgtatcat aaaggattat ttgctcaggg gaaccatggg gctttctgga    2160
gttgtggtga ggccaccagg ctgaagtcag ctcagaccca gacctccctg cttaggccac    2220
tcgagcatca gagcttccag caggaggaag ggctgtagga atggaagctt cagggccttg    2280
ctgctgggt catttttagg ggaaaaagga ggatatgatg gtcacatggg gaacctcccc    2340
tcatcgggcc tctgggcag gaagcttgtc actggaagat cttaaggtat atattttctg    2400
gacactcaaa cacatcataa tggattcact gaggggagac aaagggagcc gagaccctgg    2460
atggggcttc cagctcagaa cccatccctc tggtgggtac ctctggcacc catctgcaaa    2520
tatctccctc tctccaacaa atggagtagc atcccctgg ggcacttgct gaggccaagc    2580
cactcacatc ctcactttgc tgccccacca tcttgctgac aacttccaga gaagccatgg    2640
ttttttgtat tggtcataac tcagcccttt gggcggcctc tgggcttggg caccagctca    2700
tgccagcccc agagggtcag ggttggaggc ctgtgcttgt gtttgctgct aatgtccagc    2760
tacagaccca gaggataagc cactgggcac tgggctgggg tccctgcctt gttggtgttc    2820
agctgtgtga ttttggacta gccacttgtc agagggcctc aatctcccat ctgtgaaata    2880
```

-continued

```
aggactccac ctttagggga ccctccatgt ttgctgggta ttagccaagc tggtcctggg    2940
agaatgcaga tactgtccgt ggactaccaa gctggcttgt ttcttatgcc agaggctaac    3000
agatccaatg ggagtccatg gtgtcatgcc aagacagtat cagacacagc cccagaaggg    3060
ggcattatgg gccctgcctc cccataggcc atttggactc tgccttcaaa caaaggcagt    3120
tcagtccaca ggcatggaag ctgtgagggg acaggcctgt gcgtgccatc cagagtcatc    3180
tcagccctgc ctttctctgg agcattctga aaacagatat tctggcccag ggaatccagc    3240
catgaccccc acccctctgc caaagtactc ttaggtgcca gtctggtaac tgaactccct    3300
ctggaggcag gcttgaggga ggattcctca gggttccctt gaaagcttta tttatttatt    3360
ttgttcattt atttattgga gaggcagcat tgcacagtga agaattctg atatctcag     3420 gagccccgaa attctagctc tgactttgct gtttccagtg gtatgacctt ggagaagtca    3480
cttatcctct tggagcctca gtttcctcat ctgcagaata atgactgact tgtctaattc    3540
gtagggatgt gaggttctgc tgaggaaatg ggtatgaatg tgccttgaac acaaagctct    3600
gtcaataagt gatacatgtt ttttattcca ataaattgtc aagaccaca              3649
```

<210> SEQ ID NO 4
<211> LENGTH: 1935
<212> TYPE: DNA
<213> ORGANISM: Homo sapiens

<400> SEQUENCE: 4

```
atctccgctg gttcccggaa gccgccgcgg acaagctctc ccgggcgcgg gcggggtcg      60 tgtgcttgga ggaagccgcg gaaccccag cgtccgtcca tggcgtggag ccttgggagc     120
tggctgggtg gctgcctgct ggtgtcagca ttgggaatgg taccacctcc cgaaaatgtc    180
agaatgaatt ctgttaattt caagaacatt ctacagtggg agtcacctgc ttttgccaaa    240
gggaacctga ctttcacagc tcagtaccta agttatagga tattccaaga taaatgcatg    300
aatactacct tgacggaatg tgatttctca agtctttcca gtatggtgga ccacaccttg    360
agagtcaggg ctgaatttgc agatgagcat tcagactggg taaacatcac cttctgtcct    420
gtggatgaca ccattattgg acccctggaa atgcaagtag aagtacttgc tgattctttt     480
catatgcgtt tcttagcccc taaaattgag aatgaatacg aaacttggac tatgaagaat    540
gtgtataact catggactta taatgtgcaa tactggaaaa acggtactga tgaaaagttt    600
caaattactc cccagtatga ctttgaggtc ctcagaaacc tggagccatg gacaacttat    660
tgtgttcaag ttcgagggtt tcttcctgat cggaacaaag ctggggaatg gagtgagcct    720
gtctgtgagc aaaacaaccca tgacgaaacg gtcccctcct ggatggtggc cgtcatcctc    780
atggcctcgg tcttcatggt ctgcctggca ctcctcggct gcttcgcctt gctgtggtgc    840
gtttacaaga agacaaagta cgccttctcc cctaggaatt ctcttccaca gcacctgaaa    900 gagttttgg gccatcctca tcataacaca cttctgtttt tctcctttcc attgtcggat    960
gagaatgatg tttttgacaa gctaagtgtc attgcagaag actctgagag cggcaagcag   1020
aatcctggtg acagctgcag cctcgggacc ccgcctgggc aggggcccca aagctaggct   1080
ctgagaagga aacacactcg gctgggcaca gtgacgtact ccatctcaca tctgcctcag   1140
tgagggatca gggcagcaaa caagggccaa gaccatctga gccagcccca catctagaac   1200
tcccagaccc tggacttagc caccagagag ctacatttta aaggctgtct tggcaaaaat   1260
actccatttg ggaactcact gccttataaa ggctttcatg atgttttcag aagttggcca   1320
ctgagagtgt aattttcagc ctttatatc actaaaataa gatcatgttt taattgtgag   1380
```

```
aaacagggcc gagcacagtg gctcacgcct gtaataccag caccttagag gtcgaggcag    1440
gcggatcact tgaggtcagg agttcaagac cagcctggcc aatatggtga aacccagtct    1500
ctactaaaaa tacaaaaatt agctaggcat gatggcgcat gcctataatc ccagctactc    1560
gagtgcctga ggcaggagaa ttgcatgaac ccgggaggag gaggaggagg ttgcagtgag    1620
ccgagatagc ggcactgcac tccagcctgg gtgacaaagt gagactccat ctcaaaaaaa    1680 aaaaaaaaa aaattgtgag aaacagaaat acttaaaatg aggaataaga atggagatgt    1740
tacatctggt agatgtaaca ttctaccaga ttatggatgg actgatctga aaatcgacct    1800
caactcaagg gtggtcagct caatgctaca cagagcacgg acttttggat tctttgcagt    1860
actttgaatt tattttttcta cctatatatg ttttatatgc tgctggtgct ccattaaagt    1920
tttactctgt gttgc                                                     1935

<210> SEQ ID NO 5
<211> LENGTH: 1629
<212> TYPE: DNA
<213> ORGANISM: Homo sapiens

<400> SEQUENCE: 5
acacatcagg ggcttgctct tgcaaaacca aaccacaaga cagacttgca aaagaaggca      60
tgcacagctc agcactgctc tgttgcctgg tcctcctgac tggggtgagg gccagcccag     120
gccagggcac ccagtctgag aacagctgca cccacttccc aggcaacctg cctaacatgc     180
ttcgagatct ccgagatgcc ttcagcagag tgaagacttt ctttcaaatg aaggatcagc     240
tggacaactt gttgttaaag gagtccttgc tggaggactt taagggttac ctgggttgcc     300
aagccttgtc tgagatgatc cagttttacc tggaggaggt gatgcccaa gctgagaacc     360 aagacccaga catcaaggcg catgtgaact ccctggggga gaacctgaag accctcaggc     420
tgaggctacg gcgctgtcat cgatttcttc cctgtgaaaa caagagcaag gccgtggagc     480
aggtgaagaa tgcctttaat aagctccaag agaaaggcat ctacaaagcc atgagtgagt     540
ttgacatctt catcaactac atagaagcct acatgacaat gaagatacga aactgagaca     600
tcagggtggc gactctatag actctaggac ataaattaga ggtctccaaa atcggatctg     660
gggctctggg atagctgacc cagccccttg agaaacctta ttgtacctct cttatagaat     720
atttattacc tctgatacct caaccccat ttctatttat ttactgagct tctctgtgaa     780
cgatttagaa agaagcccaa tattataatt ttttcaata tttattattt tcacctgttt     840
ttaagctgtt tccataggt gacacactat ggtatttgag tgttttaaga taaattataa     900
gttacataag ggaggaaaaa aaatgttctt tggggagcca acagaagctt ccattccaag     960
cctgaccacg ctttctagct gttgagctgt tttccctgac ctccctctaa tttatcttgt    1020
ctctgggctt gggcttcct aactgctaca aatactctta ggaagagaaa ccagggagcc    1080
cctttgatga ttaattcacc ttccagtgtc tcggagggat tcccctaacc tcattcccca    1140
accacttcat tcttgaaagc tgtggccagc ttgttattta taacaaccta aatttggttc    1200
taggccgggc gcggtggctc acgcctgtaa tcccagcact ttgggaggct gaggcgggtg    1260
gatcacttga ggtcaggagt tcctaaccag cctggtcaac atggtgaaac cccgtctcta    1320
ctaaaaatac aaaaattagc cgggcatggt ggcgcgcacc tgtaatccca gctacttggg    1380
aggctgaggc aagagaattg cttgaaccca ggagatggaa gttgcagtga gctgatatca    1440
tgcccctgta ctccagcctg ggtgacagag caagactctg tctcaaaaaa taaaaataaa    1500
```

```
                                          -continued
aataaatttg gttctaatag aactcagttt taactagaat ttattcaatt cctctgggaa    1560
tgttacattg tttgtctgtc ttcatagcag attttaattt tgaataaata aatgtatctt    1620
attcacatc                                                            1629

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 6
gcaactgctg tgttcccgaa ac                                             22

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 7
cattcacctg gactttgtca gactc                                          25
```